US012727751B2

(12) United States Patent
Wachli et al.

(10) Patent No.: US 12,727,751 B2
(45) Date of Patent: Sep. 8, 2026

(54) LIGHTED SURGICAL ACCESS SYSTEM

(71) Applicant: Applied Medical Resources Corporation, Rancho Santa Margarita, CA (US)

(72) Inventors: Serene Wachli, Rancho Santa Margarita, CA (US); Joel Velasco, Rancho Santa Margarita, CA (US); Khodr Saleh, Whittier, CA (US); Alex Diehl, Ladera Ranch, CA (US); Jonathan Rothschild, Huntington Beach, CA (US); Andrew Nguyen, Rancho Santa Margarita, CA (US); Ghassan Sakakine, Rancho Santa Margarita, CA (US); Patrick Elliott, Rancho Santa Margarita, CA (US); Scott V. Taylor, Rancho Santa Margarita, CA (US); Steven Kessler, Rancho Santa Margarita, CA (US); Deryk Perez, Rancho Santa Margarita, CA (US); Luis Salazar, Compton, CA (US); Alexis Penaloza, Riverside, CA (US); Ralph Sias, Oceanside, CA (US); Tina Talwar, Rancho Santa Margarita, CA (US); Cory Hague, Aliso Viejo, CA (US); Boun Pravong, Rancho Santa Margarita, CA (US); Kennii Pravongviengkham, Rancho Santa Margarita, CA (US); Suraj Sharma, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 496 days.

(21) Appl. No.: 18/030,039

(22) PCT Filed: Oct. 8, 2021

(86) PCT No.: PCT/US2021/054312
§ 371 (c)(1),
(2) Date: Apr. 3, 2023

(87) PCT Pub. No.: WO2022/076918
PCT Pub. Date: Apr. 14, 2022

(65) Prior Publication Data

US 2023/0329692 A1 Oct. 19, 2023

Related U.S. Application Data

(60) Provisional application No. 63/248,319, filed on Sep. 24, 2021, provisional application No. 63/089,486, filed on Oct. 8, 2020.

(51) Int. Cl.
*A61B 17/02* (2006.01)
*A61B 1/07* (2006.01)
(Continued)

(52) U.S. Cl.
CPC .............. *A61B 1/07* (2013.01); *A61B 1/3132* (2013.01); *A61B 17/0293* (2013.01);
(Continued)

(58) Field of Classification Search
CPC ............ A61B 17/3423; A61B 17/3431; A61B 2017/3427; A61B 2017/3429; A61B 17/0293
See application file for complete search history.

(56) References Cited

U.S. PATENT DOCUMENTS 3,807,393 A 4/1974 McDonald
5,159,921 A 11/1992 Hoover
(Continued)

FOREIGN PATENT DOCUMENTS

DE 10 2016 114 129 A1 2/2018
WO WO 2004/075930 A2 9/2004
(Continued)

OTHER PUBLICATIONS

European Patent Office, The International Search Report and Written Opinion for International Application No. PCT/US2021/54312, entitled "Lighted Surgical Access System," mailed Jan. 14, 2022, 13 pgs.

(Continued)

*Primary Examiner* — Eduardo C Robert
*Assistant Examiner* — Steven J Cotroneo
(74) *Attorney, Agent, or Firm* — Patrick Ikehara

(57) ABSTRACT

The lighted surgical access system is provided that includes a circumferential retractor/protector and a light emitter system attached thereto. The circumferential retractor/protector retracts and protects a patient's body opening while the light emitter system illuminates the internal surgical site, body cavity or body opening.

20 Claims, 40 Drawing Sheets

(51) Int. Cl.
*A61B 1/313* (2006.01)
*A61B 17/34* (2006.01)
*A61B 90/30* (2016.01)

(52) U.S. Cl.
CPC .......... *A61B 17/3423* (2013.01); *A61B 90/30* (2016.02); *A61B 2090/306* (2016.02)

(56) References Cited

U.S. PATENT DOCUMENTS 5,522,791 A 6/1996 Leyva
5,810,721 A 9/1998 Mueller et al.
5,865,729 A * 2/1999 Meehan ................. A61B 17/42 600/245
5,906,577 A 5/1999 Beane et al.
6,048,309 A 4/2000 Flom et al.
6,077,288 A * 6/2000 Shimomura ....... A61B 17/3462 606/186
6,142,935 A 11/2000 Flom et al.
6,142,936 A 11/2000 Beane et al.
6,162,172 A 12/2000 Cosgrove et al.
6,352,531 B1 3/2002 O'Connor et al.
6,409,391 B1 6/2002 Chang
6,428,473 B1 8/2002 Leonard et al.
6,440,063 B1 8/2002 Beane et al.
6,464,406 B1 10/2002 Yarita et al.
6,497,654 B1 12/2002 Leonard et al.
6,504,985 B2 1/2003 Parker et al.
6,626,582 B2 9/2003 Farrar et al.
6,814,700 B1 11/2004 Mueller et al.
6,902,541 B2 * 6/2005 McNally ............. A61J 15/0042 604/32
6,939,296 B2 9/2005 Ewers et al.
7,008,377 B2 3/2006 Beane et al.
7,066,931 B2 6/2006 O'Connor et al.
7,182,524 B2 2/2007 Kramer et al.
7,223,233 B2 5/2007 Branch et al.
7,510,524 B2 3/2009 Vayser et al.
7,645,275 B2 1/2010 O'Connor et al.
7,703,987 B2 4/2010 Kramer et al.
7,758,500 B2 7/2010 Boyd et al.
7,901,353 B2 3/2011 Vayser et al.
7,909,761 B2 3/2011 Banchieri et al.
7,955,257 B2 6/2011 Frasier et al.
7,959,651 B2 6/2011 Branch et al.
8,088,066 B2 1/2012 Grey et al.
8,105,236 B2 1/2012 Malandain et al.
8,162,824 B2 4/2012 Vayser et al.
8,282,677 B2 10/2012 O'Connor et al.
8,303,497 B2 11/2012 Aferzon
8,317,693 B2 11/2012 Grey et al.
8,409,089 B2 4/2013 Michaeli et al.
8,430,813 B2 4/2013 Selover et al.
8,454,504 B2 6/2013 Michaeli et al.
8,480,566 B2 7/2013 Farr
8,550,993 B2 10/2013 Aferzon
8,636,658 B2 1/2014 Su et al.
8,641,608 B2 2/2014 Voegele et al.
8,663,102 B2 3/2014 Michaeli et al.
8,684,577 B2 4/2014 Vayser
8,708,896 B2 4/2014 Vayser et al.
8,864,662 B2 10/2014 Grey et al.
9,005,115 B2 4/2015 Vayser
9,060,707 B2 6/2015 Grey et al.
9,072,455 B2 7/2015 Vayser et al.
9,072,501 B2 7/2015 Menchaca et al.
9,161,820 B2 10/2015 Mark et al.
9,186,175 B2 11/2015 Mark et al.
9,216,015 B2 12/2015 Wilson
9,254,126 B2 2/2016 Frasier et al.
9,265,523 B2 2/2016 Mark et al.
9,271,637 B2 3/2016 Farr
9,282,878 B2 3/2016 Grey et al.
9,357,987 B2 6/2016 Aferzon
9,381,012 B2 7/2016 Su
9,386,974 B2 7/2016 Wilson
9,387,010 B2 7/2016 Mark et al.
9,468,366 B2 10/2016 Grey et al.
9,480,855 B2 11/2016 DiMauro et al.
9,504,373 B2 11/2016 Vayser et al.
9,579,121 B2 2/2017 Mark et al.
9,615,884 B2 4/2017 Armour et al.
9,622,777 B2 4/2017 Mark et al.
9,757,147 B2 9/2017 Mark et al.
9,770,261 B2 9/2017 Mark et al.
9,907,545 B2 3/2018 Galloway et al.
9,949,730 B2 4/2018 Hart et al.
9,968,414 B2 5/2018 Wilson
9,968,415 B2 5/2018 Wilson
9,986,901 B2 6/2018 Grey et al.
10,085,649 B1 10/2018 Valko et al.
10,088,638 B2 10/2018 Yajima
10,098,626 B2 10/2018 Gharibi Loron
10,105,042 B2 10/2018 Davis et al.
10,143,366 B2 12/2018 Mark et al.
10,172,514 B2 1/2019 Davis et al.
10,172,525 B2 1/2019 Davis et al.
10,307,183 B2 6/2019 Mark et al.
10,349,927 B2 7/2019 Galloway et al.
10,349,930 B2 7/2019 DiMauro et al.
10,376,281 B2 8/2019 Davis et al.
10,398,318 B2 9/2019 Davis et al.
10,405,941 B2 9/2019 Grey et al.
10,413,169 B2 9/2019 Davis et al.
10,449,340 B2 10/2019 Mark et al.
2005/0090717 A1 * 4/2005 Bonadio ............ A61B 17/0293 600/208
2005/0171408 A1 8/2005 Parker
2005/0209510 A1 9/2005 Bonadio et al.
2006/0161049 A1 * 7/2006 Beane ................ A61B 17/0293 600/207
2006/0247500 A1 * 11/2006 Voegele ............. A61B 17/0218 600/208
2007/0100210 A1 5/2007 Selover et al.
2007/0100211 A1 * 5/2007 Selover .................. A61B 17/02 600/199
2008/0319432 A1 12/2008 Ely et al.
2009/0118587 A1 5/2009 Voegele et al.
2010/0081881 A1 * 4/2010 Murray ............. A61B 17/3498 600/203
2010/0261972 A1 * 10/2010 Widenhouse ...... A61B 17/3462 600/206
2010/0261975 A1 * 10/2010 Huey ................. A61B 17/3462 600/208

(56) References Cited

U.S. PATENT DOCUMENTS

2011/0118553 A1 5/2011 Stopek
2011/0257488 A1 10/2011 Koyama et al.
2012/0041268 A1 2/2012 Grey et al.
2012/0101341 A1 4/2012 Malandain et al.
2012/0289816 A1 11/2012 Mark et al.
2013/0012770 A1* 1/2013 Su ..................... A61B 17/0293 600/104
2013/0032628 A1 2/2013 Li et al.
2013/0217975 A1 8/2013 Selover et al.
2014/0039265 A1 2/2014 Aferzon
2014/0153278 A1 6/2014 Vayser
2014/0343366 A1* 11/2014 Coe .................... A61B 17/0293 600/205
2015/0157307 A1 6/2015 Su
2015/0173596 A1 6/2015 Vayser
2016/0128722 A1 5/2016 Mark et al.
2016/0220240 A1* 8/2016 Hart ..................... A61B 1/0684
2016/0270816 A1* 9/2016 Mather .................. A61B 90/30
2016/0324402 A1 11/2016 Yajima
2017/0035275 A1 2/2017 Yajima et al.
2017/0042525 A1* 2/2017 DiMauro ............. A61N 5/0601
2017/0095310 A1 4/2017 Vayser et al.
2017/0095311 A1 4/2017 Vayser et al.
2017/0100022 A1 4/2017 Vayser et al.
2017/0100023 A1 4/2017 Vayser
2017/0224206 A1 8/2017 Vayser
2017/0265734 A1 9/2017 Vayser
2017/0367731 A1 12/2017 Mark et al.
2018/0021032 A1 1/2018 DiMauro et al.
2018/0064322 A1 3/2018 Klubben, III et al.
2018/0085141 A1* 3/2018 Wood ..................... A61B 90/30
2018/0206882 A1 7/2018 Davis et al.
2018/0249902 A1 9/2018 Grey et al.
2019/0000435 A1* 1/2019 Galloway ............ A61B 5/0538
2019/0053826 A1 2/2019 Bush, Jr. et al.
2019/0099070 A1 4/2019 Mark et al.
2019/0117254 A1 4/2019 Mark et al.
2019/0133433 A1 5/2019 Davis et al.
2019/0167246 A1 6/2019 DiMauro et al.
2019/0200853 A1 7/2019 Alvarez Gallego et al.
2019/0239923 A1 8/2019 Mark et al.

FOREIGN PATENT DOCUMENTS

WO WO 2012/159117 A1 11/2012
WO WO 2017/151754 A1 9/2017
WO WO 2019/215354 A1 11/2019

OTHER PUBLICATIONS

The International Bureau of WIPO, International Preliminary Report on Patentability for International Application No. PCT/US2021/54312, entitled "Lighted Surgical Access System," dated Apr. 20, 2023, 6 pgs.

* cited by examiner

FIG. 2
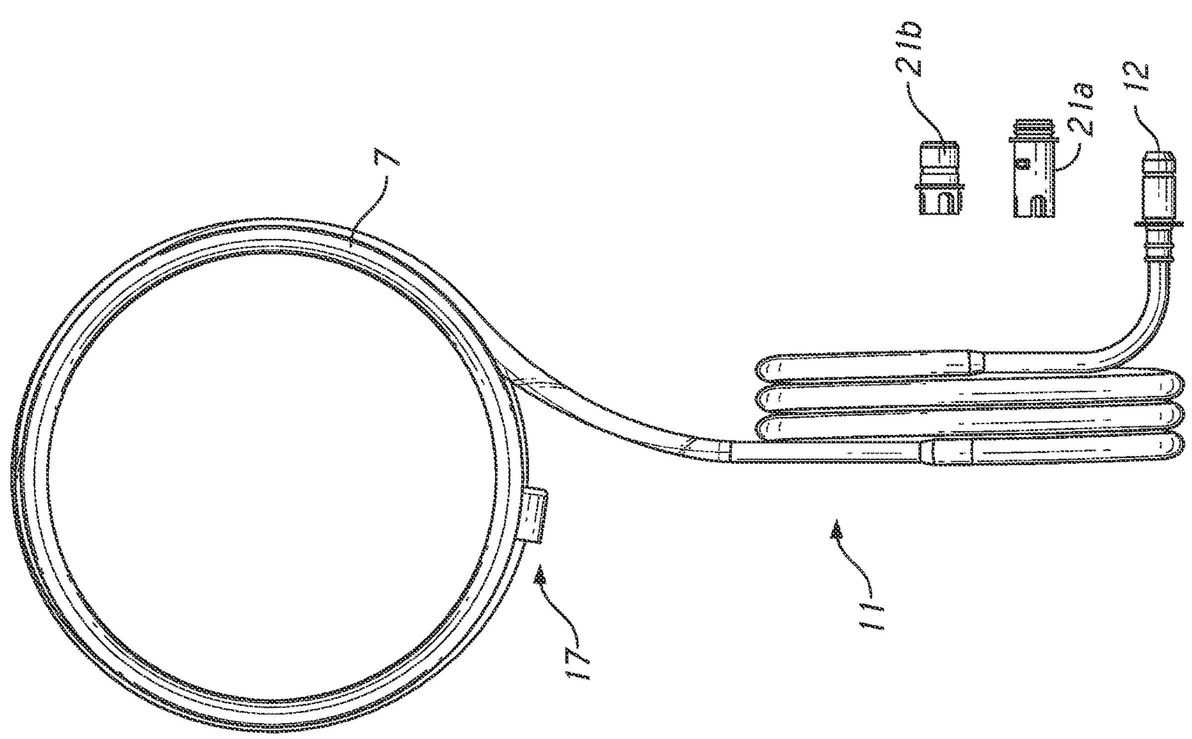

16
7
5
9
3
11

14
9
7
16
8

12
21c
27
25

LIGHTED SURGICAL ACCESS SYSTEM

CROSS-REFERENCE TO RELATED APPLICATIONS

This application is a U.S. National Phase application under 35 U.S.C. § 371 of PCT Application No. PCT/US2021/54312, filed Oct. 8, 2021, which claims priority to and benefit of U.S. Provisional Patent Application Ser. Nos. 63/089,486, filed on Oct. 8, 2020 and 63/248,319, filed on Sep. 24, 2021, all of which are incorporated herein by reference in their entirety.

BACKGROUND

The present application is generally directed to systems and methods for illuminating a surgical site and more particularly, lighted circumferential protectors-retractors and systems and methods thereof for illuminating internal surgical sites.

Proper illumination of a surgical site facilitates a surgical procedure, assisting the surgeon or medical personnel in the placement and operation of surgical instruments within the limited space confines of a patient's body cavity. Overhead surgical lamps are ubiquitous in operating rooms but are limited in providing effective illumination largely because of their positioning far outside the surgical site (e.g., incision or patient opening). Also, as the light comes from a limited direction, e.g., only one or two directions, it is difficult to avoid casting shadows that limit the visibility of the surgical site. In addition, the area of illumination is not tightly focused, causing glare around the site and diminishing the visual contrast. The amount of light that can illuminate the internal anatomy or internal surgical site is also restricted by the size of the incision or opening, becoming extremely challenging to achieve sufficient lighting as the size of the incision or opening is diminished. The convenience of overhead lamps is further reduced by the need for frequent readjustment to find a proper angle, especially when a surgical procedure requires repositioning of the patient.

Surgical headlamps suffer from many of the same drawbacks, including the problem of casting shadows from a unidirectional light, glare around the incision, and limited light entering the incision or opening. Such lamps can also be inconvenient as they are often bulky or require continuous concentration to keep the light properly directed. Lighted single point retractors aim to solve some of the problems with the ineffectiveness of overhead lights and headlamps, though they sacrifice some convenience because they must be held by hand. These lighted retractors also fail to provide circumferential illumination to the surgical site. Furthermore, such devices often provide unidirectional light without being able to illuminate deeply inside the patient's cavity. Additionally, often the direction of the light beams cannot be adjusted without losing traction. Other lighting systems fail to account for or overcome the challenges of obstruction from surrounding tissue or the device itself along with thermal, luminescence output or other similar performance, manufacturing and procedural issues.

SUMMARY

In accordance with various embodiments, a lighted surgical access system is provided. The lighted surgical access system comprises a circumferential protector and a light emitter system. In various embodiments, the circumferential protector comprises an outer ring, an inner ring, a sheath, or any combination thereof. In various embodiments, the light emitter system comprises a light emitting diode, a plastic optical fiber, an optical fiber or a light generator connectable to a laparoscope.

In accordance with various embodiments, a lighted surgical access system further comprises a light skirt attachable to the sheath, the light skirt comprises a hoop circumferentially disposed around an outer periphery of the sheath and movable longitudinally relative to the sheath. In various embodiments, at least one elongate light strand extends from the hoop and arranged to emit light away from the inner ring.

In accordance with various embodiment, a lighted surgical access system further comprises a flexible hoop attachable to the outer ring. In various embodiments, at one flange extends from the flexible hoop. In accordance with various embodiment, a lighted surgical access system further comprises a curved support attachable only to a section of the outer ring leaving portions along the outer ring free of any such support. In various embodiments, at least one flange is connected to and extendable from the curved support. In accordance with various embodiment, a lighted surgical access system further comprises a cap or flange removably connectable to the outer ring and a plurality of light emitters, each light emitter being adjustable in position relative to the cap or flange and independently adjustable relative to each other.

In accordance with various embodiments, a lighted surgical access system further comprises a light clip removably attached to the outer and/or inner ring. In various embodiments, a malleable neck arranged to be bendable and extendable from the light clip. In accordance with various embodiments, a lighted surgical access system further comprises a cap removably connected to the outer ring, the cap including one or more apertures through which one or more light bands extend therethrough and distally towards the inner ring. In accordance with various embodiments, a lighted surgical access system further comprises an inner curved support or light clip removably connected to the inner ring with the inner curved support comprising a light emitting diode incorporated within the inner curved support. In accordance with various embodiments, a lighted surgical access system further comprises a net lighting extending across the access channel and attached to the inner ring. In accordance with various embodiments, a lighted surgical access system further comprises an inflatable balloon attached to the sheath or the inner ring and wherein the light emitter system is attached to or integrated into the balloon. In accordance with various embodiments, a lighted surgical access system further comprises an instrument guard and wherein the light emitter system is attached or integrated into the instrument guard.

In accordance with various embodiments, a lighted surgical access system comprises an outer ring, an inner ring and a sheath having a proximal end connected to the outer ring arranged to be placed outside of a body cavity or externally to an internal surgical site and a distal end connected to the inner ring arranged to be placed inside of a body cavity or proximal to an internal surgical site. The sheath delimits an access channel extending from the outer ring to the inner ring. The lighted surgical access system comprises a light emitter comprising a light emitting diode, a light generator and a POF. The light generator is connectable to the POF, a laparoscope or both. Light is provided by or to the various embodiments by a light emitter system connectable there to and comprising one or more light sources, carriers, emitters or the like, including but not limited to, light boxes, LEDs, POFs and any various equivalents or combinations thereof integrated therein or attached thereto.

Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be understood by reference to the following description, taken in connection with the accompanying drawings in which the reference numerals designate like parts throughout the figures thereof.

FIG. 2 is a bottom view of a lighted surgical access system in accordance with various embodiments of the present invention.

DETAILED DESCRIPTION

Figure 1:
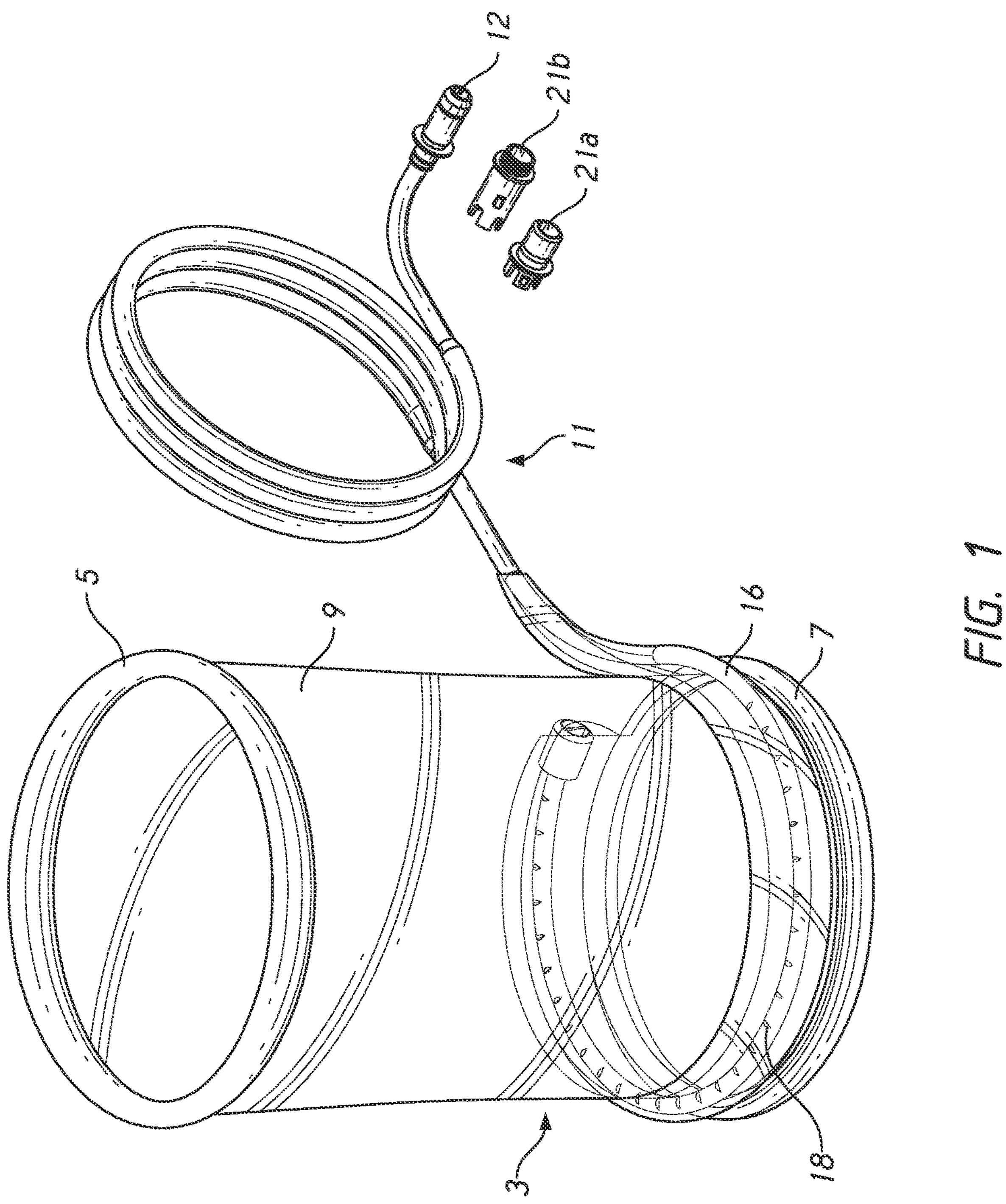
FIG. 1 is a perspective view of a lighted surgical access system in accordance with various embodiments of the present invention.
Figure 3:
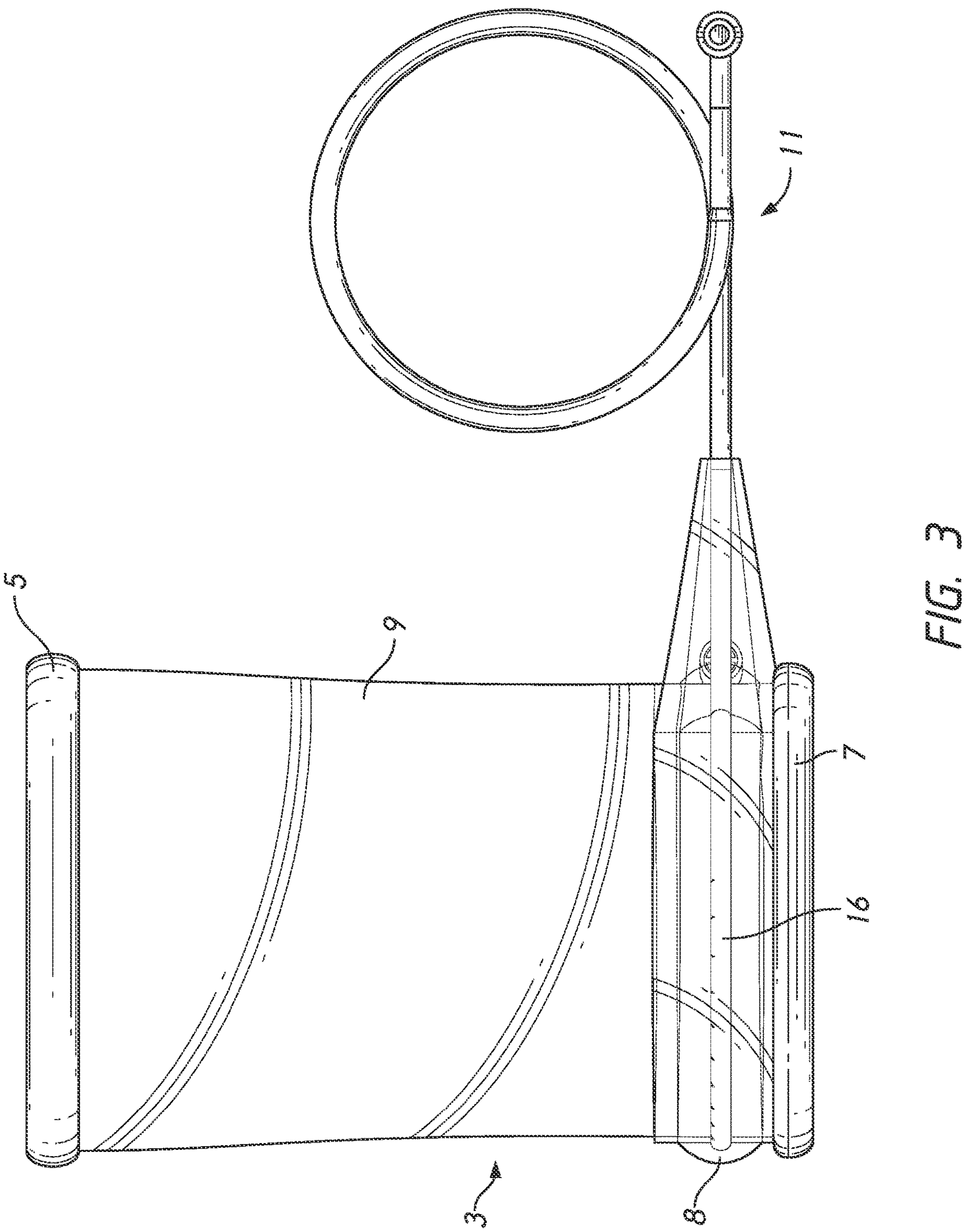
FIGS. 3-4 are side views of a lighted surgical access system in accordance with various embodiments of the present invention.
Figure 4:
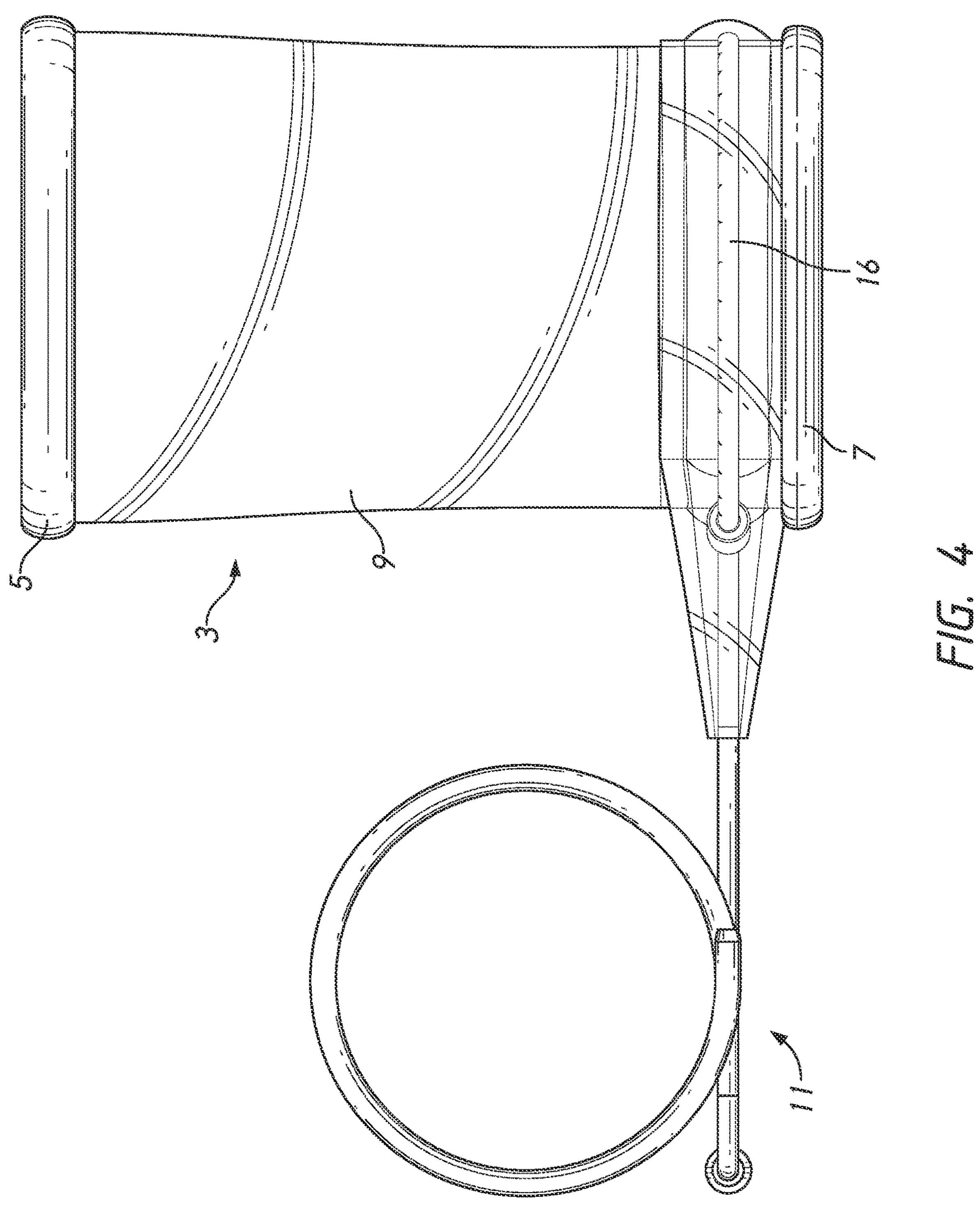

In accordance with various embodiments, lighted surgical access systems are provided, and various views of various embodiments of exemplary lighted surgical access systems and aspects thereof are shown in FIGS. 1-43. The lighted surgical access system, in various embodiments, includes a protector/retractor 3 (hereinafter referred to as "retractor") providing circumferential or 360 degrees of protection and/or retraction of an opening or orifice of a patient. The lighted surgical access system creates and thus provides unobstructed and illuminated access into a patient's body or cavity. The retractor comprises an outer ring or support 5 and an inner ring or support 7. The inner and outer rings are connected by a film, fabric, membrane or sheath 9. The retractor is adjustable in length by rolling the sheath around the outer ring and such adjustment can apply a retraction or radial force to retract or enlarge an opening in a patient. The retractor in various embodiments is adjustable in length or otherwise adjustable to accommodate different patient body types or body wall thickness. In various embodiments, the retractor has a fixed or predetermined length and/or is not adjustable in length by rolling the outer ring or other similar arrangements. The outer ring 5 is configured to be placed outside of the patient for ease of accessibility, adjustment of the retraction force and/or placement of the lighted surgical access system. In various embodiments, the sheath defines a working or access channel extending from its proximal end to its distal end and the lighted surgical access system provides unobstructed and illuminated access along and/or within the access channel defined by a sheath 9.

The retractor is sufficiently flexible to be atraumatic when the retractor is deployed or otherwise placed through and disposed in the opening of the patient. In various embodiments, the outer diameter or periphery of the retractor in operation and/or, as deployed, is delimited or is no larger than the outer diameter of the inner and/or outer rings. In various embodiment, the sheath 9 is made of an elastomeric or non-metallic material to be atraumatic and/or not or minimally thermally conductive when the retractor is in operation or deployed or otherwise placed through and disposed in the opening of the patient. In various embodiments, the sheath is made of one or more layers of material and in various embodiments is anisotropic, e.g., stretchable or extendable longitudinally but not or minimally radially, being made of or including one or more layers of a fabric or similar materials with such anisotropic characteristics.

Connected to a distal portion of the sheath 9 of the retractor is a light carrier, e.g., a plastic optical fiber (POF) 11. In various embodiments, the POF 11 is an elongate tube or tubular-like structure and/or having a core covered or encased in an outer cladding. The POF 11 has a distal portion attached to the distal portion of the sheath and for ease of readability is herein referred to as "POF tail" 16. The POF 11 also has a proximal portion configured to extend from the POF tail 16 or an intermediary portion therebetween. The proximal portion of the POF, for ease of readability, is herein referred to as "POF leader" 14. The POF tail or portions thereof is coupled to the sheath 9 of the retractor. In various embodiments, the POF tail or portions thereof is coupled to the sheath 9 by a sleeve 8.

As illustrated, in various embodiments, the POF 11 is attached to the sheath 9 of the retractor via a sleeve 8. The sleeve 8 in various embodiments surrounds all or at least a portion of an outer periphery of a distal portion of the sheath. The sleeve is configured to house a distal portion of the POF or the POF tail 16 and in various embodiments provides a channel in which the POF extends therethrough. The sleeve 8 in various embodiments is heat sealed on its proximal and distal portions relative to a longitudinal axis of the sheath enclosing and encompassing the POF. The sleeve 8 is configured to create a barrier to prevent blood or other foreign matter from entering the sleeve, obstructing the POF and/or absorbing the light emitted from the POF. In various embodiments, the sleeve 8 anchors the POF to the sheath 9 of the retractor and thus further assists in preventing the POF from being dislodged or otherwise removed from the sheath. The sleeve 8, in various embodiments, anchors the POF from independently moving lengthwise or longitudinally along the sheath or at least not beyond the confines of the sleeve. As such, in various embodiments, the sheath's placement determines the placement of the sleeve and thus the POF.

In various embodiments, the sleeve is embedded or otherwise integrated into the sheath 9 of the retractor. In various embodiments, the sheath includes at least two walls, e.g., an inner and outer wall, with the POF tail 16, sleeve 8 and/or portions thereof placed between the walls of the sheath. An opening to access and place the POF tail between the walls may be heat sealed or otherwise closed to prevent foreign matter from entering. In various embodiments, a seal 24 is place on one end of the sleeve 8 to prevent foreign matter from entering the seal and in various embodiments, the seal is placed between the POF tail 16 and the POF leader 14. Heat seals or the like below and/or above can be used to anchor the POF from independently moving lengthwise or longitudinally along the sheath or at least not beyond the confines of the sleeve. The heat seals may extend circumferentially around the sheath or only along one or more portions thereof. In various embodiments, the sleeve is made of one or more layers of material. In various embodiments, light output may be increased by covering the POF tail with a reflective material 22. The reflective material reflects escaping light back into the POF. In various embodiments, reflective material is place between the sleeve 8 and the sheath 9 or portions thereof. In various embodiments, reflective material is integrated with the sleeve 8 or portions thereof, e.g., an upper portion to further reflect down or distally and into an internal surgical site.

In various embodiments, a light generator or source is connectable to the POF. In various embodiments, the light generator or source is a light box 40, tower or the like configured to be connected to a laparoscope or endoscope. An endoscope may be connected to the light tower via a light cable 30 in which one end 31 is connected to the light tower and the other end 32 to the endoscope. As such, the light cable is configured to be connectable to a light tower or similar light source that is configured to supply light to a surgical laparoscope or endoscope. In various embodiments, the light source is provided by a surgical laparoscope or endoscope and/or its light source connected thereto. In various embodiments, the light source has a power supply or source and/or a controller to adjust the light output of the light source.

The light source being a source that supplies light to endoscope and laparoscope provides convenience to the user and eases operation of the lighted surgical access device, as such a source is often conveniently available in most surgical environments. Additionally, such sources also place electronic components and/or non-sterile components away from surgical site and can further provide the convenience of adjusting the light output of the light source and thus the POF connected thereto. It should however be appreciated that other sources of light may be provided or otherwise connected to the lighted surgical access device to supply light to the POF. As such, such described light sources should not be construed as limited but rather examples of a source of light for the POF. However, the light source either by itself or through other connections, adaptors, amplifiers, or the like provides sufficient lumens or light output to illuminate the internal surgical site and/or the access channel via the connected POF. In various embodiments, the light source is a Xeon light source, a 300-watt light source, generates a light output of at least 1500 lumens, or any combination thereof. In various embodiments, the light source comprises of one or more light emitting diodes ("LEDs"). In various embodiments, the light source, e.g., one or more LEDs or the like, is connectable to the light cable, a connector, an adaptor, the POF or any combination thereof. In various embodiments, the light source is battery powered.

In various embodiments, the lighted surgical access system includes one or more adapters or adaptors 21 and/or connectors 12 configured to provide a continuation between the POF and a light source, a light cable and/or an intermediary connection between the light source and/or the light cable. This continuation minimizes light loss and decreases the temperature experienced by the adaptor and/or connector as light is directly transferred from the light cable, source and/or intermediary to the POF without gaps or spaces, e.g., an air gap. In various embodiments, the continuation is provided by a flush or near flush contact or similar connections in which gaps or spaces between the POF and a light source, light cable and/or an intermediary connection between the light source and/or the light cable are minimized or eliminated. In various embodiments, the lighted surgical access system includes one or more adapters or adaptors 21 and/or connecters or connectors 12 configured to provide a flush or near flush contact between the POF and a light source, a light cable and/or an intermediary connection between the light source and/or the light cable.

In various embodiments, the adaptor and/or connector is made of plastic, metal or the like having high heat dissipation properties. In various embodiments, the adaptor and/or connector is made of or coated with a heat insulated material arranged to minimize heat transfer to other components, user and/or patient.

Figure 19:
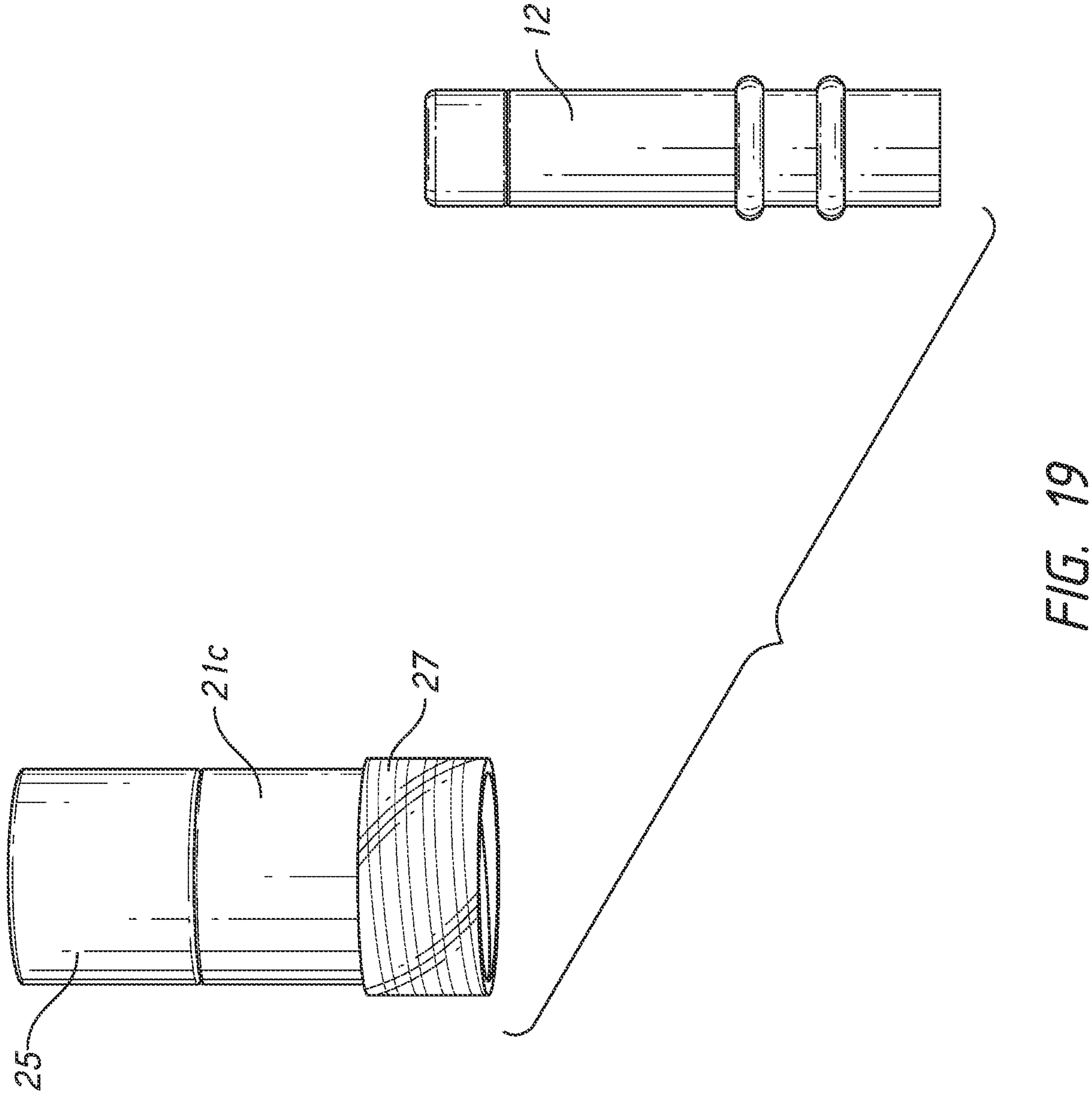
FIG. 19 are side views of an adaptor in accordance with various embodiments of the present invention.
Figure 20:
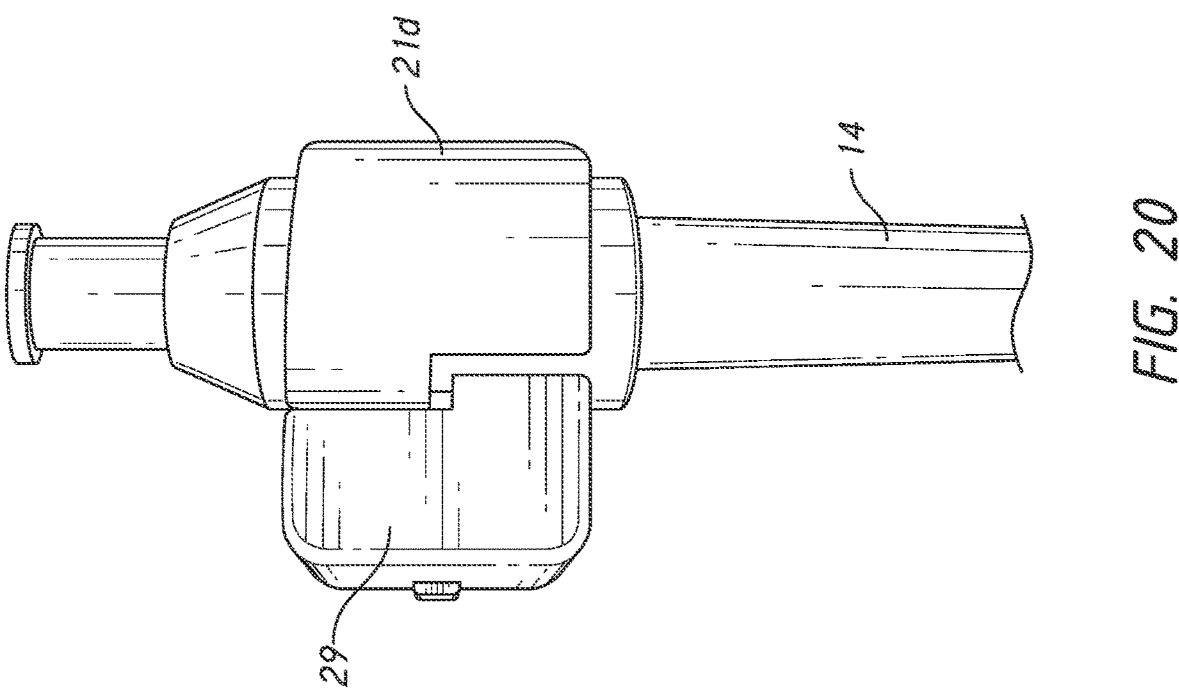
FIG. 20 is a side view of an adaptor in accordance with various embodiments of the present invention.
Figures 21A, 21B, 21C, 21D:
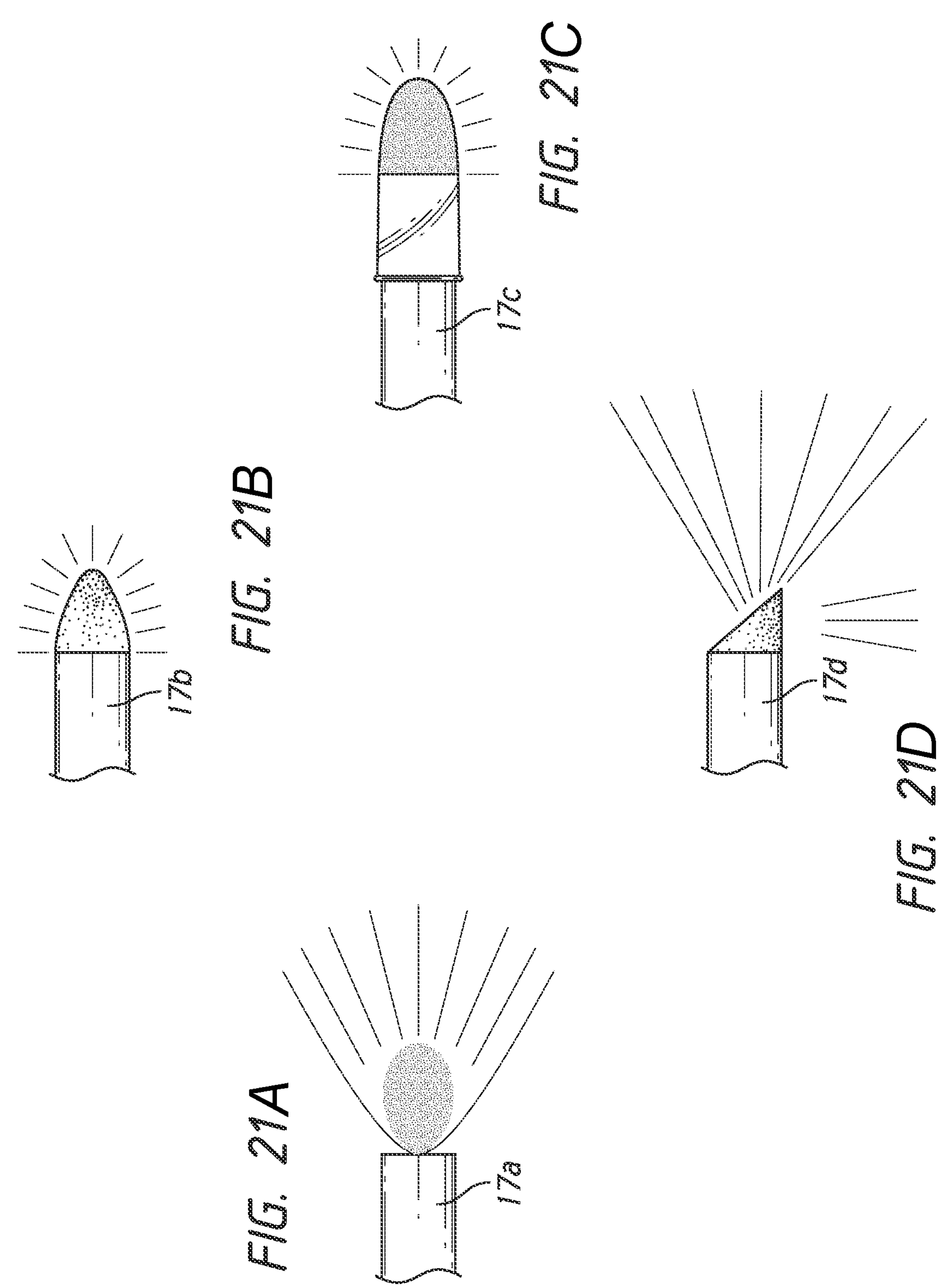
FIG. 21A is an end profile or cap of a plastic optical fiber in accordance with various embodiments of the present invention.
FIG. 21B is an end profile or cap of a plastic optical fiber in accordance with various embodiments of the present invention.
FIG. 21C is an end profile or cap of a plastic optical fiber in accordance with various embodiments of the present invention.
FIG. 21D is an end profile or cap of a plastic optical fiber in accordance with various embodiments of the present invention.

In various embodiments, the adaptor provides a user with the ability to interchange adaptor connection type based on their need and/or the available light cables, sources and/or intermediary connections. In various embodiments, the adaptor is interchangeable and/or double-sided. For example, as illustrated in FIG. 19, adaptor 21*c* is double-sided having one side 25 with an interface arranged to engage and secure with a first predetermined type or types of connections to light cables and/or light sources and an opposing or flip side 27 with an interface arranged to engage and secure with a second or different predetermined type or types of connections to light cables and/or light sources. Both sides 25, 27 of the adaptor 21*c* are arranged to engage and secure with the connector 12 of the POF 11. In various embodiments, sides 25, 27 connects and secures the adaptor to respective connections through threads, clips, snap-fits, keyways, bayonets or other various interfaces or interfacing features. An adaptor in various embodiments connects with a fixed ACMI adaptor using threads or snap on features. In various embodiments, the connector and/or adaptor, e.g., adaptor 21*d*, includes levers or arms, e.g., arm 29, configured to enlarge or retract an inner diameter or opening to open/close or clamp around a connection or end of the light source, light cable, and/or an intermediary connection, e.g., an adaptor or additional cables. In various embodiments, one end of the adaptor and/or connector has an adjustable opening or clamp interface, e.g., adaptor 21*d* as shown in FIG. 20, and in other various embodiments, the adaptor and/or connector has both ends with adjustable openings or clamp interfaces. In various embodiments, the adaptor 21 can be integrated or otherwise permanently attached to the connector 12 as a monolithic structure or can replace or be used in place of the connector 12.

In various embodiments, the end of the light cable is configured to be removably attached to a laparoscope or the connector of the lighted surgical access device. In various embodiments, the connector and/or adaptor is configured to removably connect directly to a light source. In various embodiments, the connector and/or adaptor is configured to removably connect to a light cable. In various embodiments, the connector is provided to specifically attach to a specific connection presented at the end of the light cable. In various embodiments, the connector and/or adaptor is customizable or adjustable to accommodate one or more different types of connectors or connections presented or offered at the end of the light cable. In various embodiments, the connector and/or adaptor is connectable and/or compatible with industry standard surgical light cables.

In various embodiments, the connector 12 has a snap-fit connection in which one or more adaptors, e.g., adaptor 21*a*, *b*, are arranged to snap onto an open end of the connector 12. In various embodiments, the connector 12 includes one or more O-rings or snap rings with corresponding grooves or channels configured to seal and engage the inner diameter of the adaptor to further enhance the connection between the two. In various embodiments, the connector 12 and/or adaptor 21 includes one or more flanges extending radially from the outer surface of the connector and/or adaptor to prevent or restrict the travel or extension of the adaptor or a connection or connector thereto over the connector 12 and/or adaptor 21. In various embodiments, the adaptor has similar connection type ends. For example, adaptor 21*a* has a snap fit connection on one end and a snap fit connection on the opposite end. In various embodiments, the adaptor has dissimilar connection type ends. For example, adaptor 21*b* has a snap fit connection on one end and a threaded connection on the opposite end. In various embodiments, the connector 12 is used without the adaptor 21.

In various embodiments, the adaptor is arranged to press fit over the outer surface of different types of light cables. In various embodiments, the adaptor is arranged to connect or secure the connection and/or light cable via a magnetic connection. In various embodiments, the adaptor includes a friction-based push-lock where insertion of the light cable within an opening in the adaptor and the subsequent release of the light cable connects and secure the light cable to the adaptor. In various embodiments, the adaptor is arranged to connect directly to a connection on the light box or source. In various embodiments, the adaptor comprises of clam-shell-like components arranged to clamp and secure the light cable and the POF together. In various embodiments, the clamshell further comprises compressible foam or the similar materials or have different diameter tiers to fit and secure different sized or dimensioned and/or shaped light cables and/or their connectors or other intermediaries thereto. In various embodiments, the proximal end of the POF includes a preload or biasing mechanism, such as a spring or O-ring, arranged to engage an distal end of a light cable to compress, e.g., the spring, as the light cable is connected to the adaptor to bias the light cable and/or adaptor into a flush contact position. In various embodiments, the adaptor includes one or more lenses arranged to focus light from the light cable into the POF and/or connector and/or in various embodiments, the connector includes one or more lenses arranged to focus light from the adaptor into the connector and/or from the connector into the POF.

In various embodiments, the adaptor and/or connector includes a heat sink or other heat dissipation and/or insulation to reduce or minimize thermal effects that may occur due to non-flush contacts with the light cable, adaptor and/or connector. In various embodiments, the adaptor and/or connector includes an insulation sleeve arranged to reduce thermal effects and/or spread that may potentially adversely affect the user, patient, and/or the device or other surrounding device or components.

In various embodiments, the POF leader 14 communicates or transmits light from a proximal end or connector 12, in various embodiments, to the POF tail 16 and ultimately to the internal surgical site or body cavity or opening. In various embodiments, the POF leader is an elongate tube, tubular-like or cylindrical structure.

The POF leader 14, in various embodiments, is covered with heat shrink to eliminate glare, reduce bends, and/or to join or connect the connector and/or sleeve with the POF. The heat shrink or another opaque material serves as a barrier that blocks light escaping from the leader from causing glare. The heat shrink in various embodiments has a non-transparent color and/or includes or is made of non-translucent material.

In various embodiments, the POF leader 14 and/or POF tail 16 comprises a heat shrink that provides a layer of material constricting the POF and preventing sharp bends. Sharp bends in the POF can cause a substantial amount of light to be lost. To help anchor or seal the connector, adaptor and/or sleeve to the POF, in various embodiments, the heat shrink is used. It should be noted that the heat shrink eliminates glare, reduces bends, and joins the adaptor and/or connector with the POF, solving multiple problems at once. In various embodiments, the POF may be painted or coated to eliminate glare, stress releasers used to reduce bends, and/or clamps used to join or connect to the adaptor, connector or sleeve to separately or individually to reinforce the heat shrink or accomplish the task separately or individually.

In various embodiments, the POF leader 14 is configured to maintain flexibility to allow a user to manipulate the POF and avoid tissue trauma against the incision wall or interfere with the sheath of the retractor. In various embodiments, the POF leader is configured to prevent the POF from dislodging or shifting to maintain optimal light output or throughput between the light source and the POF. In various embodiments, the POF leader is configured to block light emitting from the POF until the light reaches the POF output site to thereby to maximize the illumination or reduction of delivered or communicated light at the site. In various embodiments, the POF leader includes opaque, e.g., black, film or lining that may or may not be heat shrunk that provides flexibility and light blockage. In various embodiments, select portions, e.g., the proximal and/or distal portions or ends of an opaque film, sleeve, wrap, or lining are heat shrunk onto the tube of the POF leader. In other embodiments, the POF leader is less opaque, e.g., white, with a film or lining that may or may not be heat shrunk that provides flexibility. In various embodiments, the POF leader comprises a black adhesive lined heat shrink that provides flexibility, resistance to pull force or dislodgement of the POF leader and light blockage. In various embodiments, light output may be increased by wrapping the POF leader with a reflective material before applying the heat shrink. The reflective material reflects escaping light back into the POF.

In various embodiments, the POF leader includes cuts, slits and/or scoring to act as cooling scores to reduce or dissipate some of the light energy entering the POF and prior to such energy reaching the POF tail. In various embodiments, cooling scores are provided under an opaque film, sleeve, wrap, or lining are heat shrunk onto the POF leader, e.g., a black adhesive lined heat shrink. In various embodiments, the opaque film, sleeve, wrap or lining are heat shrunk onto the POF leader, e.g., a black adhesive lined heat shrink, absorbs the light from the cooling scores and thereby allows heat energy to be dissipated across a larger surface area along the POF and not concentrated at the POF tail and/or the distal end or distal most end of the POF tail 16.

Figure 15:
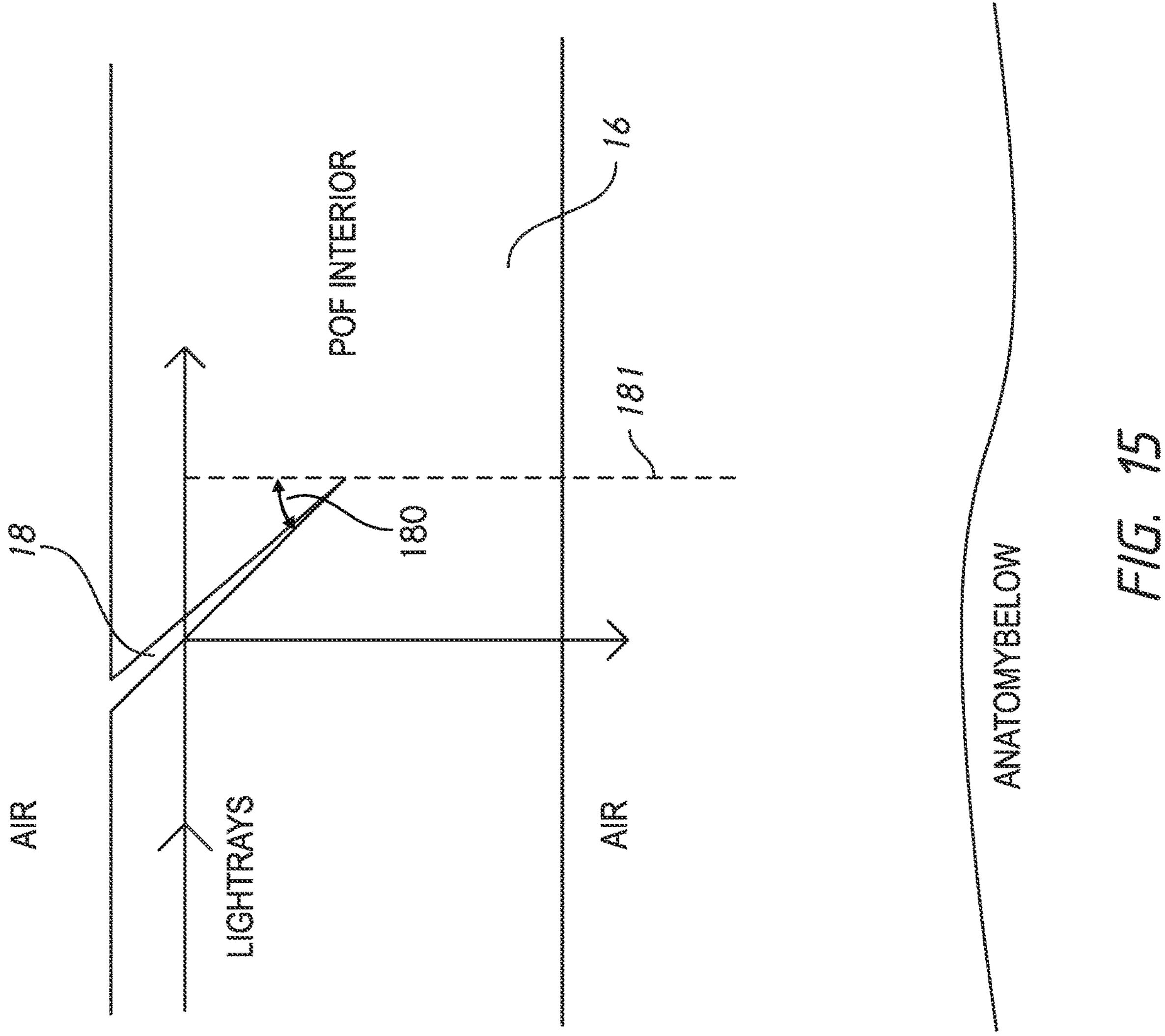
FIG. 15 is a graphical representation of a plastic optical fiber exemplifying a cut relative to incoming light and an internal surgical site in accordance with various embodiments of the present invention.
Figure 16:
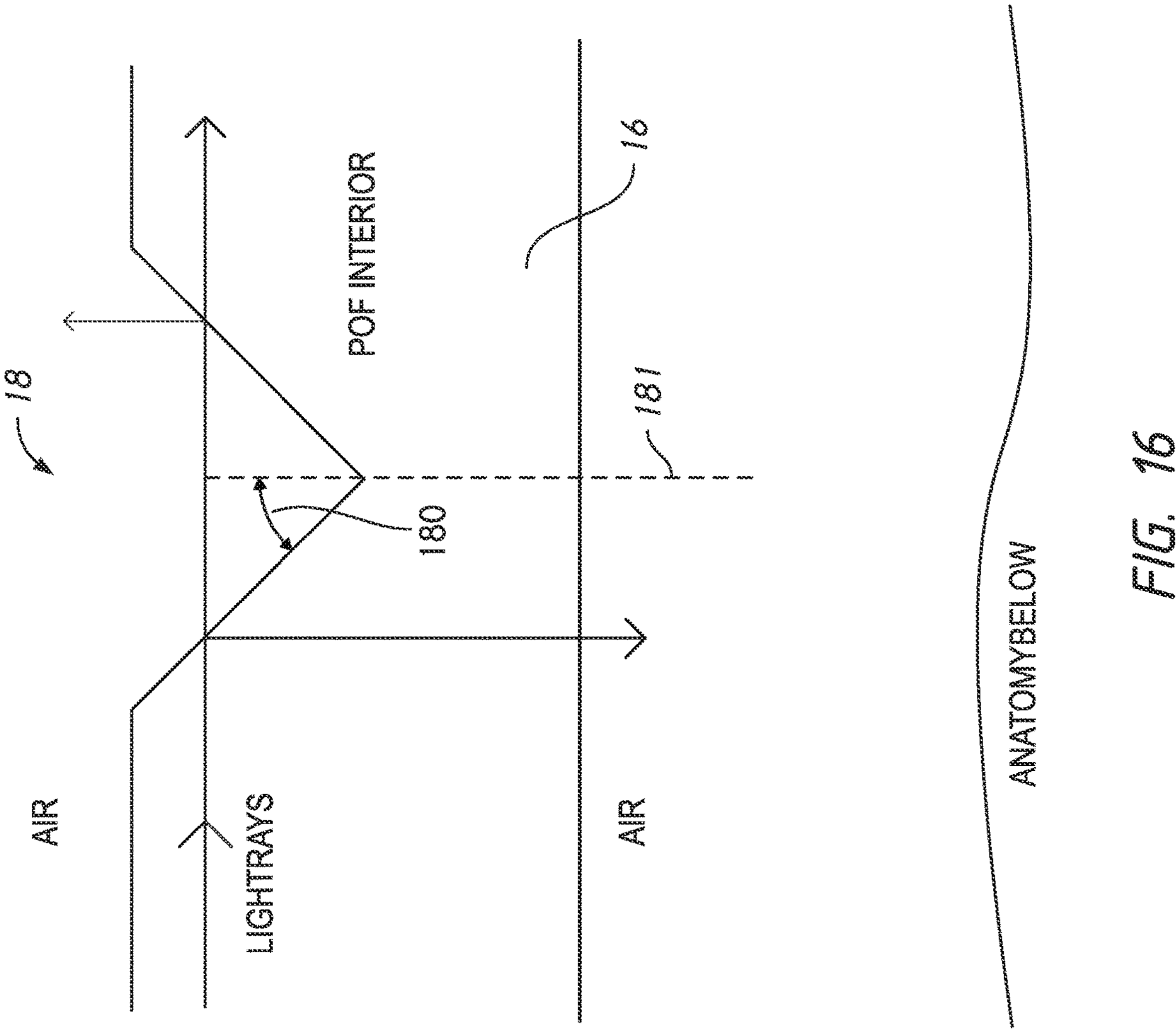
FIG. 16 is a graphical representation of a plastic optical fiber exemplifying a cut relative to incoming light and an internal surgical site in accordance with various embodiments of the present invention.
Figure 18:
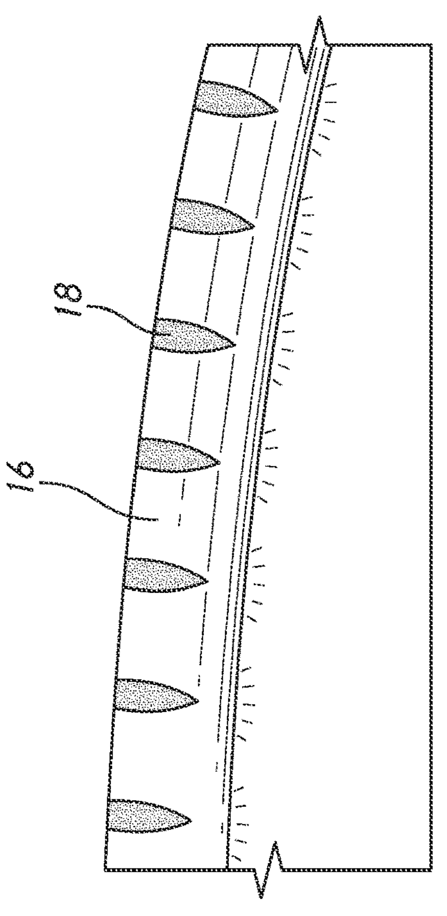
FIG. 18 is a top perspective view of a plurality of cuts or scoring in a plastic optical fiber in accordance with various embodiments of the present invention.
Figure 17:
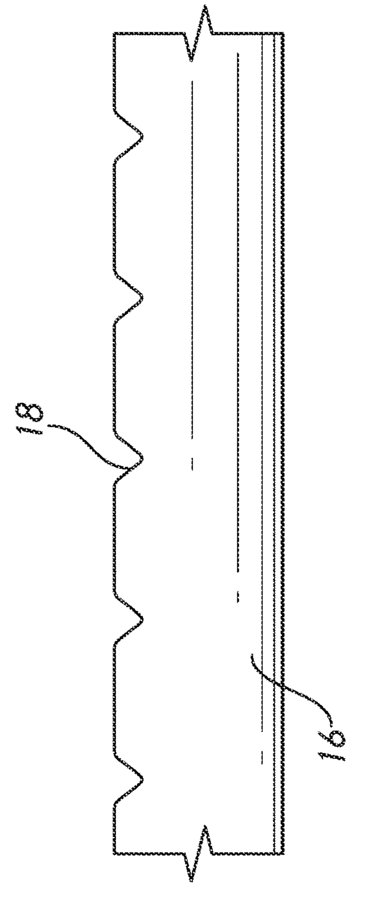
FIG. 17 is a side view of a plurality of cuts or scoring in a plastic optical fiber in accordance with various embodiments of the present invention.

In various embodiments, the POF tail 16 is configured to lie or be placed inside the surgical site. In various embodiments, the POF tail is an elongate tube or a tubular-like or cylindrical structure. In various embodiments, the POF tail comprises one or more cuts, scoring or indentations 18. The cuts 18 in various embodiments are angled at a predetermined or predefined angle, e.g., at or around 45 degrees, to ensure total internal reflection, for more than half of the light that encounters the cuts. In various embodiment, the scoring or cuts are angled between 42 to 45 degrees, e.g., angle 180 relative to axis 181 as shown in FIGS. 15-16. The light refracts out of the POF once it reaches the other side of the POF because the angle between the light rays and surface of the POF are large enough that light escapes instead of bouncing inside the POF. Reflecting light to the other side of the POF is beneficial because the cylindrical POF wall helps diffuse light. The cuts are positioned so that the refracted light is directed to the internal anatomy.

In various embodiments, the frequency or the number of the cuts 18 are predetermined or predefined to create an even extraction and distribution of light near the distal end of the sheath and/or at the internal surgical site. Each cut extracts light and decreases the amount of light traveling through the POF thus resulting in dimmer subsequent cuts. To compensate or account for the dimness, the frequency/amount of the cuts in various embodiments are predetermined such that light extraction is uniform throughout. In various embodiments, the one or more cuts are predetermined or predefined in spacing or positioning to create an even extraction and distribution of light near the distal end of the sheath and/or at the internal surgical site.

The cuts in various embodiments are on the surface or punched through the POF. Circular holes through the POF can achieve similar results as cuts. In various embodiments, the POF is scored to increase the brightness and/or light output at the surgical site about 10 times greater than bare POF or POF unscored. Additionally or alternatively, the POF is scored to reduce the power required to generate a desired light output and/or brightness and in various embodiments reduces power required to about 50 to 60 percent than that required by bare POF or POF unscored.

In various embodiments, the scoring of the POF 11 can vary in frequency and/or depth to vary the light output, focus and/or direction of the light at the surgical site, e.g., high-lighting or focusing on certain portions relative to the orientation of the retractor and the POF attached thereto.

As shown, for example, at least in FIGS. 21A-21D, the distal end 17 of the POF 11 may have a predefined or predetermined end profile, covering and/or cap. In various embodiments, the distal end 17 of the POF 11 has a flat end, profile or shape, e.g., a flat end 17*a*, and/or a cap, cover or lens with a flat end, shape or profile. The flat end 17*a* is configured to direct light from POF 11 directly in-line or longitudinally out the distal end 17 of the POF along a center axis of the POF. As such, the light of the POF exits unobstructed and is not reflected back into the POF. In various embodiments, the distal end 17 of the POF 11 has an angled end, shape or profile, e.g., angled end 17*d*, and/or a cap, cover or lens with an angled or slanted end, shape or profile. The angled end 17*d* is configured to direct light from POF 11 orthogonally or angled relative to a center or longitudinal axis of the POF and/or offset or parallel to the center axis of the POF.

In various embodiments, the end profile of the POF 11 is tapered or rounded to refract light radially. In various embodiments, the distal end 17 of the POF 11 has a tapered or rounded end, profile or shape and/or a cap, cover or lens with a tapered or rounded end, shape or profile, e.g., a tapered end 17*b* or rounded end 17*c*. For example, in various embodiments, instead of the light escaping parallel to the POF 11 it is distributed radially and thus illuminating the internal anatomy. Inside the POF 11, in various embodiments, light is traveling at +/−25 degrees to the POF center axis. In order to extract all of that light radially the end profile is tapered to +/−23 degrees. In various embodiments, a tapered profile of the POF extracts the light radially. In various embodiments, the distal portion or end of the POF has a profile or shape that is different from a distal end or portion of the cap, cover or lens of the POF. In various embodiments, the distal end 17 of the POF 11 has an end, profile or shape and/or a cap, cover or lens with an end, shape or profile of a different geometry other than flat, such as round or a prism, to direct or diffuse light for enhanced illumination, minimize light interference and/or reduce heat or thermal energy.

Figure 5:
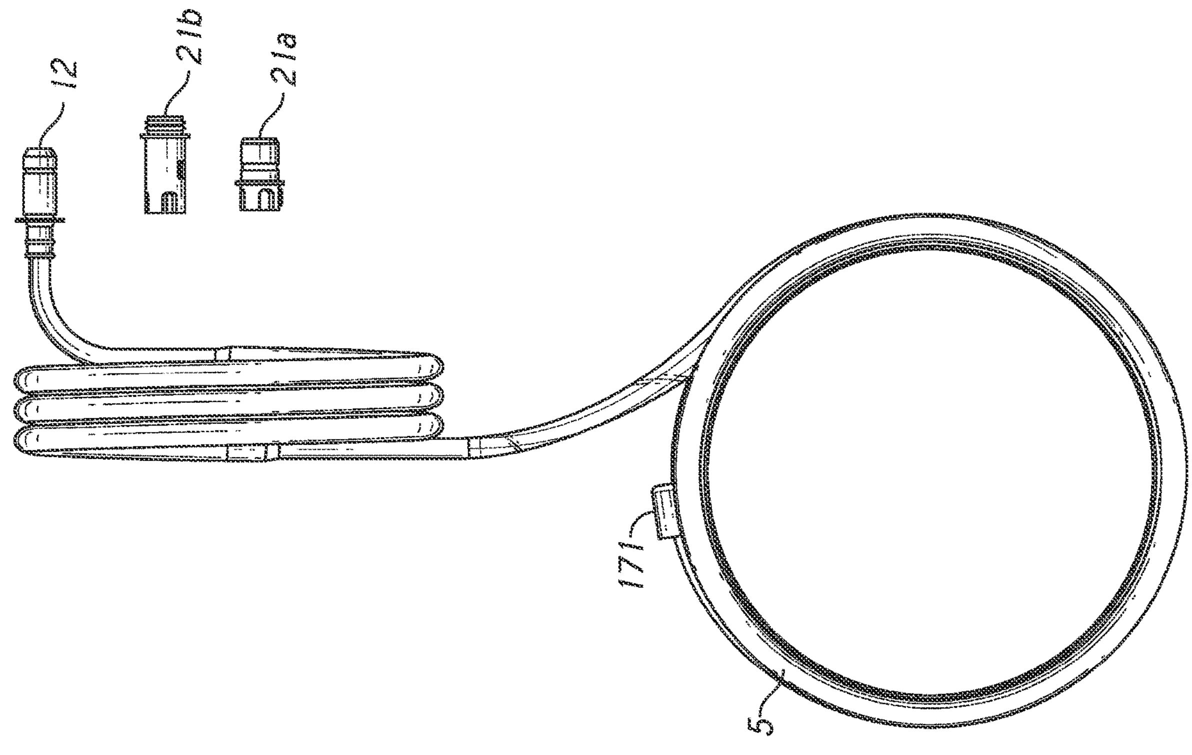
FIG. 5 is a top view of a lighted surgical access system in accordance with various embodiments of the present invention.
Figure 6:
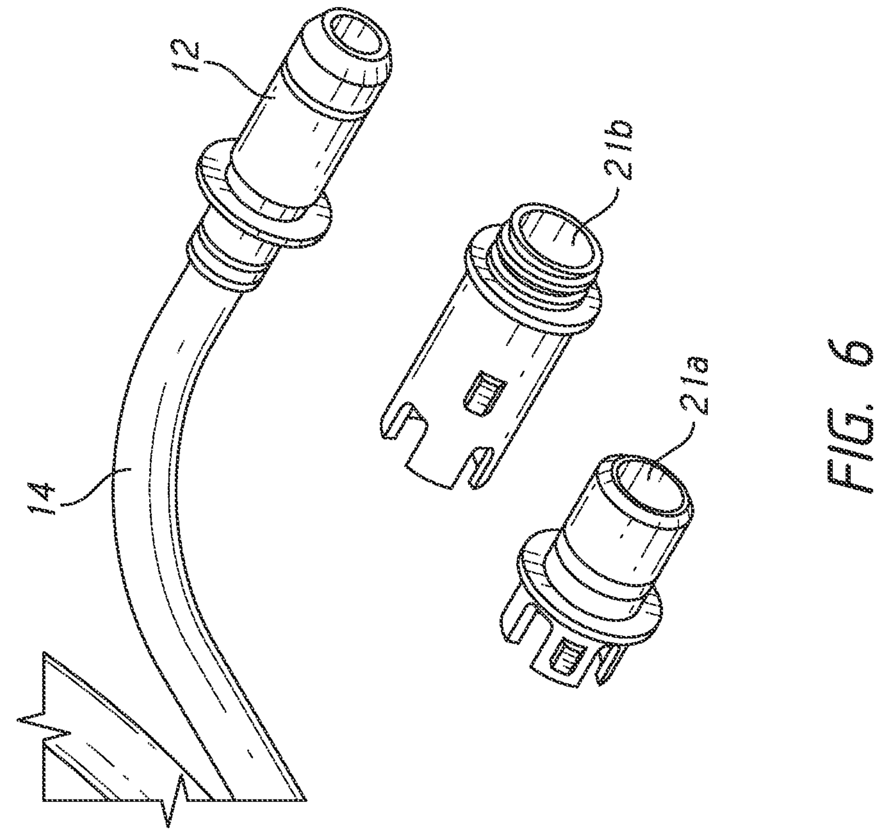
FIG. 6 is a perspective view of portions of a lighted surgical access system in accordance with various embodiments of the present invention.
Figure 7:
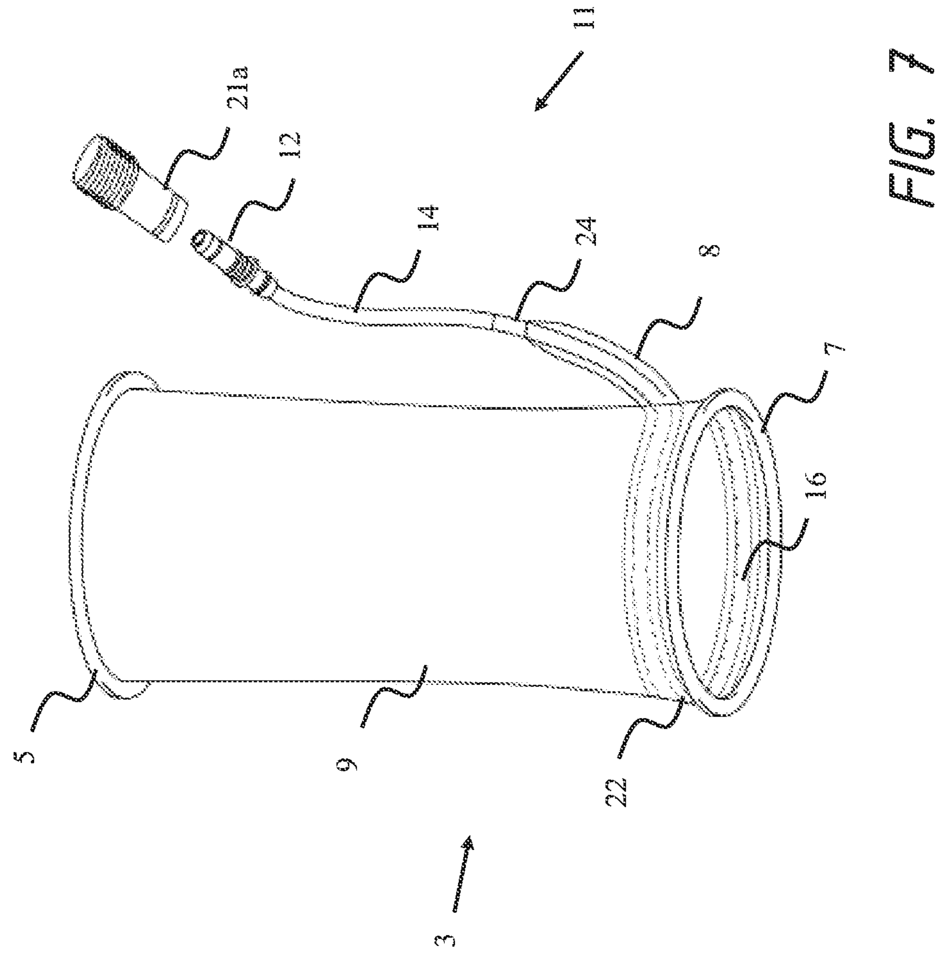
FIG. 7 is a perspective view of a lighted surgical access system in accordance with various embodiments of the present invention.
Figure 8:
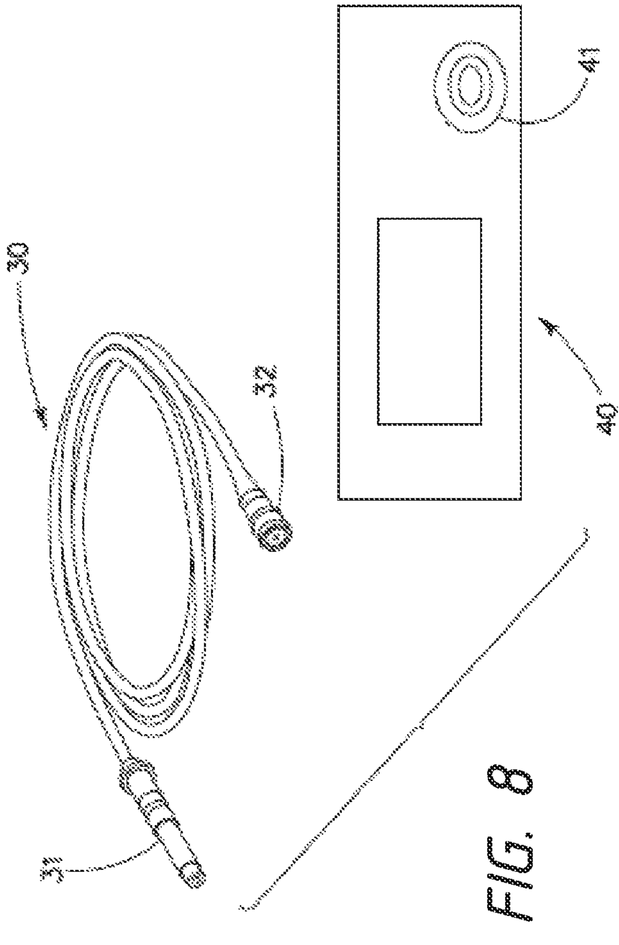
FIGS. 8-11 are perspective views of portions of a lighted surgical access system in accordance with various embodiments of the present invention.
Figure 9:
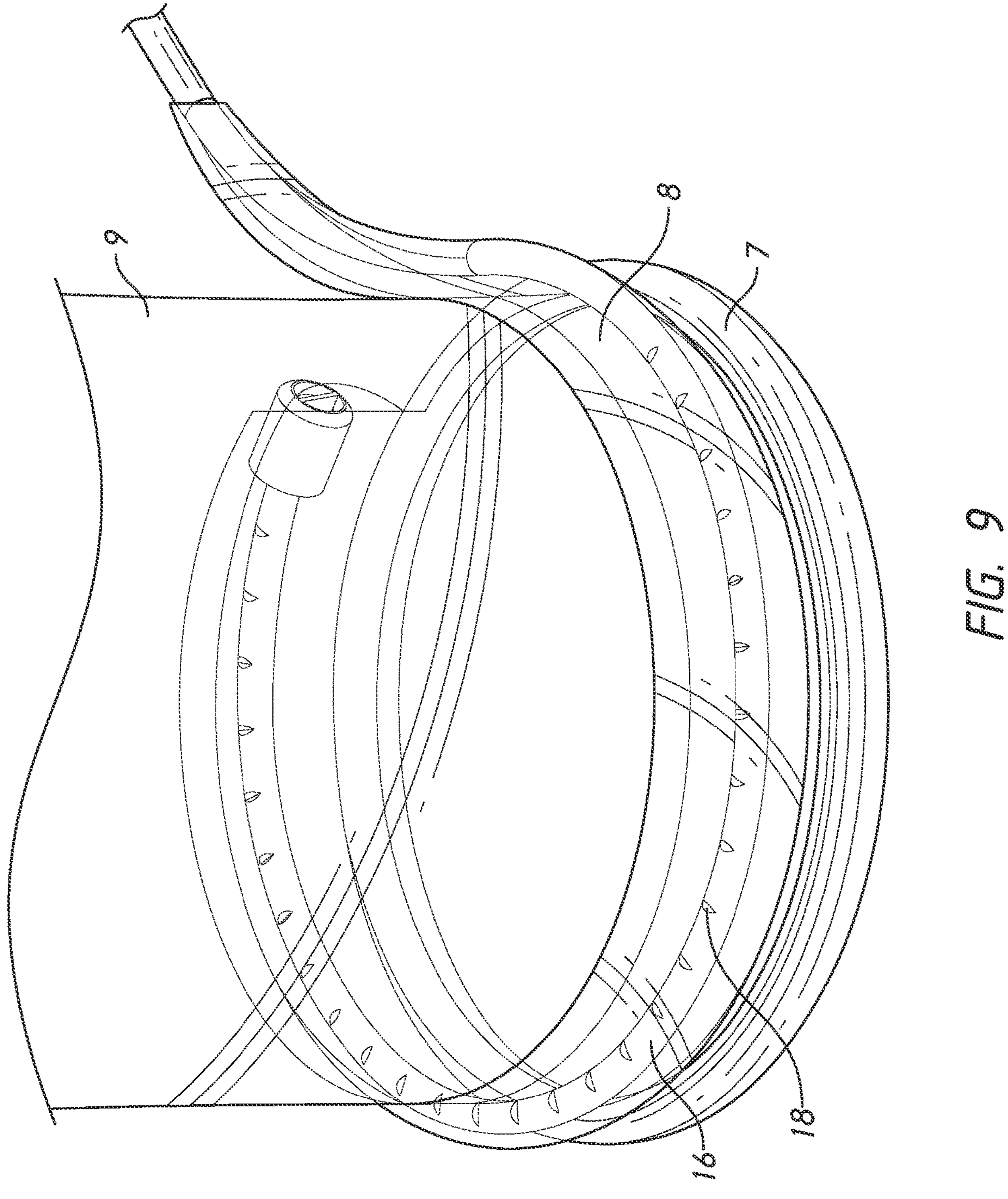
Figure 10:
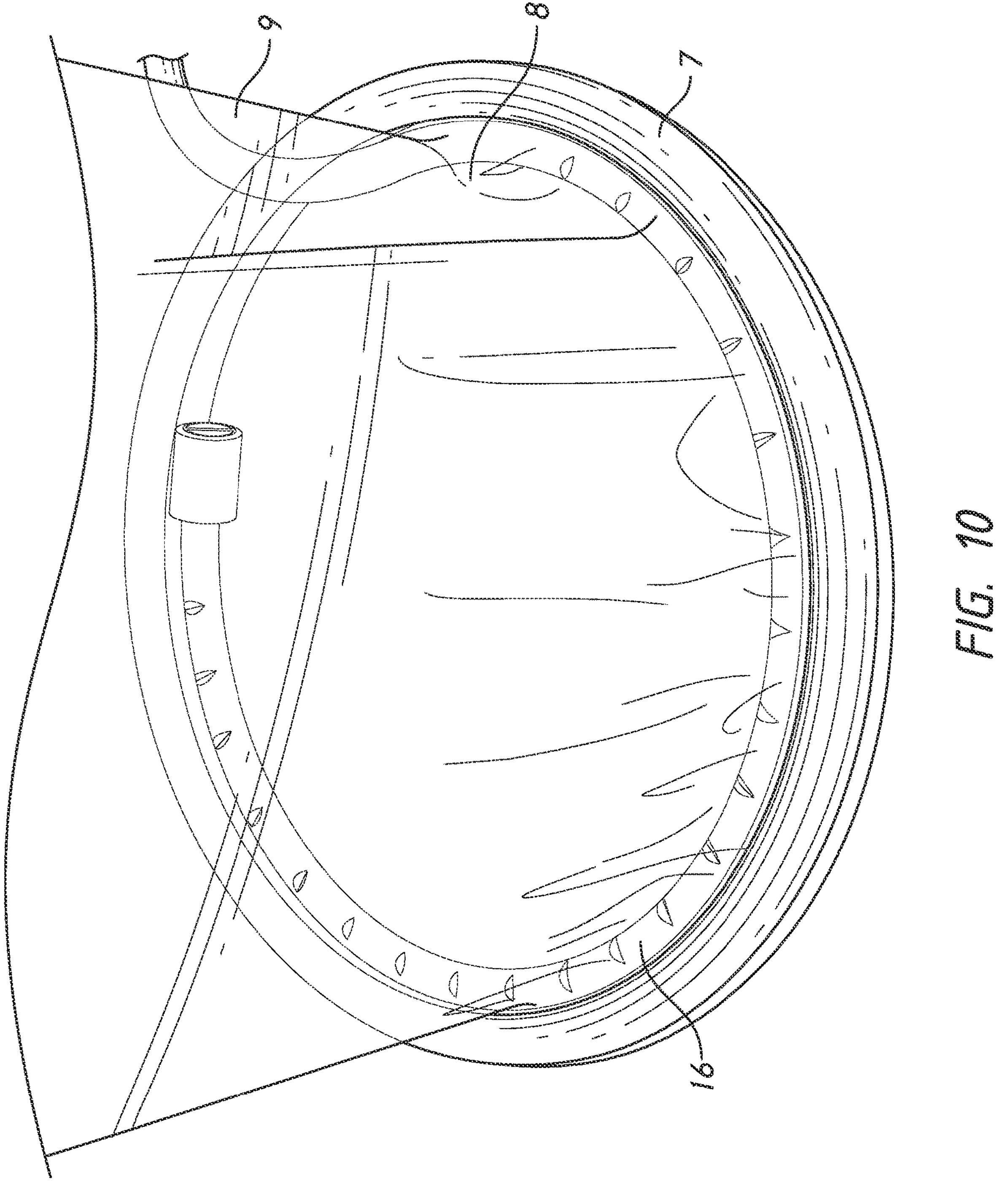
Figure 11:
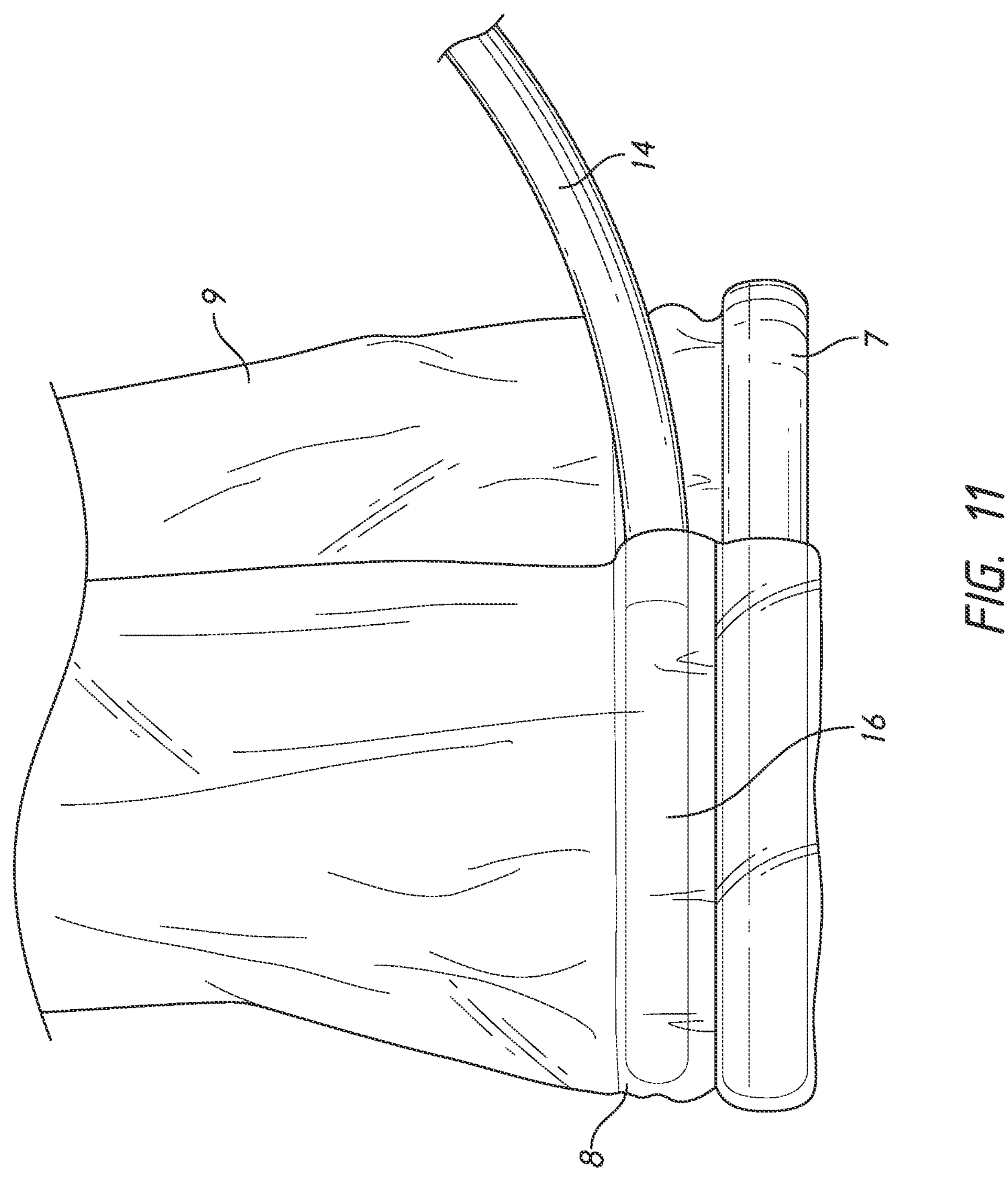
Figure 12:
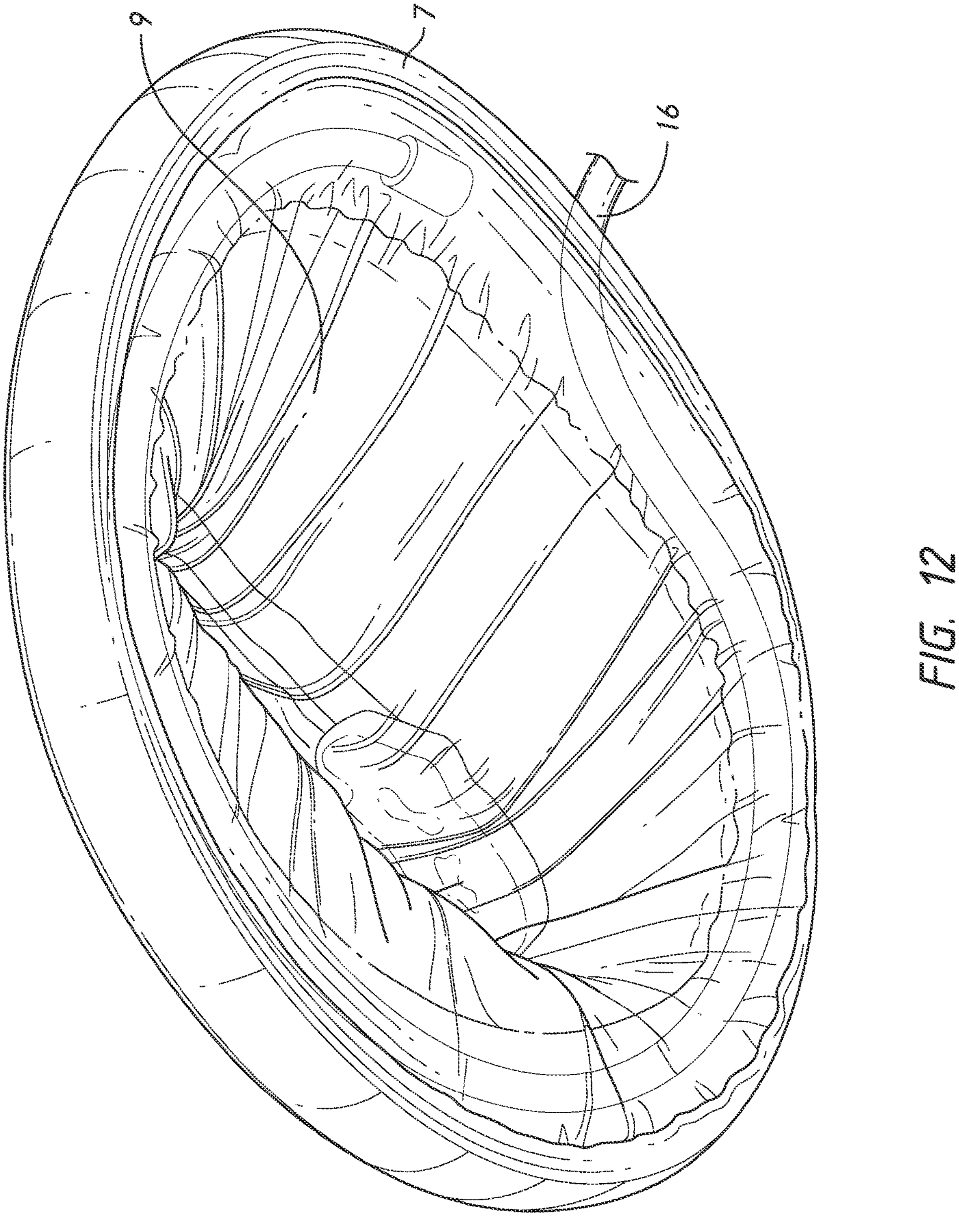
FIG. 12 is a bottom perspective view of portions of an activated lighted surgical access system within and illuminating an internal surgical site in accordance with various embodiments of the present invention.
Figure 13:
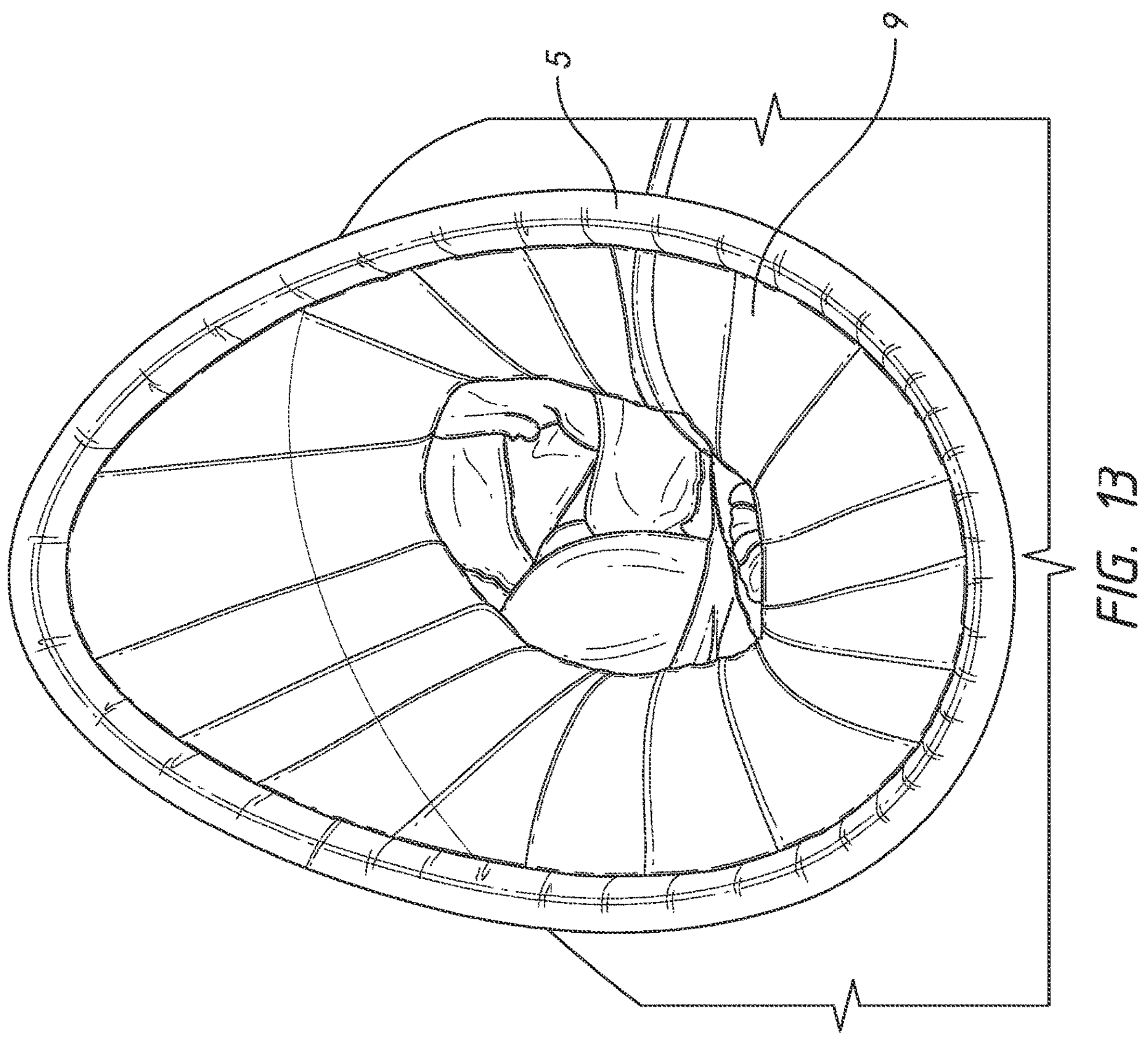
FIG. 13 is a top view of portions of an activated lighted surgical access system within and illuminating an internal surgical site in accordance with various embodiments of the present invention.
Figure 14:
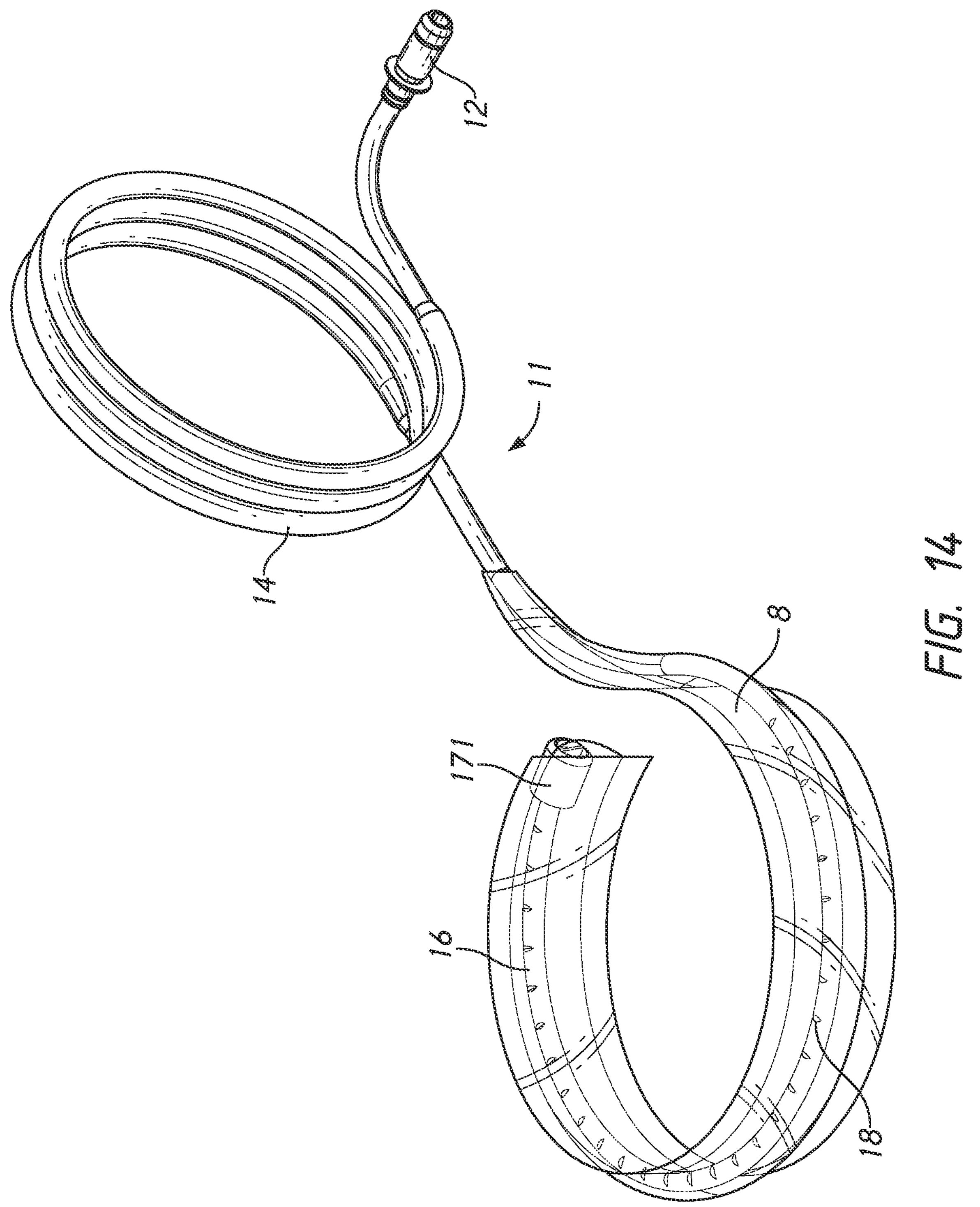
FIG. 14 is a perspective view of portions of a lighted surgical access system in accordance with various embodiments of the present invention.

In various embodiments, the distal end 17 of the POF 11 has a predetermined profile or shape and/or a cap, cover or lens with a predetermined shape or profile to help diffuse or redirect light to the internal anatomy and distribute light/thermal energy more evenly. In various embodiments, the distal end 17 of the POF 11 is coated, covered or otherwise configured to help diffuse or redirect energy or light exiting out the distal portion or end of the POF 11. In various embodiments, the cap, cover or lens is integrated into the distal portion or end 17 of the POF 11 forming a monolithic structure. In various embodiments, the cap, cover, or lens, e.g., cap 171 as shown in FIGS. 5 and 14, is friction-fit, adhered or otherwise attached to the distal portion or end 17 of the POF 11. In various embodiments, the cap, cover or lens has an inner diameter matching or somewhat larger than the outer diameter of the distal portion or end of the POF to friction-fit or otherwise attach to the distal portion or end of the POF. In various embodiments, the cap, cover or lens has an outer diameter larger than the outer diameter of the distal portion or end of the POF. In various embodiments, the cap, cover or lens includes an inner concentric tube or cylinder and/or one or more protrusions configured to attached or connect an outer surface of the inner tube, cylinder or protrusion to an inner surface of the distal portion or end of the POF to further secure the cap, cover or lens to the distal portion or end of the POF. In various embodiments, the cap, cover or lens has one or more indents or cavities along or within an outer or end surface of the cap, cover or lens to facilitate attachment and/or removal of the cap, cover or lens and/or to diffuse or direct energy or light of the POF.

In various embodiments, the cap, cover or lens includes a reflective film, coating or lining to help reflect some of the light energy back into the POF tail which in return is reflected out into the body cavity and/or increase light intensity rather than being fully absorbed by the cap, cover or lens. In various embodiments, a disc of mirror-like reflective film may be placed on, e.g., inside, the cap, cover or lens or adhered to the end portion of the POF tail with the disc reflective film configured to reflect light back into the POF, brightening the light emitted into the body cavity and reducing heat absorbed by the cap, cover, lens or end portion of the POF tail, reducing or lowering temperature experienced by the same. In various embodiments, a cap or cover is positioned on a distal most end of the POF tail both of which are placed within the sleeve and, in various embodiments, the cap, sleeve and/or sheath insulate the outside or surrounding area from heat being generated by the light at the end of the POF tail. In various embodiments, the cap is arranged to minimize the temperature on the outside of the cap. For example, the cap has an outer shell creating an insulating air gap between the core or inner portion of the distal end of the POF tail and/or an inner shell or portion of the cap connected thereto. In various embodiments, the POF and/or the POF tail and/or the cap, cover or lens has a wall thickness, coating, covering and/or material that is configured to prevent the temperature of the POF tail and/or cap, cover or lens from exceeding a predetermined temperature, e.g., 43 degrees C., or range, e.g., 40-45 degrees C. or less than or equal to 43 degrees C.

In various embodiments, the lighted surgical access system includes two thermoplastic polyurethane (TPU) inner and outer rings, TPU film that forms a sheath between the rings, a plastic optical fiber (POF) made from methyl methacrylate, polyolefin heat shrink tubing that covers a portion of the POF, and/or connectors and/or adaptors for compatibility with industry standard surgical light cables.

In accordance with various embodiments, a lighted surgical access device or system is provided to eliminate the drawbacks associated with current surgical lighting technologies. In accordance with various embodiments, the lighted surgical access device or system provides illumination in the internal surgical site, body cavity, incision, or opening while providing 360 degrees of hands-free retraction and/or protection. The lighted surgical access device or system is thus configured to provide circumferential, atraumatic retraction as well as illumination of the internal surgical site, body cavity, incision, or opening to gain maximum exposure within the patient's body cavity, incision and/or opening.

In various embodiments, the lighted surgical access system positions the lighting element underneath the incision or patient opening, which eliminates the problems of glare and/or shadows around the incision and insufficient light entering through small incisions or openings. In various embodiments, the POF is positioned and/or mounted to the sheath above the inner ring thereby avoiding or reducing obstruction by the inner ring, not obstructing the ability of the inner ring to anchor within the patient's cavity and/or not reducing the flexibility of the inner ring in placement through the patient's opening and/or within the patient's cavity, yet aligning light output into the internal surgical site.

In various embodiments, a portion of the POF configured to sit below the incision or patient opening has scoring or cuts to help disperse light from the POF and illuminate the internal surgical site or space, body cavity, incision, or opening. The POF leader or portions thereof of the POF that feeds out through the incision or opening, in various embodiments, is shielded to block light from escaping and terminates with a connector and/or an adaptor to connect to standard surgical lighting units or sources. Positioned under the incision or opening, the light emitting portion of the lighted surgical access system is unable to produce glare on the top of the incision or opening, which preserves the visual contrast of the internal surgical site or space. In addition, since the light is carried into the incision or opening by a POF and then dispersed, the amount of light that can illuminate the surgical space is not limited by the size of the incision or opening.

In various embodiments, the hoop or semi-circular shape of the POF contributes to the lighting effectiveness of the lighted surgical access device or system. In various embodiments, the exposed portion of the plastic optical fiber is mounted circumferentially around the sheath, following the path or outline of the sheath or the inner ring, and light is emitted evenly around the circumference of the sheath or inner ring. Therefore, the light emitted from the system is evenly distributed and/or omnidirectional rather than originating from a single point, which eliminates the problem of shadows being cast in the surgical field. For instance, if the surgeon's hand or an instrument is inserted in the incision or opening and thereby blocking the light or portions thereof from one side of the ring, the other half of the ring will still be illuminating the site, preventing a disruptive shadow. The evenly distributed and/or omnidirectional nature of the light also solves the problems of frequent repositioning (e.g., typically necessary for overhead lamps) and keeping the light pointed in the right direction (e.g., typically problematic for headlamps). With the light positioned in the incision or opening and able to come or be dispersed from all angles, the need to adjust its positioning or angle to achieve sufficient lighting, even when the patient needs to be repositioned, is minimized or eliminated.

With the POF integrated or otherwise attached to the self-retaining retractor allows the lighted surgical access device to be completely hands-free in use. This solves the problem and/or the inconvenience of other lighted retractors, which require a member of the surgical team to continuously hold the retractor in place. Operationally, in accordance with various embodiments, the lighted surgical access device is placed in the incision by squeezing the inner ring and inserting it through the incision or opening, where it then expands and anchors. The outer ring is flipped down to tension the sheath and retract the incision. At this point, the lighted surgical access device or system requires no further adjustment and will continue to retract the incision or opening hands-free. With the POF mounted or otherwise attached to the sheath above or spaced away from the inner ring or distal most portion or end of the sheath, the addition of the POF does not change or otherwise interfere with the retraction operation or procedure and/or anchoring of the inner ring, and the lighted surgical access device or system can be used hands-free after initial positioning. In various embodiments, with the POF mounted or otherwise attached to the sheath above or spaced away from the inner ring or distal most portion or end of the sheath, light interference by the inner ring or distal portions of the sheath can be avoided or eliminated and/or positioning of the POF can be eased and/or optimized.

In various embodiments, the POF is one or more plastic optical fibers. In various embodiments, a bundle of plastic optical fibers is used, enhancing flexibility of the POF, and, in various embodiments have equal diameters. In various embodiments, the POF is a plurality of plastic optical fibers that when bundled together delimit a circle or cylinder having about a 5 mm diameter. In various embodiments, the plurality of plastic optical fibers combines at a junction between the POF leader and the POF tail at or proximate the sheath 9, sleeve 8 and/or the inner ring 5. In various embodiments, a plurality of smaller POF fibers from the POF leader terminate at different points along or proximate the inner ring 5 and/or the distal end of the sheath to disperse light at those selected points. In various embodiments, the POF comprises a plurality of plastic optical fibers having different lengths and/or diameters to disperse light at different points and/or adjust flexibility of the POF at different portions of the POF. In various embodiments, the POF is a single plastic optical fiber having about a 5 mm diameter. In various embodiments, the POF has a diameter that is equal or greater than the diameter of the light cable. In various embodiments, the POF is elongate and tubular and in various embodiments, comprises one or more plastic optical fibers that are elongate and tubular. In various embodiments, the POF leader or portions thereof aligned with a patient's opening or incision has a thinned, reduced or smaller profile, e.g., having an oval, rectangular shape or the like, preventing obstruction and/or interference with the retractor and/or the patient's body, opening and/or an incision.

In various embodiments, the POF or portions thereof is or includes an end-glow fiber to reduce light loss. In various embodiments, the POF comprises different types of plastic optical fibers. For example, in accordance with various embodiments, the POF leader comprises an end-glow POF and transitions to a side-glow POF at a predetermined junction at or proximal to the sheath. In various embodiments, the POF leader comprises an end-glow POF and the POF tail comprises a side-glow POF. In various embodiments, a coupler, e.g., a T-shaped coupler, is provided in that the POF leader terminates at or proximate the inner ring with the T-shaped coupler positioned and connecting between the POF leader and one or more side-glow POFs, e.g., the POF tail comprises one or more side-glow POFs. In various embodiments, the POF or portions thereof are molded to an arcuate or circular shape having one or more bubbles embedded therein to disperse light away from the outer ring and towards the internal surgical site or area of interest.

In various embodiments, the POF and/or sleeve is configured to not exceed a predetermined temperature, e.g., 40-45 degrees C. or 43 degrees C. In various embodiments, the POF and/or sleeve so configured includes one or more layers, coatings, films or thermal or heat dissipating or reducing insulation. In various embodiments, an additional or second sleeve is provided and attached to the sheath. The second sleeve encases or covers the POF leader. In various embodiments, the second sleeve is orientated vertically or diagonally relative to a longitudinal axis of the sheath and its access channel. In various embodiments, the second sleeve is oriented in a transverse direction relative to the sleeve containing the POF tail. In various embodiments, the second sleeve and the sleeve containing the POF tail are combined or monolithically formed to provide a single structured sleeve. In various embodiments, all or portions of the POF and/or sleeve includes or is integrated with a reflective film, coating or cover to reflect light back into the POF to reduce light loss. In various embodiments, a cable-management device or system is attached or integrated with the POF to regulate, control or dispense a desired length of the POF for operational use while any excess remains managed, e.g., coiled or wrapped, to prevent obstruction of an excess portion of the POF.

In operation, surgical retraction is achieved by first compressing and inserting the inner ring into the incision or opening and seating it beneath the desired anchoring tissue. The outer ring is then flipped or rolled by the user, which tensions the sheath and applies outward pressure to the wound or opening, effectively retracting the tissue. Placement of the POF being proximate and/or spaced from the inner ring or distal most portion of the sheath places the POF within the internal surgical site and/or the access channel, beneath the anchoring tissue and/or the incision or opening. The lighted surgical access system illuminates the internal surgical site and/or the access channel by transmitting light through the POF, which is sealed onto the sheath above the inner ring, and spans from within the incision or opening to outside the sterile field. Light is provided from a surgical light source and is transferred through a surgical light cable. The light cable is connected to one of the adaptors of the system. Once the surgical procedure is completed or as desired, the user can disconnect the light cable from the adaptor and/or connector and extract the lighted surgical access device from the surgical site.

In various embodiments, the POF is kept separated from the sheath and subsequently attached to the sheath for operational use. In various embodiment, the POF is incorporated, fitted or placed into the sleeve of the sheath at the time of the procedure or in anticipation of the surgical procedure for operational use. In various embodiment, the sheath comprises a pocket in which the POF is incorporated or placed into the sheath at the time of the procedure or in anticipation of the surgical procedure for operational use. In various embodiments, the POF with or without the sleeve is entrapped between the inner ring and the sheath by wrapping the sheath around the POF by, for example, flipping the inner ring attached to the sheath over and around the POF. In various embodiments, a cushion or impact resistant barrier is provided such as rubber or elastomeric cushion attached or otherwise connected to the POF, sheath and/or sleeve to insulate or protect the body or surgical opening from manipulations or pressure exerted by the POF during operational use. In various embodiments, the cushion or impact resistant barrier is disposed between the POF tail, leader and/or both and the body opening and/or incision. In various embodiments, the POF tail, leader or both is disposed between the cushion and/or impact resistant barrier and/or the sheath and/or sleeve.

In various embodiments, the lighted surgical access system may include a retractor and a POF connected to or otherwise attached to the retractor. In various embodiments, the lighted surgical access system may include a light source, a retractor and a POF connected to the retractor and the light source. In various embodiments, the POF is removably connected to the light source and/or the retractor. In various embodiments, the lighted surgical access system can include a light cable connecting the light source to the POF. In various embodiments, the lighted surgical access system may include a surgical access device and a POF connected to or otherwise attached to the surgical access device. In various embodiments, the surgical access device may be or include a retractor, a cannula, a trocar or the like providing access or a channel or pathway into a patient's body cavity and/or in various embodiments may be flexible being able to bend and/or allow tissue or the like to deform or compress portions thereof.

In various embodiments, the lighted surgical access system may include a retractor that is adjustable in length to accommodate different patient anatomy and/or 360 degrees of hands-free protection and/or retraction of the opening in the patient. In various embodiments, the retractor may not include an outer ring, an inner ring or both. In various embodiments, the lighted surgical access system may comprise a surgical access device, a POF and/or a light source. In various embodiments, the lighted surgical access system comprises a POF. In various embodiments, the POF is spaced and separated from the inner ring and/or the distal most portion, component or end of the sheath or surgical access device. In various embodiments, the POF is fixed to the sheath or otherwise confined longitudinally or lengthwise along or relative to the sheath. In various embodiments, one or more POFs may be attached to the sheath with one or more extending circumferentially or along portions thereof around the sheath. In various embodiments, the inner ring or support or portions thereof in its entirety or one or more portions thereof is made of one or more POFs, e.g., a molded POF and/or side-glow POFs. As such, in various embodiments, one or more POFs, as described throughout the application, can be used in lieu of or to act as an inner ring. In various embodiments, the sheath or portions thereof is arranged to act as a light curtain carrying light under the body wall or patient opening to or at the internal surgical site. In various embodiments, a skirt, drape, and/or a second sheath is attached and/or extends from the distal end of the sheath and/or the inner ring to act as a light curtain to carry light under the body wall or patient opening to or at the internal surgical site.

In various embodiments, the POF comprises a POF leader and/or a POF tail. In various embodiments, the light cable and/or intermediaries thereto is directly connected to the POF tail, e.g., the POF leader is removed. In various embodiments, the POF includes a core and a cladding surrounding or encasing the core. In various embodiments, the POF outer cladding layer is modified, such as added surface roughness, to enhance light scattering. In various embodiment, the outer cladding layer is removed or portions thereof, e.g., exposing one or more sections of the core of one or more portions of the POF, e.g., the POF tail or portions thereof, under the incision or internal surgical site of interest. In various embodiments, a light emitter system comprises one or more POFs or portions thereof.

In various embodiments, the POF and/or the POF tail includes one or more cuts, protrusions, projections, or other deflection and/or reflection points, portions or area are shaped, sized or otherwise dimensioned to adjust light scattering of the POF. In various embodiments, the POF and/or the POF tail includes one or more cuts, protrusions, projections or other deflection and/or reflection points, portions or area to partially direct light in one or more specific directions. In various embodiments, a specific direction is towards an internal surgical site or area of interest and/or away from or opposite that of outside the patient or outer portion of the surgical access system. The one or more cuts, protrusions, projections or other deflection and/or reflection points, portions or area, in various embodiments, allow or permit the incoming light to also travel along any remainder or further along portions of the POF, opposite the incoming light travel. In various embodiments, the one or more cuts, protrusions, projections or other deflection and/or reflection points, portions or area are holes, channels, grooves, apertures or the like are angled, e.g., normal or at 45 degrees or less relative to the POF or light cable. In various embodiments, the POF and/or the POF tail includes one or more cuts, protrusions, projections or other deflection and/or reflection points, portions or area that are molded or otherwise preformed with predetermined shapes, sizes and/or dimensions to adjust or provide optimal scattering or dispersion of light. In various embodiments, the POF and/or the POF tail includes one or more cuts, protrusions, projections or other deflection and/or reflection points, portions or area that are above or on a side away from the inner ring and/or an internal surgical site or area of interest. In various embodiments, the light travels encountering other deflection, reflection or refraction points or areas and/or ultimately to the POF's terminal end. In various embodiments, the POF's terminal end comprises a specific profile and/or end cap or cover that deflections, reflections or retractions the incoming light in one or more specific directions, including allowing the incoming light to proceed uninterrupted upon exiting the terminal end of the POF, as provided by the end profile or cap. In various embodiments, the POF comprises a connector, a POF leader, a POF tail, an end cap and/or any combination thereof.

Figure 22:
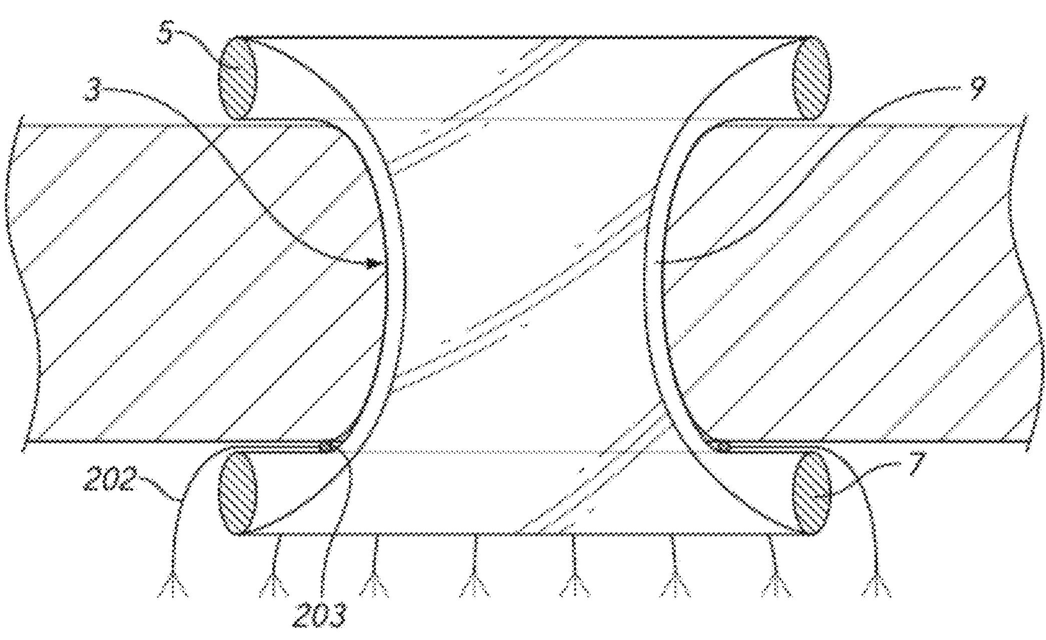
FIG. 22 is a cross-sectional side view of a lighted surgical access system in accordance with various embodiments of the present invention.
Figure 23:
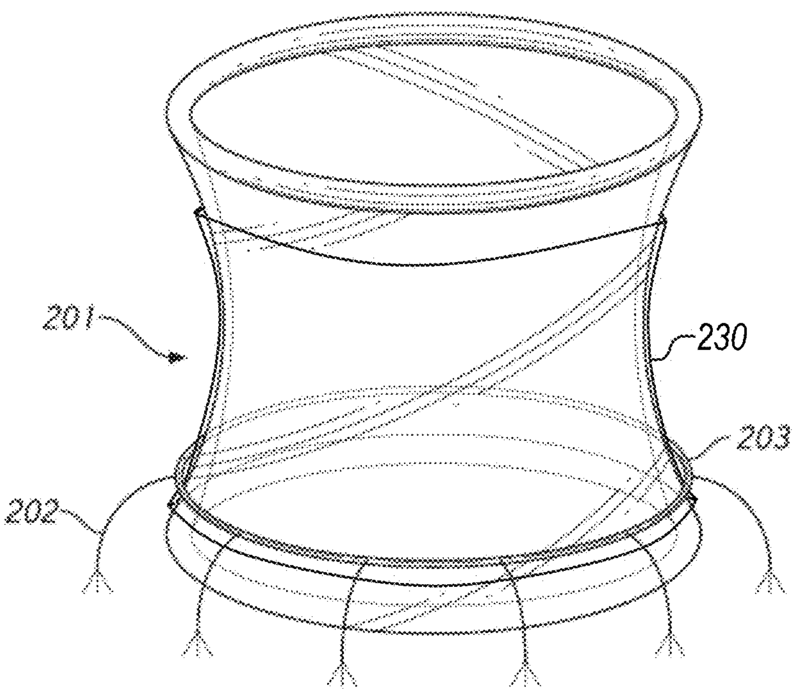
FIG. 23 is a perspective view of a lighted surgical access system in accordance with various embodiments of the present invention.

In reference to FIGS. 22-23, in accordance with various embodiments, a lighted surgical access system 3 is provided that includes outer ring 5 and inner ring 7 with a sheath 9 connecting the rings together. The length of the sheath 9 is adjustable by rolling or wrapping the sheath around the outer ring. Attached to the inner ring 7, in various embodiments, is a light skirt 201. The skirt includes one or more light strands, strings, strips, bands, or drapes 202 extending from a hoop or semi-circular ring 203 attached to an outer surface of the sheath above the inner ring. In various embodiments, the hoop 203 has a width or diameter smaller than the diameter of the outer ring, inner ring, or both. The one or more strands, strings, strips, bands, or drapes hangs over and extends pass the inner ring to illuminate the internal surgical site or space. Light is provided by or to the skirt and/or one or more strands, strings, strips, bands or drapes by a light emitter system connectable there to and comprising one or more light sources, carriers, emitters or the like, including but not limited to, light boxes, LEDs, POFs and any various equivalents or combinations thereof integrated therein or attached thereto. In various embodiments, the skirt may be movable, removable and/or adjustable and thus arranged to vary the position of the one or more light sources. In various embodiments, the one or more light sources are adjustable, removable and/or repositionable and thus can arranged to vary the position of the one or more light sources relative to each other and/or the skirt to vary illumination and reduce potential obstructions by the one or more light sources and/or glare. It should be appreciated that additional light sources could be provided and/or a single light source to adjust or vary illumination and/or potential physical or visual obstructions.

In various embodiments, the size, shape and/or dimensions of the strands, strings, strips, bands, or drapes 202 can vary relative to each other and/or the skirt. In various embodiments, the stands, bands, or drapes 202 extend generally longitudinally or are aligned with a longitudinal axis of the sheath extending from the skirt and distally away from the skirt and/or the inner ring. In various embodiments, the strands, strings, strips, bands, or drapes have a width smaller than their length. In various embodiments, the strands, strings, strips, bands or drapes have a width smaller than the width or height of the outer ring 5 or the inner ring 7 and/or a length greater than the width or height of the outer ring 5 or the inner ring 7.

Figure 24:
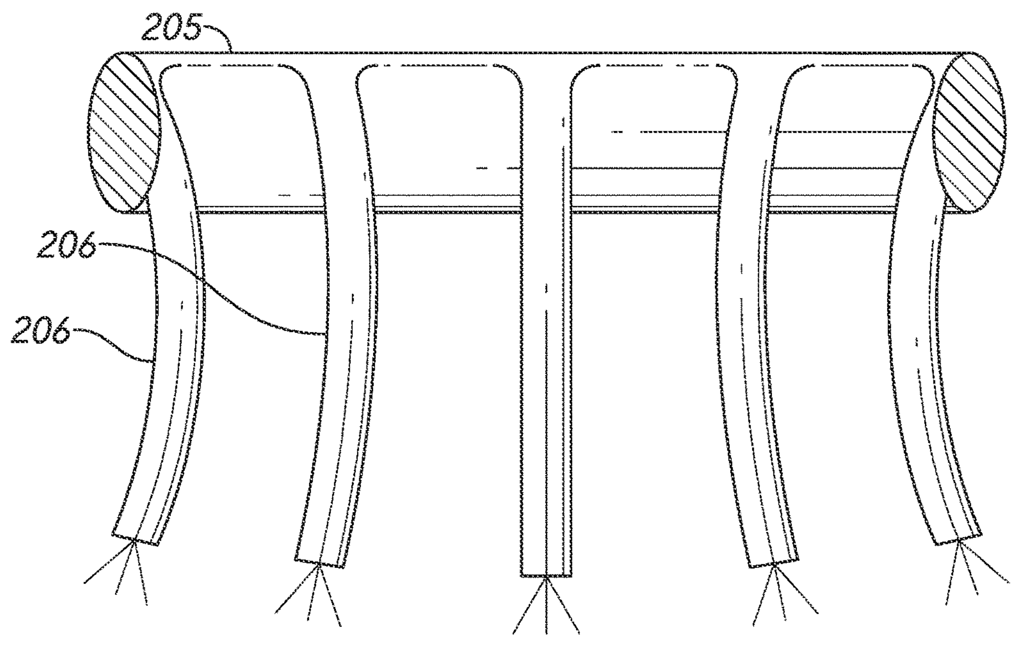
FIG. 24 is a cross-sectional side view of a lighted surgical access system in accordance with various embodiments of the present invention.
Figure 25:
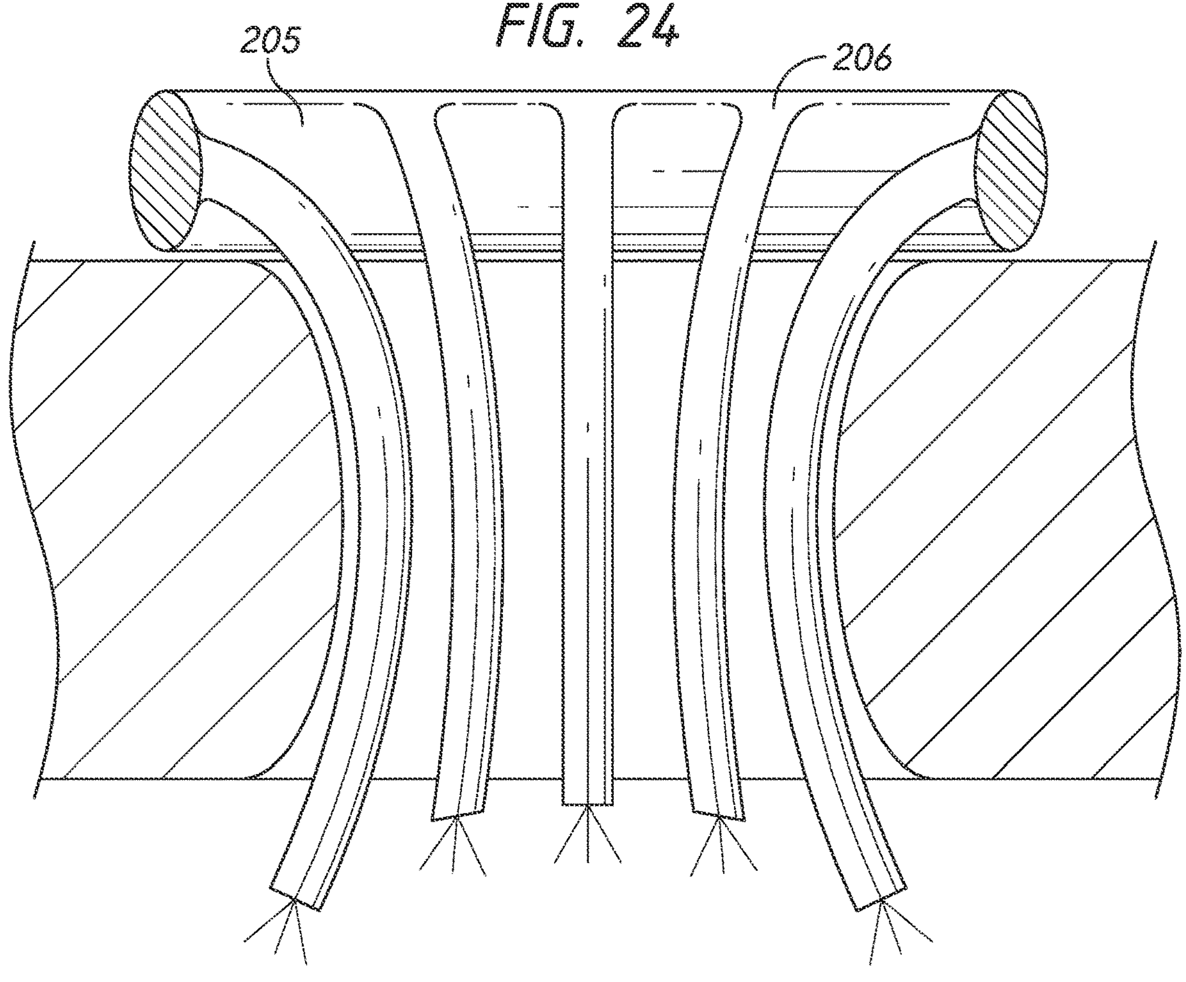
FIG. 25 is a cross-sectional side view of a lighted surgical access system in accordance with various embodiments of the present invention.

In various embodiments, as exemplarily illustrated in FIGS. 24-25, a flexible semi-circular, circular, arcuate section, curved support or hoop 205 is removably attachable to the outer ring 5. The outer ring 5 attached to the curved support or flexible hoop 205 anchors the flexible hoop outside a patient's opening. In various embodiments, the hoop 205 has or defines a diameter or width greater than the diameter of the outer ring and in various embodiments, the hoop is more flexible relative to the outer ring. Extending from the hoop is one or more curved flanges 206 extendable, expandable, flexible and/or deformable to conform with the patient's opening. In various embodiments, at the distal end of the flanges, light is provided to illuminate the internal surgical site. Light is provided by or to the one or more curved support or hoops 205 and/or flanges 206 by a light emitter system connectable there to and comprising one or more light sources, carriers, emitters or the like, including but not limited to, light boxes, LEDs, POFs and any various equivalents or combinations thereof, integrated therein or attached thereto. In various embodiments, the curved flanges 206 can be pinched together for insertion and then rebound to the contours of the incision once placed. In various embodiments, the one or more flanges and/or hoops may be provided without a sheath, an outer ring and/or an inner ring. In various embodiments, the one or more flanges and/or hoops may be movable and/or adjustable and thus arranged to vary the position of the one or more light sources. In various embodiments, the one or more flanges are bendable to be inserted through the access channel defined by the sheath. In various embodiments, the one or more light sources connectable to the one or more flanges and/or hoops are adjustable and/or repositionable and thus can arranged to vary the position of the one or more light sources relative to each other and/or the flange.

In various embodiments, the size, shape and/or dimensions of the one or more flanges 206 can vary relative to each other and/or the hoop 205. In various embodiments, the one or more flanges 206 extend generally longitudinally or are aligned with a longitudinal axis of a sheath extending from the hoop 205 and distally away from the hoop and/or an outer ring. In various embodiments, the one or more flanges have a width smaller than their length. In various embodiments, the one or more flanges have a width smaller than the width or height of the hoop, an outer ring and/or an inner ring and/or a length greater than the width or height of the hoop, the outer ring or the inner ring.

Figure 26:
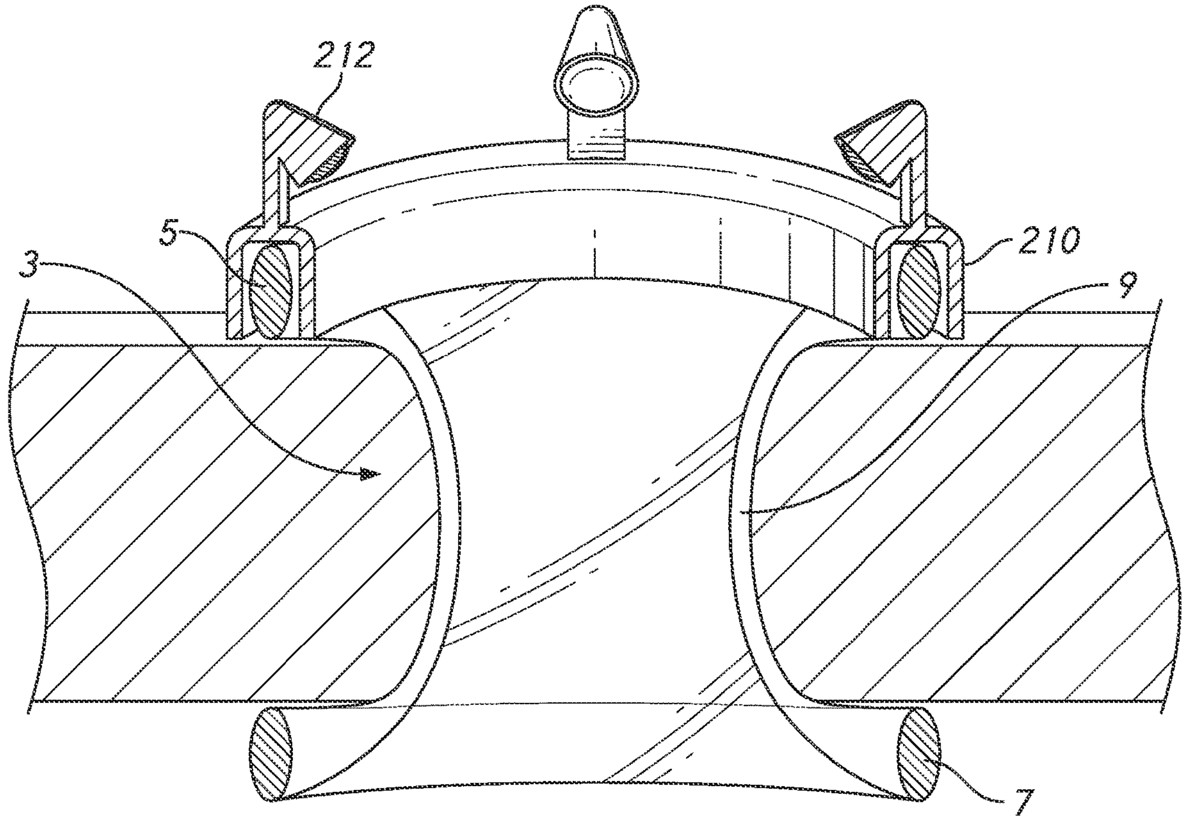
FIG. 26 is a cross-sectional side view of a lighted surgical access system in accordance with various embodiments of the present invention.

In various embodiments, as exemplarily illustrated in FIG. 26, a flexible cap or flange 210 is removably connected to the outer ring 5. The flange is circular, semi-circular or has an arcuate section with light provided via one or more light emitters, e.g., lamps 212, extending proximally from the flange and directing or directable distally, towards the inner ring and/or into the patient's opening. Light is provided by or to the one or more flanges and/or lamps by a light emitter system connectable thereto and comprising one or more light sources, carriers, emitters or the like, including but not limited to, light boxes, LEDs, POFs and any various equivalents or combinations thereof, integrated therein or attached thereto. In various embodiments, the one or more flanges and/or cap has or defines an inner diameter or width smaller than an inner diameter of the outer ring and an outer diameter greater than the outer diameter of the outer ring. In various embodiments, the one or more flanges and/or cap is more flexible relative to the outer ring. In various embodiments, the cap and/or flange is movable, e.g., rotatable or slidable, relative to the outer ring. In various embodiments, the one or more flanges may be movable and/or adjustable and thus arranged to vary the position of the one or more light sources. In various embodiments, the one or more light sources connectable to the flange and/or light emitters are adjustable and/or repositionable and thus can arranged to vary the position of the one or more light sources relative to each other and/or the flange. In various embodiments, the one or more light emitters are adjustable in position relative to the cap, flange and/or each other and independently adjustable relative to the cap, flange and/or each other. In various embodiments, the one or more flanges includes a channel arranged to snap or otherwise connect to the outer ring 5. The channel in various embodiments includes one or more ledges, protrusions, snaps and/or other connecting features to secure the flange 210 to the outer ring. In various embodiments, one or more flanges 210 can be provided to vary the position of the one or more light sources and/or to reduce any potential external obstruction of the one or more light sources and/or to increase illumination to a particular section or side along the flange or the outer ring. In various embodiments, the light emitters are each adjustable to vary the illumination or light direction of the light emitters, as desired, in various directions or heights, for example, being on swivels, adjustable arms, balls and sockets, ratchets and the like. In various embodiments, the one or more light emitters are removable from the flange to vary illumination and reduce potential obstructions by the one or more light emitters and/or glare. In the illustrated embodiment, three lamps 212 are shown. However, it should be appreciated that additional lamps could be provided and/or a single lamp to adjust or vary illumination and/or potential physical or visual obstructions. In various embodiments, the one or more lamps 212 extends vertically away from the flange and then is angled distally towards the patient's opening or the internal surgical site.

Figure 27:
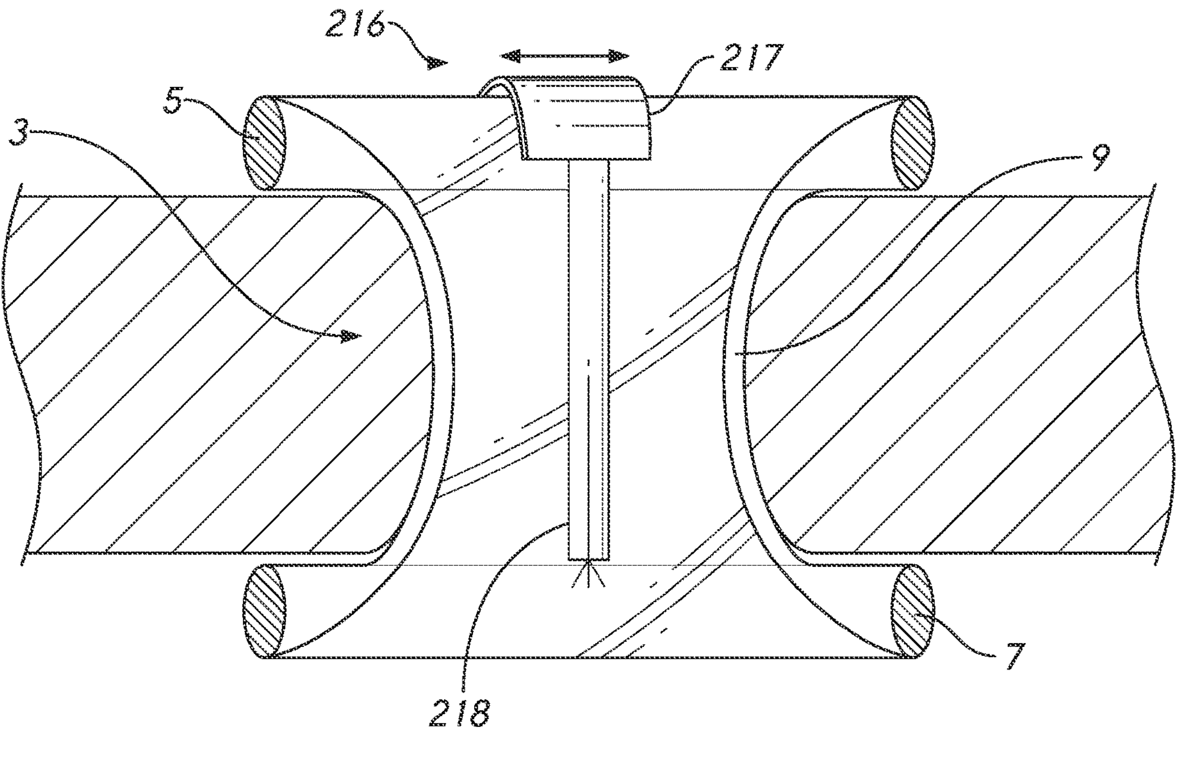
FIG. 27 is a cross-sectional side view of a lighted surgical access system in accordance with various embodiments of the present invention.
Figure 28:
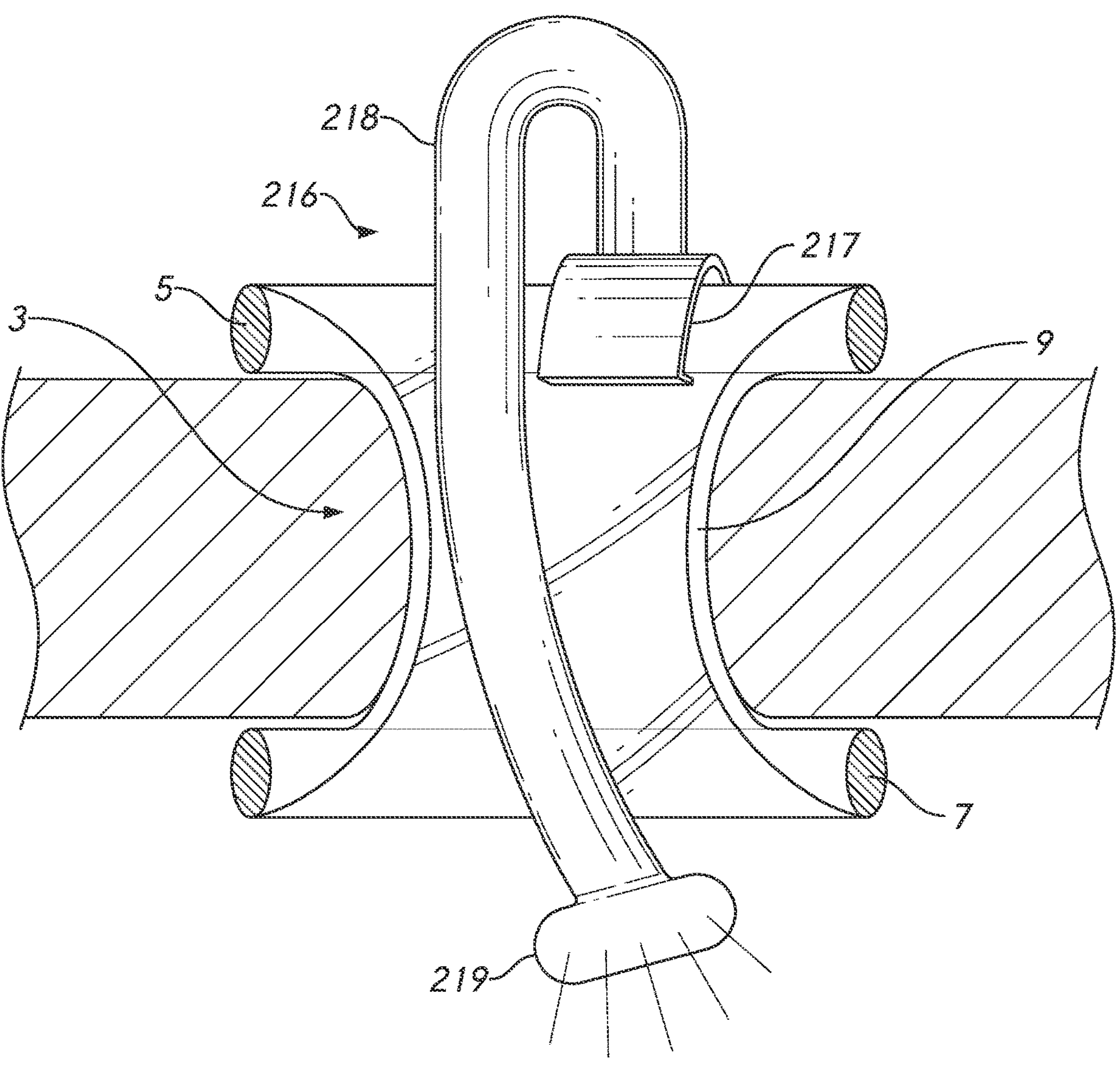
FIG. 28 is a cross-sectional side view of a lighted surgical access system in accordance with various embodiments of the present invention.

In accordance with various embodiments, as illustrated exemplarily in FIGS. 27-28, one or more light clips 216 are removably attachable, e.g., clipped, to the outer ring 5. The light clip is movable, e.g., slidable, and/or repositionable along the perimeter of the outer ring. The light clip in various embodiments comprises a clip 217 and one or more adjustable or malleable necks 218 with the clip attached to the outer ring and the neck bendable and extendable from the clip and towards the inner ring and through the patient opening or access channel of the sheath 9. In various embodiments, light is emitted from a distal portion or distal end, e.g., enlarged end 219, of the neck 218. Light is provided by or to the one or more clips, necks and/or enlarged end by a light emitter system connectable thereto and comprising one or more light sources, carriers, emitters or the like, including but not limited to, light boxes, LEDs, POFs and any various equivalents or combinations thereof, integrated therein or attached thereto. In various embodiments, as shown for example in FIG. 28, the malleable or adjustable neck and/or clip of the light clip is positioned or positionable to remain outside the patient's opening such that light can be emitted distally from outside the patient opening and additionally or alternatively bend to be positioned within the patient opening and/or access channel of the retractor and/or up to and/or beyond the inner ring. In various embodiments, similar to FIG. 28, the one or more neck and/or clip of the light clips is instead or additionally removably attached to the inner ring and bendable to be positioned deep within, e.g., further past the distal end of the retractor, the patient opening, body cavity and/or portions of the patient's internal organs or tissues not accessible and/or where additional or greater illumination is desired. In various embodiments, the one or more neck and/or clip of the light clips are bendable from the inner ring up and/or along the access channel of the retractor.

In various embodiments, the size, shape and/or dimensions of the one or more necks 218 can vary relative to each other and/or the clip 217. In various embodiments, the one or more necks 218 extend generally longitudinally or are aligned with a longitudinal axis of a sheath extending from the clip 217 and distally away from the clip 217 and/or an outer ring 5. In various embodiments, the one or more necks have a width smaller than their length. In various embodiments, the one or more necks have a width smaller than the width or height of the clip, an outer ring and/or an inner ring and/or a length greater than the width or height of the clip, the outer ring or the inner ring.

Figure 29:
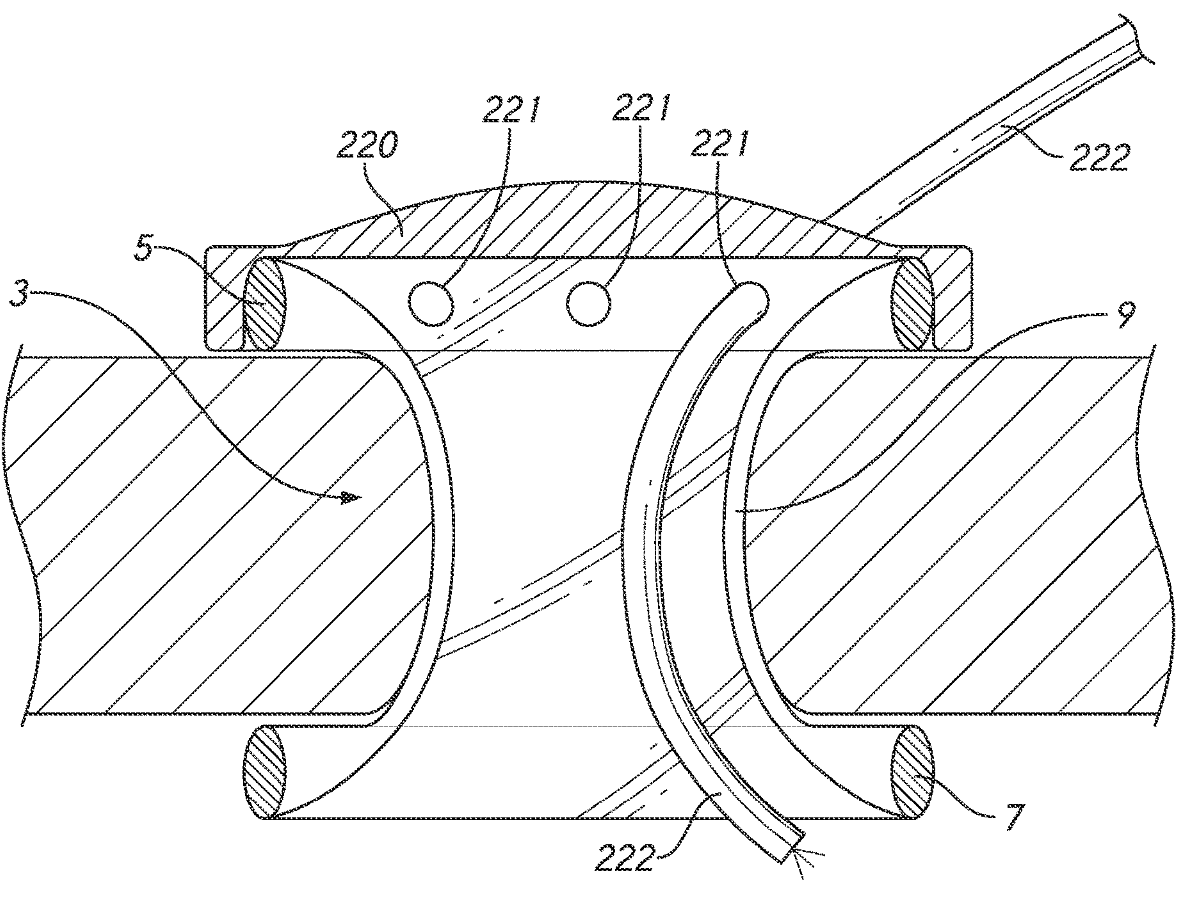
FIG. 29 is a cross-sectional side view of a lighted surgical access system in accordance with various embodiments of the present invention.

As shown, for example, in FIG. 29, in various embodiments, a cap 220 is removably connected to the outer ring 5. The cap includes one or more apertures, holes, or slots 221 through which one or more light bands or tubes 222 can extend therethrough and distally towards the inner ring 7. In various embodiments, the cap may cover an entire opening of the outer ring thereby sealing or blocking an access channel of the sheath 9. In various embodiments, the cap covers a portion of the opening defined or delimited by the outer ring and seals or blocks a portion of the access channel defined or delimited by the sheath 9 to limit or confine the light tubes to a particular portion or area relative to the outer ring and/or sheath. In various embodiments, the cap includes a gel, an ultra-gel and/or an elastomeric material. In various embodiments, the cap includes a penetrable and sealable material, e.g., gel, configured to seal against inserted instruments and/or the light tubes and/or to provide a seal in the absence of instruments inserted therethrough. In various embodiments, the cap covers an entire opening of the outer ring to seal the access channel of the sheath. In various embodiments, the cap covers only a portion of an opening defined by the outer ring. In various embodiments, the cap comprises an elastomeric material through which apertures and/or light tubes or bands extends therethrough. The one or more light bands or tubes are bendable and extendable from the cap and towards the inner ring and through the patient opening or access channel of the sheath. Light is emitted from a distal portion or distal end of the one or more light tubes. Light is provided by or to the light bands or tubes by a light emitter system connectable thereto and comprising one or more light sources, carriers, emitters or the like, including but not limited to, light boxes, LEDs, POFs and any various equivalents or combinations thereof, integrated therein or attached thereto. In various embodiments, one or more of the one or more light bands or tubes may be POFs, LED strings or strips or the like.

In various embodiments, the size, shape and/or dimensions of the one or more light bands or tubes 222 can vary relative to each other. In various embodiments, the one or more light bands or tubes 222 extend generally longitudinally or are aligned with a longitudinal axis of the sheath distally away from the outer ring 5. In various embodiments, the one or more light bands or tubes 222 have a width smaller than their length. In various embodiments, the one or more light bands or tubes have a width smaller than the width or height of the outer ring and/or the inner ring and/or a length greater than the width or height of the outer ring or the inner ring. In various embodiments, the one or more light bands or tubes 222 are more flexible than the outer ring 5.

Figure 30:
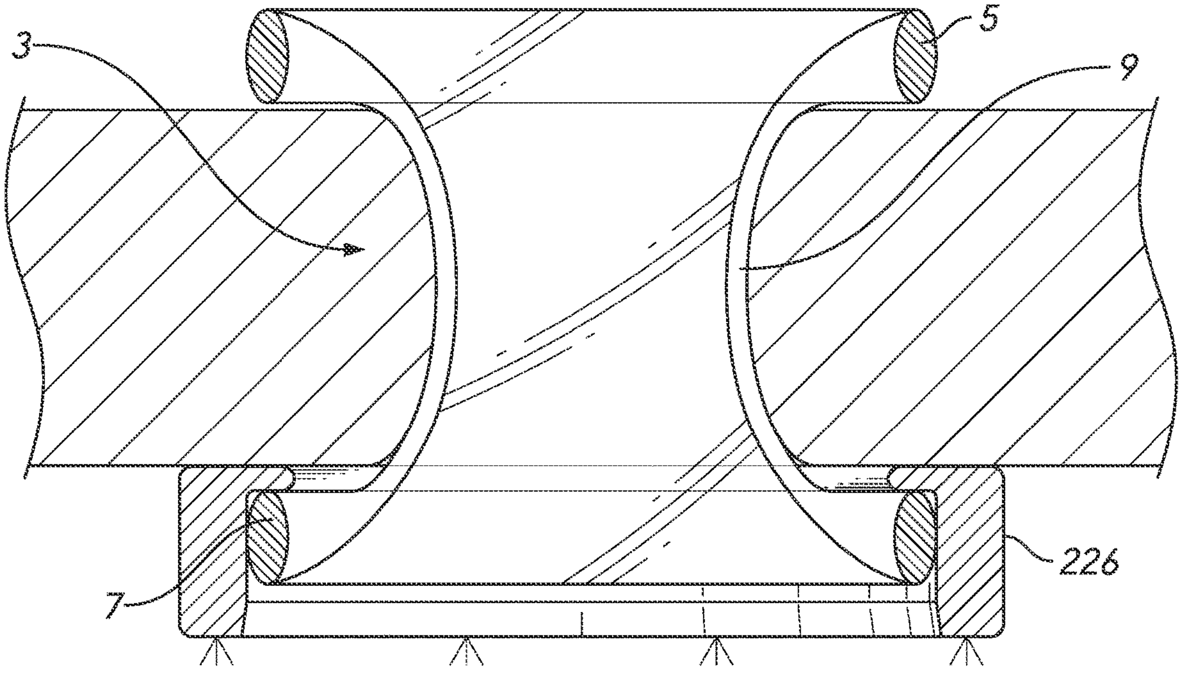
FIG. 30 is a cross-sectional side view of a lighted surgical access system in accordance with various embodiments of the present invention.

Exemplified in FIG. 30, in accordance with various embodiments, an inner semi-circular, circular, or arcuate or curved support or hoop 226 is removably connectable to the inner ring 7. The inner section curved support or hoop 226 is configured to sit or be positioned partially between the inner ring and the inner cavity or tissue of the patient. The inner section curved support or hoop in various embodiments is flexible to be folded or deformed to be inserted the patient's opening and/or the access channel of the retractor. In various embodiments, the curved support or hoop 226 has or defines a distal diameter or width greater than the diameter of the inner ring and in various embodiments, the curved support or hoop is more flexible relative to the outer ring. In various embodiments, the inner curved support or hoop has a diameter greater than a diameter of the inner ring and/or a diameter smaller than an outer diameter of the outer ring. In various embodiments, the inner curved support or hoop is more flexible relative to the outer ring. In various embodiments, the inner curved support or hoop has a channel arranged to snap onto the inner ring. In various embodiments, the inner curved support or hoop has a cross-sectional L-shape. In various embodiments, the inner curved support or hoop in its entirety is disposed outside the access channel. In various embodiments, the inner curved support or hoop is transparent or translucent. In various embodiments, the inner curved support or hoop has a lower surface that faces away from the inner ring and is transparent or translucent. In various embodiments, the inner curved support or hoop has one or more apertures and/or lenes through which light is emitted therethrough. Light is emitted from a distal portion or distal end of the inner section or hoop. Light is provided by or to the inner section curved support or hoop by a light emitter system connectable thereto and comprising one or more light sources, carriers, emitters or the like, including but not limited to, light boxes, LEDs, POFs and any various equivalents or combinations thereof, integrated therein or attached thereto. In various embodiments, the one or more sections, curved supports or hoops includes a channel arranged to snap or otherwise connect to the inner ring 7. The channel in various embodiments includes one or more ledges, protrusions, snaps and/or other connecting features to secure the section or hoop 226 to the inner ring. In various embodiments, one or more sections, curved supports or hoops can be provided to vary the position of the one or more light sources and/or to reduce any potential external obstruction of the one or more light sources and/or to increase illumination to a particular section or side along the section or hoop or the inner ring.

Figure 31:
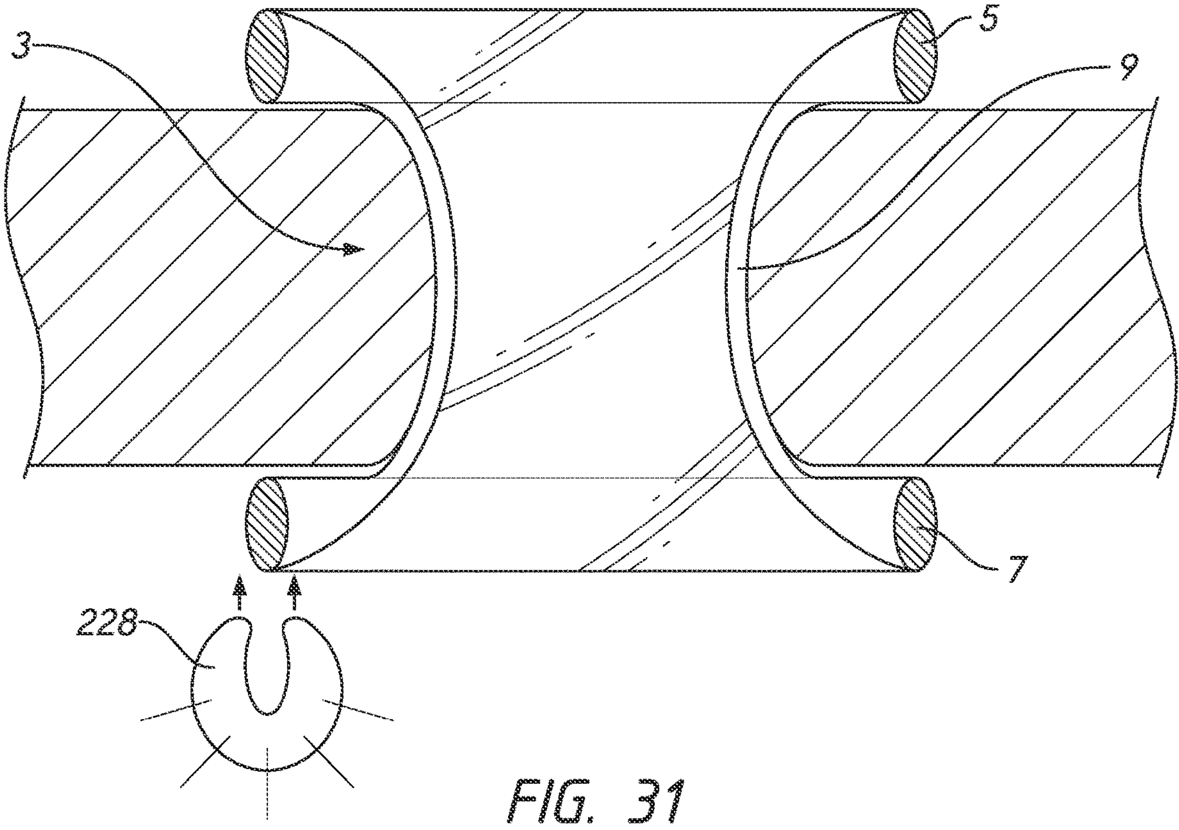
FIG. 31 is a cross-sectional side view of a lighted surgical access system in accordance with various embodiments of the present invention.

In FIG. 31, for example, in accordance with various embodiments, one or more light clips 228 are removably attachable, e.g., clipped or snapped, onto the inner ring. The light clip is movable, e.g., slidable, and/or repositionable along the perimeter of the inner ring. Light is provided by or to the light clips by a light emitter system connectable thereto and comprising one or more light sources, carriers, emitters or the like, including but not limited to, light boxes, LEDs, POFs and any various equivalents or combinations thereof, integrated therein or attached thereto. Light is emitted from a distal portion or distal end of the light clip. In various embodiments, the light clip is dimensioned, flexible and/or shaped to fit through the patient opening and/or the access channel of the retractor and attachable to the inner ring. In various embodiments, the one or more clips includes a channel arranged to snap or otherwise connect to the inner ring 7. The channel in various embodiments includes one or more ledges, protrusions, snaps and/or other connecting features to secure the clips 228 to the inner ring. In various embodiments, one or more clips can be provided to vary the position of the one or more light sources and/or to reduce any potential external obstruction of the one or more light sources and/or to increase illumination to a particular section or side along the inner ring. In various embodiments, the light clip is transparent or translucent. In various embodiments, the light clip covers a portion of a lower surface of the inner ring and/or has a cross-sectional U-shape. In various embodiments, the light clip has a first upper portion in contact with a surface of the inner ring facing away from the access channel, a second upper portion in contact with a surface of the inner ring facing towards the access channel, and a lower portion connecting the first upper portion to the second upper portion. In various embodiments, the light clip has a width and length smaller than an inner diameter of the inner ring and/or has a channel arranged to snap onto the inner ring.

Figure 32:
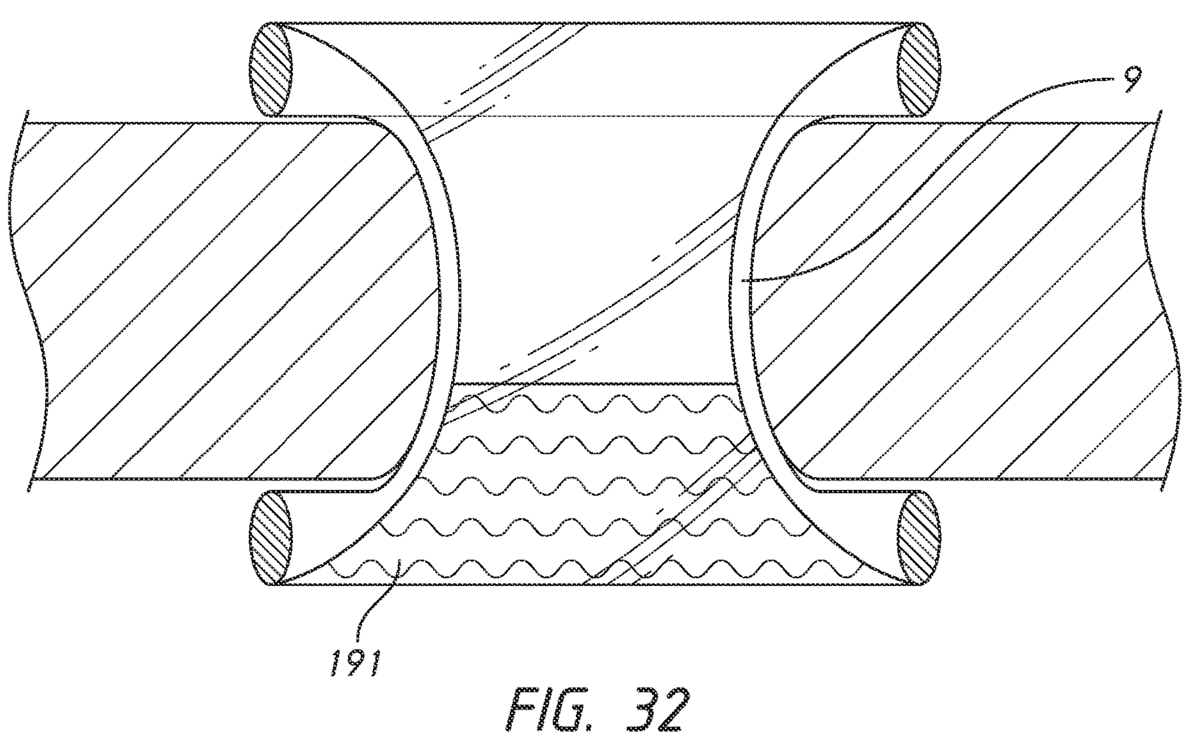
FIG. 32 is a cross-sectional side view of a lighted surgical access system in accordance with various embodiments of the present invention.
Figure 33:
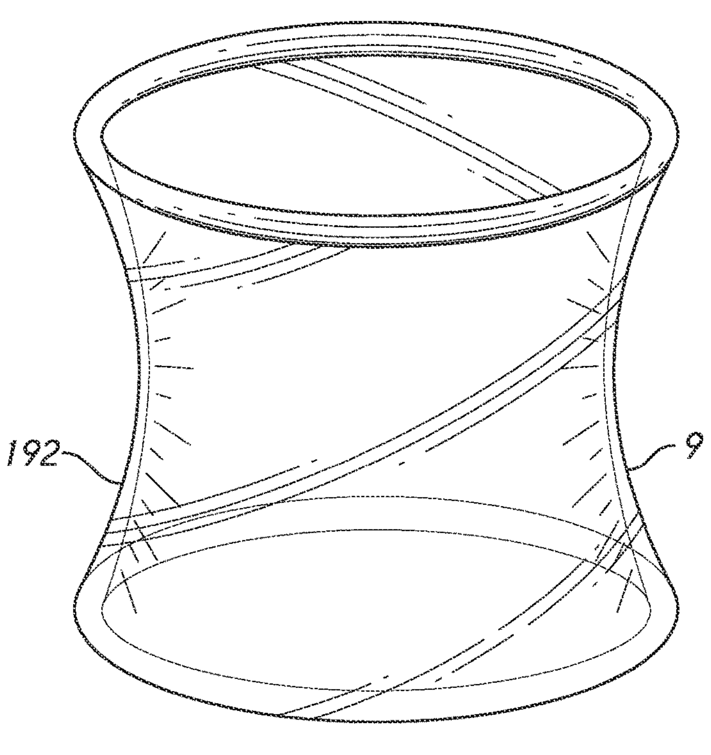
FIG. 33 is a perspective side view of a lighted surgical access system in accordance with various embodiments of the present invention.
Figure 34:
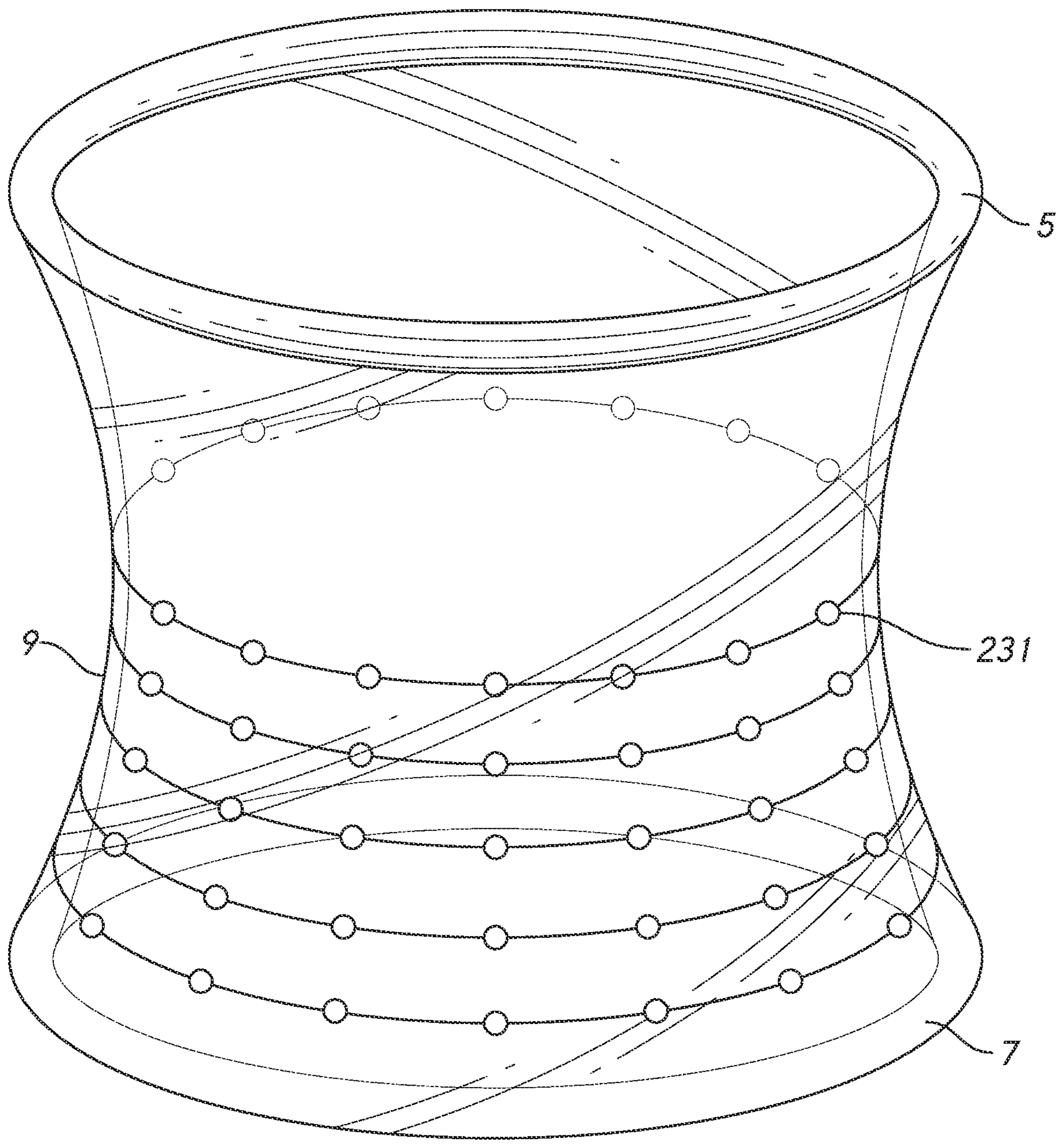
FIG. 34 is a perspective side view of a lighted surgical access system in accordance with various embodiments of the present invention.
Figure 35:
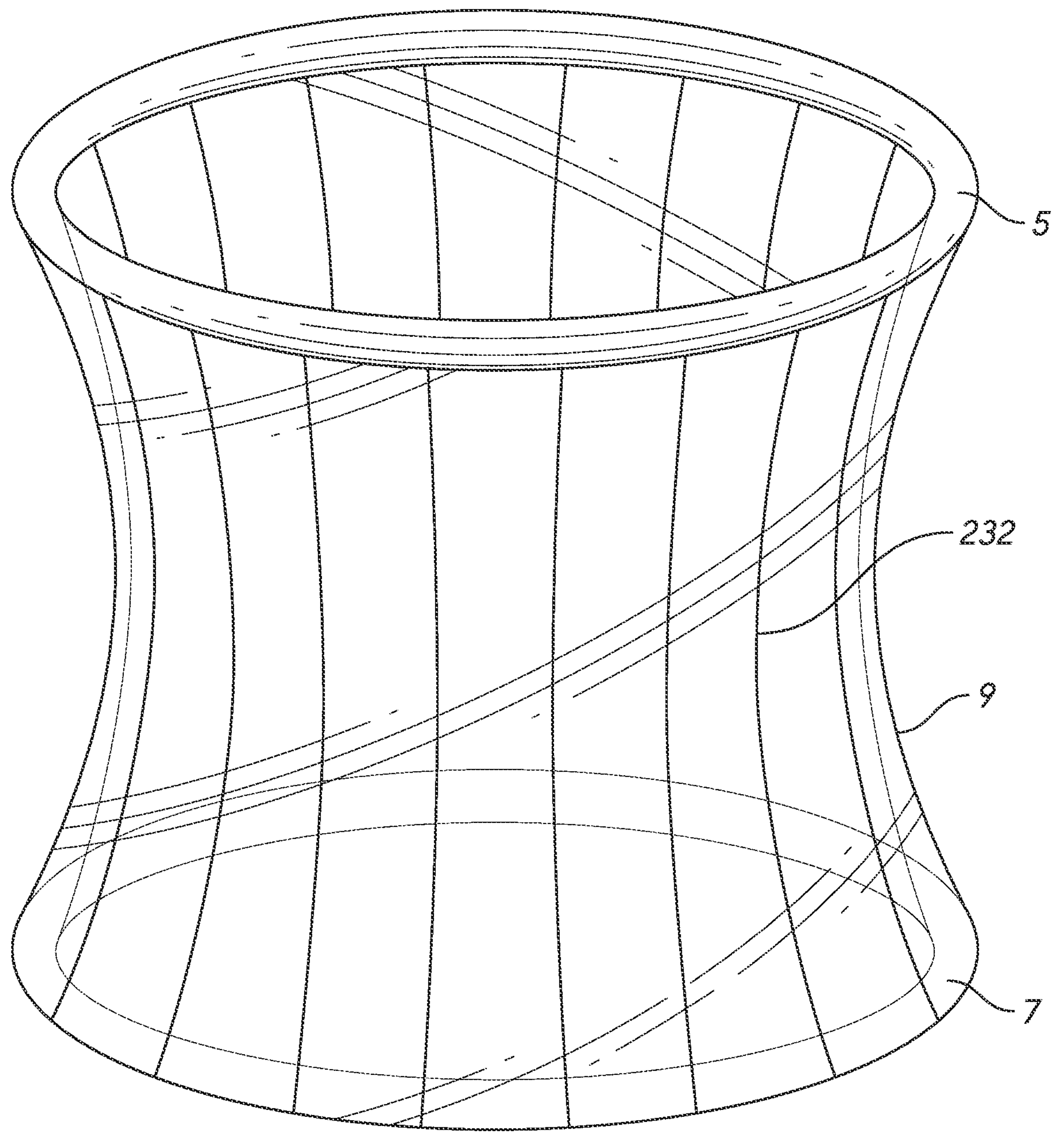
FIG. 35 is a perspective side view of a lighted surgical access system in accordance with various embodiments of the present invention.

In various embodiments, as shown for example in FIGS. 32-33, the sheath 9, or portions of the sheath, e.g., a distal portion of the sheath, includes a reflective sheet and/or photoluminescent sheet, coating or film embedded or otherwise attached to the sheath. The reflective sheet, coating, film, or any combination, e.g., reflective film 191, thereof reflects light from the POF, LEDs and any various equivalents or combinations thereof, away from the outer ring and towards the internal body cavity. In various embodiments, the photoluminescent sheet, coating, film or any combination thereof, e.g., photoluminescent film 192, absorbs direct and/or reflected light from an external light source, such as overhead surgical lights, and emits light away from the outer ring and towards the internal body cavity. In various embodiments, the sheath includes a pocket arranged to temporarily hold or contain an adaptor, light cable and/or portions of the POF for removal and connection to the respective components for use in the surgical procedure.

In various embodiments, one or more LED strips or strings, POFs, or the like may be attached or integrated into the sheath. In various embodiments, one or more LED strips or strings, POFs, e.g., side and/or end glow POFs, or the like, and/or any combination thereof may be arranged circumferentially around or within the sheath and/or stacked or spaced relative to each other, e.g., LEDs 231, as shown for example in FIG. 34. In various embodiments, one or more LED strips or strings, POFs, e.g., side and/or end glow POFs, or the like, and/or any combination thereof may be arranged longitudinally, extending from a proximal portion of the sheath to a distal portion of the sheath, circumferentially around or within the sheath and/or spaced relative to each other, e.g., POFs 232, as shown for example in FIG. 35. In various embodiments, the one or more LED strips or strings, side glow POFs, or the like, and/or any combination thereof may be arranged longitudinally as well as in a direction traverse the longitudinal direction, e.g., horizontally.

Figure 36A:
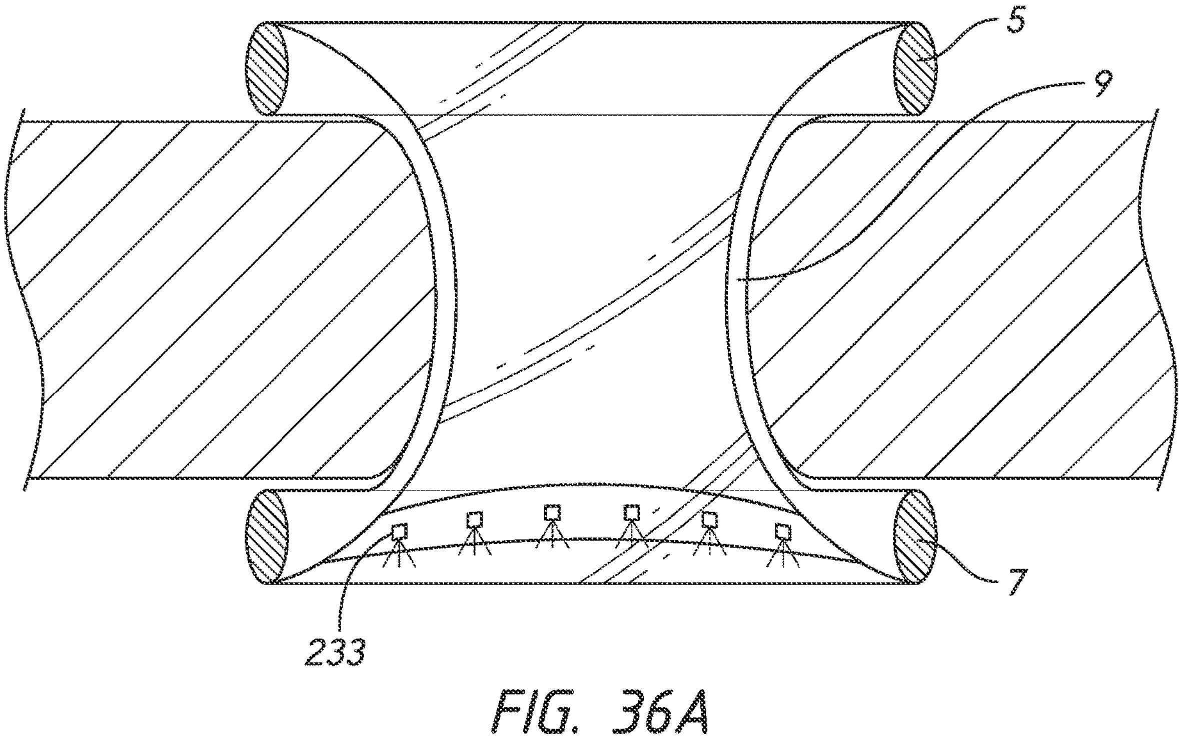
FIG. 36A is a cross-sectional side view of a lighted surgical access system in accordance with various embodiments of the present invention.
Figure 36B:
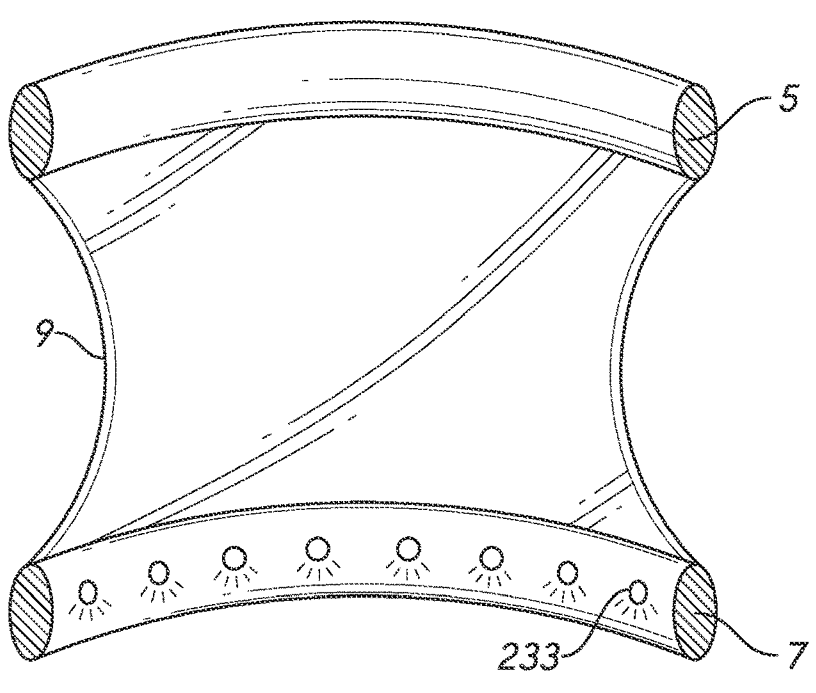
FIG. 36B is a cross-sectional side view of a lighted surgical access system in accordance with various embodiments of the present invention.
Figure 36C:
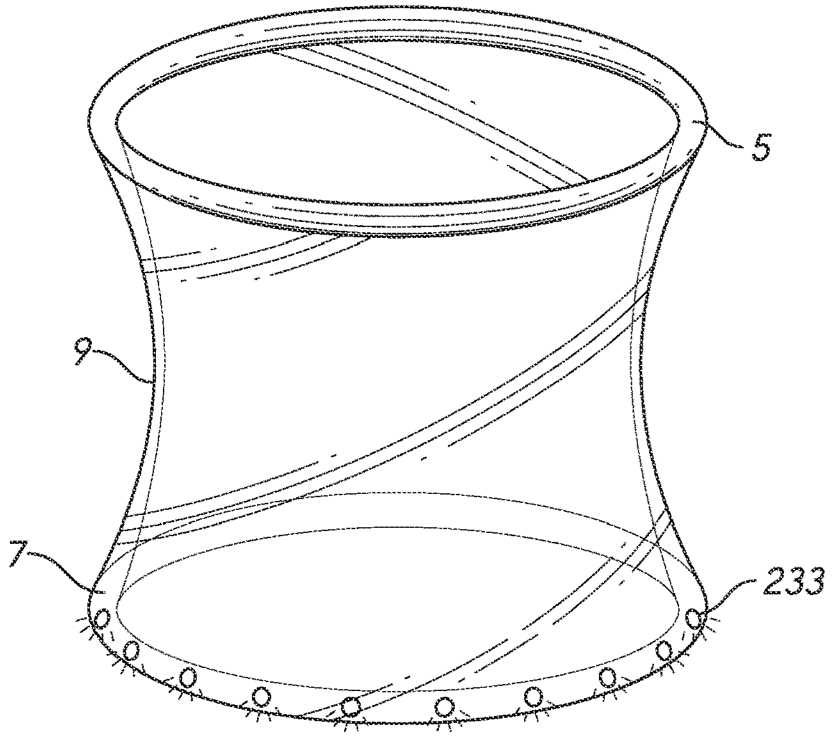
FIG. 36C is a perspective side view of a lighted surgical access system in accordance with various embodiments of the present invention.
Figure 37:
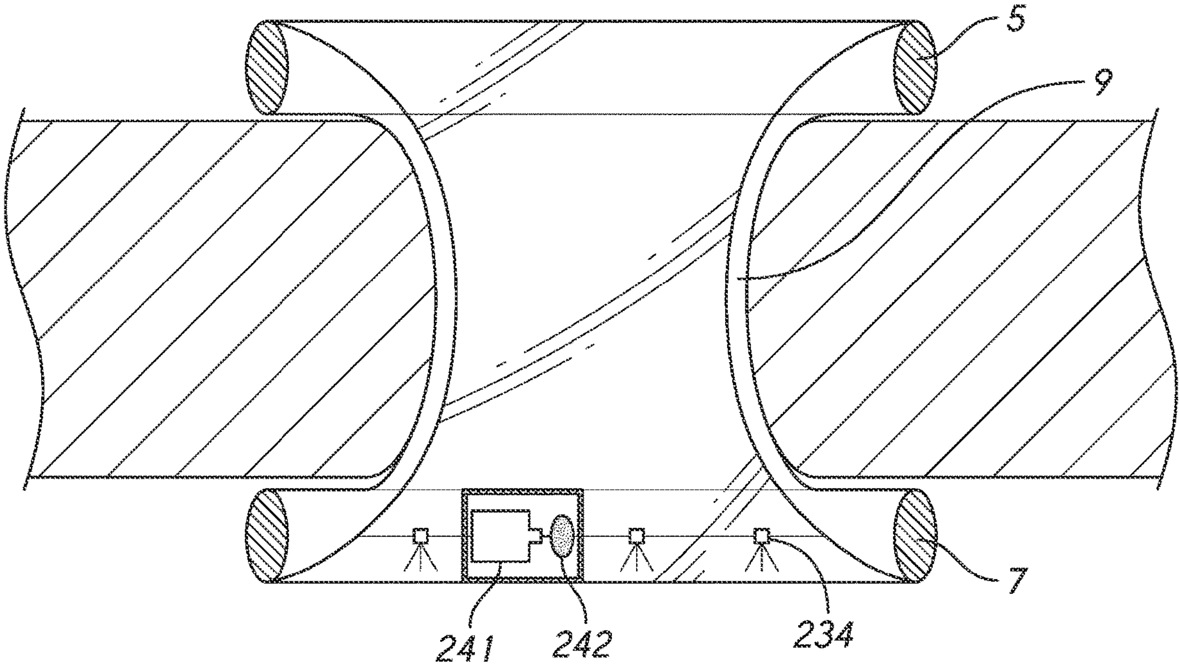
FIG. 37 is a cross-sectional side view of a lighted surgical access system in accordance with various embodiments of the present invention.
Figure 38:
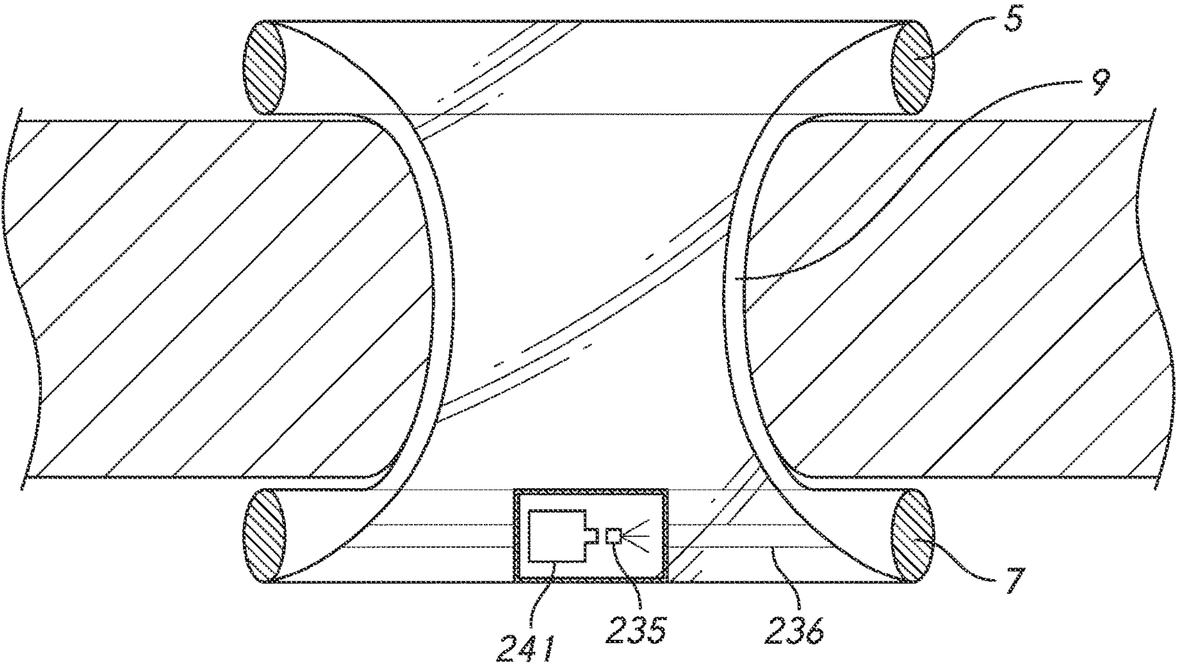
FIG. 38 is a cross-sectional side view of a lighted surgical access system in accordance with various embodiments of the present invention.

In various embodiments, one or more LEDs, LED strips or strings, POFs, or other light emitters and/or carriers may be attached or integrated into only a distal portion of the sheath and/or the inner ring, e.g., LEDs 233, as shown for example in FIGS. 36A-C. For example, in FIG. 36A, LEDs 233 are attachable or integrated onto the distal end of the sheath. In the illustrated embodiment shown in FIG. 36B, LEDs 233 are attached or integrated onto an inner surface or area of the inner ring and in FIG. 36B, LEDs 233 are attached or integrated onto an outer surface or area of the inner ring. In various embodiments, a combination of arrangement of one or more LEDs, LED strips or strings, POFs, or other light emitters and/or carriers may be attached or integrated onto a distal portion of the sheath and/or the inner ring. For example, one or more LEDs may be positioned one or more inner, outer, lower surfaces of the sheath and/or inner ring. In various embodiments, one or more LEDs, LED strips or strings, POFs, or other light emitters and/or carriers are arranged as a curtain, grid or rows of lights positioned or arranged above one another in a successive and/or an alternating or overlapping configuration. In various embodiments, the curtain, grid, or rows of lights are positioned above and/or on the inner ring and/or on the distal end or portion of the sheath. In various embodiments, the curtain, grid, or rows of lights extend past the distal end or portion of the sheath and/or the inner ring into the internal surgical site. In various embodiments, some of the curtain, grid or rows of lights are positioned above and/or on the inner ring and/or the distal end or portion of the sheath and some of the curtain, grid or rows of lights are positioned below or past the inner ring and/or the distal end or portion of the sheath.

In various embodiments, a net lighting is provided and is removably attached to the inner or outer rings. The net light comprises one or more LEDs, LED strips or strings, POFs, or other light emitters and/or carriers arranged in a predetermined pattern removably attached to the inner or outer rings. The spacing between the plurality of lights provide instrument and/or hand access therethrough as well as through the access channel of the sheath. The plurality of lights are provided in a grid-like pattern having a rectangle, square, diamond shape or other similar spacing or openings to provide instrument and/or hand access therethrough. In various embodiments, the plurality of lights are arranged in a row or column only like pattern to increase the spacing therebetween. In various embodiments, portions of the net lighting are movable relative to other portions of the net lighting to provide instrument of hand access there through. For example, a row of light emitters and an adjacent row of light emitters are movable relative to each other or one is stationary and the other movable such that spacing is provided between the rows of light emitters allowing unobstructed instrument and/or hand access there through. In various embodiments, the movable portions of the net lighting are biased and/or elastic, thereby returning back to their initial position after moved to a different position. In various embodiments, the movable portions of the net lighting comprise shape memory material or the like, thereby remaining in a position in which the portions of the lighting was last moved. The net lighting provides lighting along, above and/or below the sheath and/or its access channel.

In various embodiments, one or more power sources, e.g., a battery, and/or switches or buttons controlling the power sources and/or one or more LEDs, may be attached or integrated into only a distal portion of the sheath and/or the inner ring. For example, as shown for example in FIG. 37, in various embodiments, a push button 242 is connected to a battery 241 encased or disposed within or mounted on an outer surface of the inner ring 7 and to one or more LEDs 234 encased or disposed within or along an outer surface of the inner ring. The push button is configured to turn on and off the one or more LEDs, collectively, individually or in groups. As shown for example in FIG. 38, in various embodiments, one or more light carriers 236 are optically connected to the one or more LEDs 235 to transmit light from the one or more LEDs towards the inner body cavity and/or circumferentially around the inner ring 7. In various embodiments, a power source is provided to power the one or more LEDs, LED strips or strings, or other similar light emitters. The power source, in various embodiments, is embedded or attached to the sheath, e.g., placed in a pocket on the sheath, or, in various embodiments, is located externally or outside the internal surgical site, body cavity and/or opening.

Figure 39A:
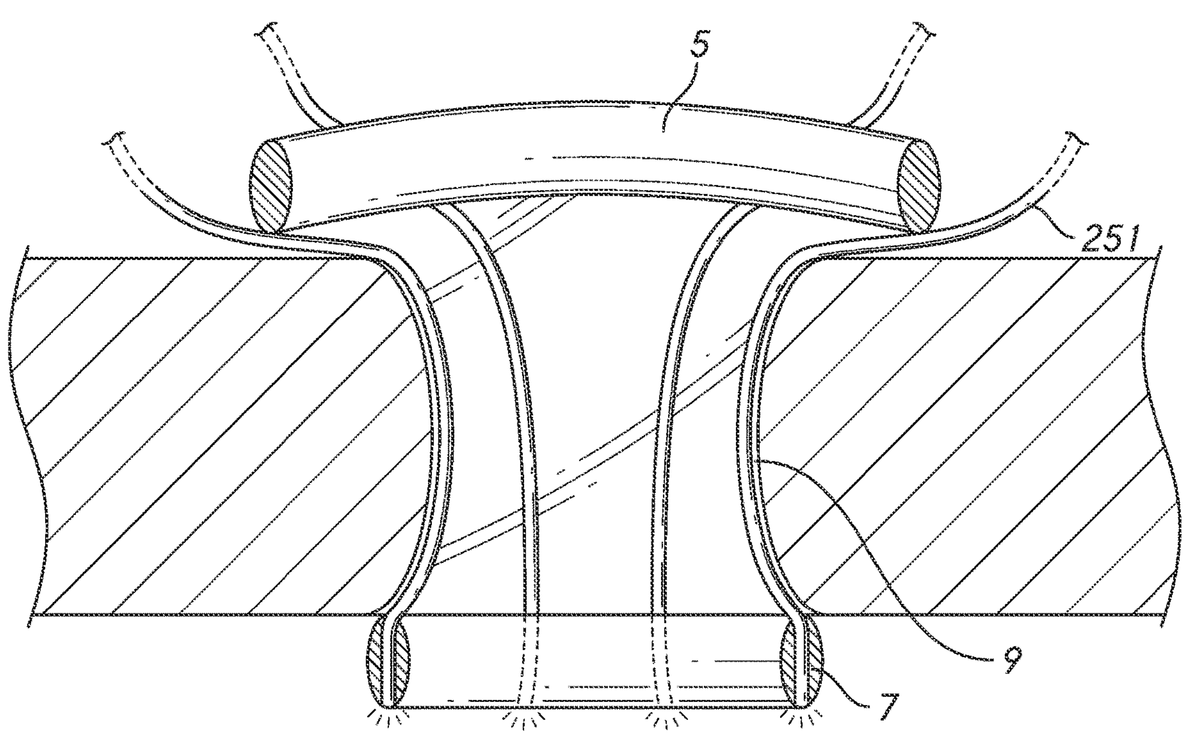
FIG. 39A is a cross-sectional side view of a lighted surgical access system in accordance with various embodiments of the present invention.
Figure 39B:
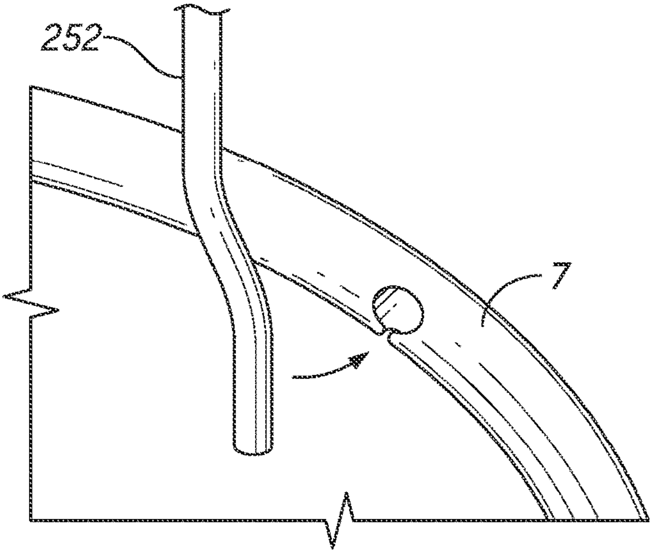
FIG. 39B is a perspective top view of portions of a lighted surgical access system in accordance with various embodiments of the present invention.
Figure 40A:
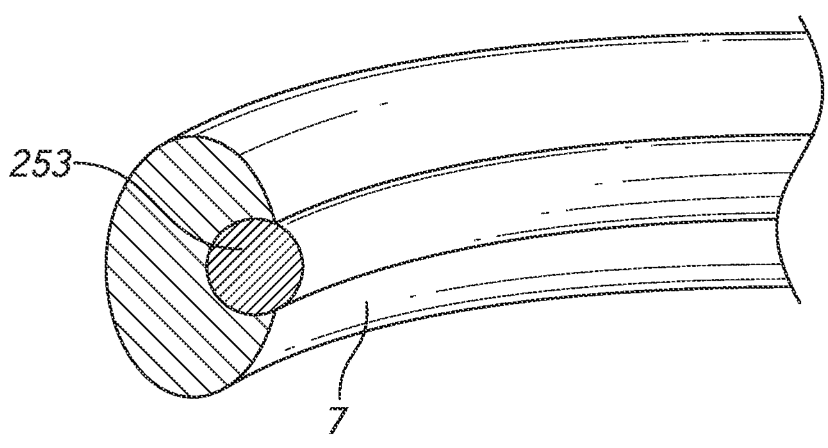
FIG. 40A-B are cross-sectional side views of portions of a lighted surgical access system in accordance with various embodiments of the present invention.
Figure 40B:
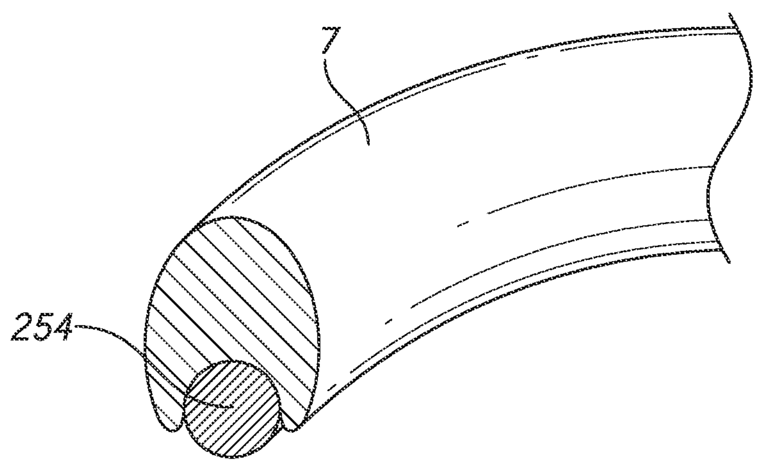

In various embodiments, one or more openings, apertures, grooves, channels, slots or openings are provided within the inner and/or outer rings to connect or attach the one or more POFs, LEDs or the like to the respective inner and/or outer rings. For example, as shown in FIG. 39A, in various embodiments, one or more apertures, grooves, channels, slots or openings in the inner ring provides an pass-through or a snap or friction fit connection between distal ends or portions of one or more POFs, e.g., POFs 251, and the inner ring 7. In various embodiments, one or more apertures, apertures, grooves, channels, slots or openings in the inner ring are tapered or having differing diameters therein or at different ends allowing one or more POFs, LEDs or the like from entering but not exiting the aperture, groove, channel, slot or opening in the inner ring. In various embodiments, the inner ring 7, for example, as shown in FIG. 39B, has one or more grooves, channels, or slots, each having an opening directed towards the center of the sheath and are arranged to attach to or capture a side portion of a longitudinally extending POF, e.g., POF 252. In various embodiments, the inner ring 7, for example, as shown in FIG. 40A, has one or more circumferential grooves, channels, or slots, each having an opening directed towards the center of the sheath or access channel and are arranged to attach to or capture a circumferentially or radially extending POF, e.g., POF 253. In various embodiments, the inner ring 7, for example, as shown in FIG. 40B, has one or more circumferential grooves, channels, or slots, each having an opening directed down or under the inner ring facing towards the inner body cavity, internal surgical site, or parallel to the longitudinal axis and are arranged to attach to or capture a circumferentially or radially extending POF, e.g., POF 254. In various embodiments, the inner ring has one or more apertures or openings, through which a portion of a POF, e.g., a longitudinally extending POF, is attached, captured and/or extends therethrough.

Figure 41:
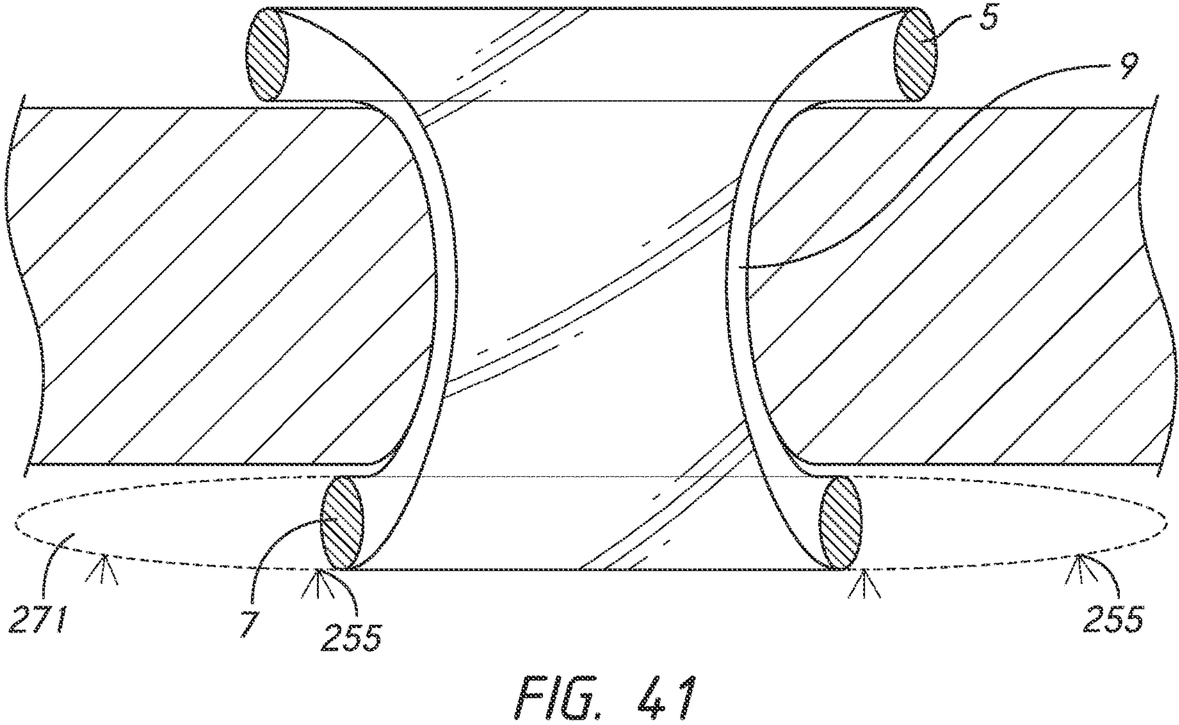
FIG. 41 is a cross-sectional side view of a lighted surgical access system in accordance with various embodiments of the present invention.

In various embodiments, the inner ring or portions thereof may be inflatable. In various embodiments, for example, as shown in FIG. 41, a balloon 271 is attached to or integrated into the inner ring 7. In various embodiments, the balloon may be provided separately as a separate component from the inner ring yet positioned near the inner ring and/or the distal end of the sheath. In various embodiments, the balloon may be positioned next to and/or below the inner ring. In various embodiments, the balloon may be an inflatable disk, torus, ring or one or more curved inflatable portions, inflated by air, fluid, or the like. The POF or distal portions thereof, e.g., POF 255, in various embodiments, is integrated or attached to the balloon, the inflatable inner ring or portions thereof and through inflation of such, the positioning of the POF or portions thereof and thus the light distribution from portions of the POF can be selectively adjusted relative to a longitudinal axis of the sheath. In various embodiments, the balloon or inflatable inner ring are shaped or dimensioned to position the POF, collectively, individually or in groups, in a particular direction, e.g., horizontally, vertically, or angled, relative to or towards the inner body cavity. In various embodiments, the balloon or portions thereof is expandable away from and/or below the inner ring. In various embodiments, portions of balloon and/or inflatable inner ring are selectively inflatable having separate isolated inflatable sections and/or inflatable sources. In various embodiments, one or more valves, tubing and/or pumps are provided to inflate the balloon, inner ring and/or portions or any combination thereof. In various embodiments, other light sources, carriers, emitters, e.g., LEDs, in lieu of or in addition to the POF may be integrated or attached to the balloon, the inflatable inner ring or portions thereof.

Figure 42:
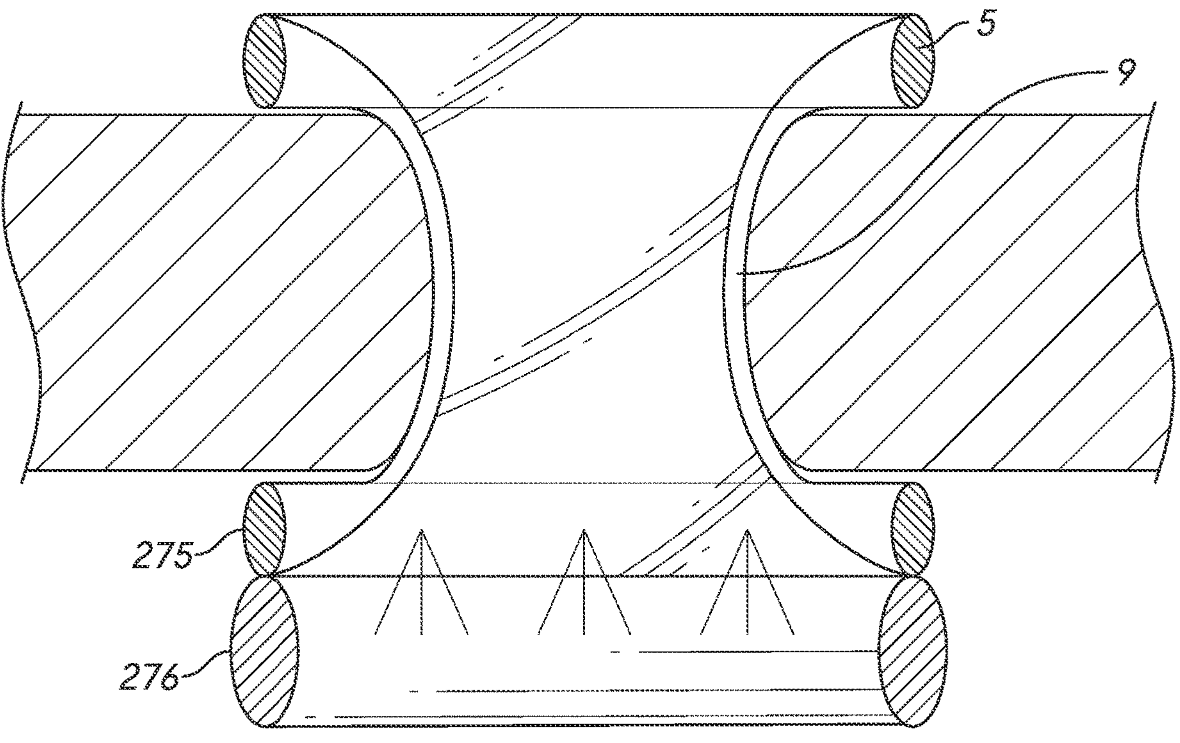
FIG. 42 is a cross-sectional side view of a lighted surgical access system in accordance with various embodiments of the present invention.

In various embodiments, the inner ring or support may comprise of one or more rings or curved portions next to and/or stacked relative to each other. In various embodiments, the inner ring or support may comprise of one or more rings or curved portions in which the POF, e.g., the POF tail, and/or other light emitters, carriers or the like, are positioned within or attached to one or more of the rings of the inner ring. In various embodiments, for example, as shown in FIG. 42, the inner ring or support may comprise an upper ring 275 and a lower ring 276 in which the POF tail is positioned in the upper ring 275 and the lower ring 276 separates the POF tail from the inner body cavity. In various embodiments, the inner ring or support or portions thereof may include one or more lumens, slots or grooves arranged to receive the POF or distal portions of the POF. In various embodiments, the one or more lumens, slots or grooves are arranged, shaped or dimensioned to position the POF, collectively, individually or in groups, in a particular direction, e.g., horizontally, vertically, or angled, relative to or towards the inner body cavity. In various embodiments, the inner ring or support or portions thereof in addition or in lieu of the POF or other light emitters are filled with chemiluminescent material that when activated, e.g., agitated, emits light towards the inner body cavity. In various embodiments, the inner ring or support or portions thereof is transparent, translucent, reflective and/or otherwise made of or comprises a material that allows or facilitates light or minimally obstructs light emitted from the POF and/or other light sources towards the inner body cavity. In various embodiments, the inner ring or support or portions thereof in its entirety or one or more portions thereof is made of one or more side-glow POFs. In various embodiments, the inner and/or outer ring or portions of the sheath comprises a removable attachment portion comprising, for example, a hook and loop surface or connection, such that one or more power source, light source and/or light carrier having a corresponding hook and loop surface or connection is removably attachable thereto.

In various embodiments, one or more optical fibers arranged to carry light from an external light source are attached or integrated into the sheath extending from a proximal end or portion of the sheath to a distal portion or end of the sheath to illuminate the internal body cavity and/or the access channel. In various embodiments, the one or more optical fibers may be provided externally as a bundle of optical fibers and then separated individually or in groups and disposed along and around the sheath. In various embodiments, the bundle of optical fibers carry light from a single source and separate as individual or groups of optical fibers that are distributed around and along the sheath. Light is emitted from a distal end and/or along one or more of the distributed optical fibers.

Figure 43:
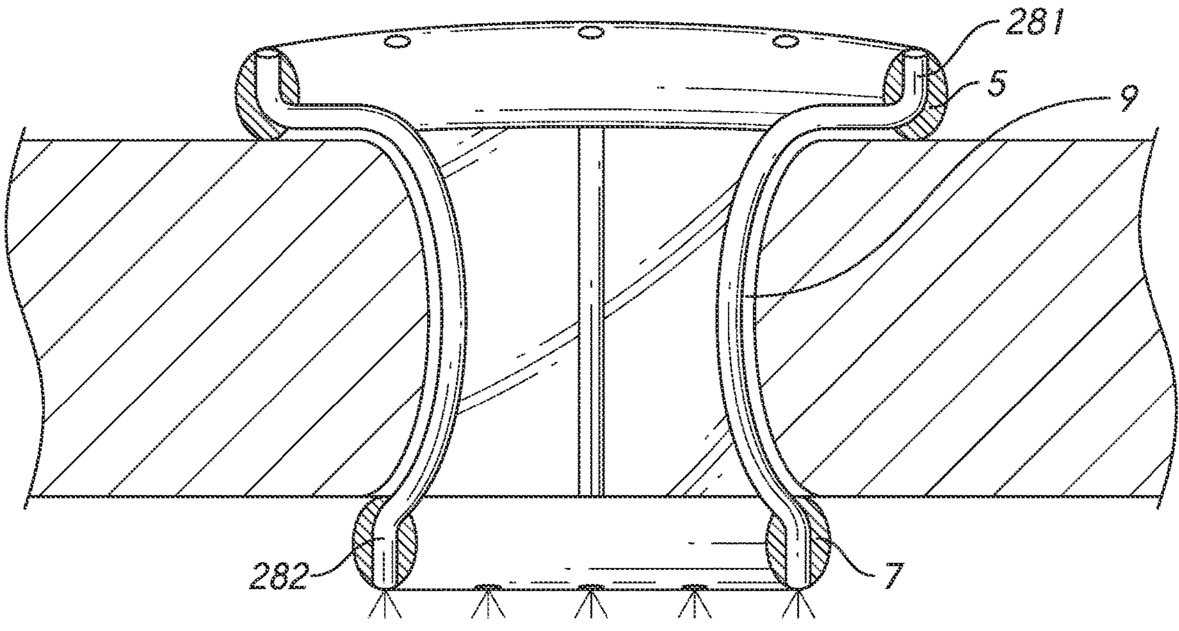
FIG. 43 is a cross-sectional side view of a lighted surgical access system in accordance with various embodiments of the present invention.

In various embodiments, one or more light pipes are provided that passively capture and/or channel light externally. In various embodiments, for example, as shown in FIG. 43, one or more light pipes 281, 282 extend from an outer ring 5 to an inner ring 7 along the sheath 9. In various embodiments, the one or more light pipes are integrated or otherwise attached to the outer ring and/or the inner ring. Proximal ends of the one or more light pipes are connected to one or more openings, slots, channels or apertures in the outer ring and distal ends of the one or more light pipes are connected to one or more openings, channels, slots or apertures in the inner ring. Portions of the one or more light pipes may be embedded or otherwise attached to the sheath and/or between walls of the sheath. Separate coverings or sleeves may further cover and attach the one or more light pipes to the sheath and in various embodiments, reflective material may also be included to assist in further illumination of the internal surgical site and/or opening. In various embodiments, the one or more light pipes may be disposed within the access channel of the sheath. In various embodiments, the one or more light pipes may include cuts or scoring to further direct light in a particular direction, e.g., into the internal surgical site and/or the access channel. In various embodiments, other light other light sources, carriers, emitters, e.g., LEDs, POFs, in addition to the one or more light pipes may also be integrated or attached to the sheath and/or ring as described throughout the description.

In various embodiments, a guard, e.g., an instrument protector and/or morcellation guard, arranged to protect the sheath and/or the surrounding body wall may be provided. Attached or integrated into the guard may be the POF or other light emitters as described throughout the application. For example, in various embodiments, one or more light emitters are embedded in or otherwise attached to a morcellation/instrument guard. The guard is adjustable radially to adjust the diameter delimited by the guard. In various embodiments, the guard is attachable or provided with the retractor. In various embodiments, the guard is provided independently or used without the retractor. In various embodiments, the guard is more puncture and/or tear resistant than the sheath, e.g., being made of a more puncture and/or tear resistant material. In various embodiments, the guard is more rigid than the sheath and/or arranged to maintain a resting hour-glass shape. In various embodiments, the sheath is inserted through an opening defined or delimited by the guard. In various embodiments, the guard is insertable through the access channel of the sheath and/or biased to rest or radially push against the sheath. Light is emitted from a distal end of the light emitters and/or a distal end or portion of the guard. Light, in various embodiments, is provided via a light emitter system connectable thereto and comprising one or more light sources, such as LEDs, POF, light carrier and so forth. In various embodiments, the various embodiments of retractors and corresponding light sources, carriers, emitters, as described throughout the description may be provided with or integrated or attached to the guard to further assist in illumination of the internal surgical site, patient anatomy, and/or access channel. In FIG. 23, a guard 230 is shown.

In various embodiments, a metal or point retractor may be provided in which one or more light emitters may be integrated or attached thereto. In various embodiments, one or more LEDs are attached to an outer surface of a point retractor and in various embodiments, one or more LEDs are magnetically connected to the magnetically compatible surface of a point retractor. For example, the one or more LEDs may include one or more magnets attached to one side of the LEDs and the opposing side of the magnet attached to the point retractor. In various embodiments, one or more LEDs are magnetically connected to a magnet, magnetized or magnetically compatible external surface disposed outside of the body. For example, a power supply or controller for the one or more LEDs disposed externally may include a magnetic surface magnetically connected to a magnetic surface or portion attached to or part of the LEDs. In various embodiments, one or more light emitters and/or carriers and/or portions or attachments thereto may be integrated or attached surgical instruments, such as graspers or scalpels, and/or accessories, such as surgical gloves. In various embodiments, the various embodiments of retractors and corresponding light sources, carriers, emitters, as described throughout the description may be provided with or integrated or attached to the point retractor and/or instruments to further assist in illumination of the internal surgical site, patient anatomy, and/or access channel.

In various embodiments, one or more light carriers or emitters, e.g., an LED string or strip, or a transparent needle or obturator, may be provided separate from the sheath and/or POF illuminate portions of the inner cavity. In various embodiments, such light carriers or emitters are arranged to be freely or unrestrictedly arranged relative to the sheath to, for example, illuminate a particular area or portion of the internal body cavity. In various embodiments, the various embodiments of retractors and corresponding light sources, carriers, emitters, as described throughout the description may be provided with or integrated or attached to such light carriers or emitters to further assist in illumination of the internal surgical site, patient anatomy, and/or access channel. In various embodiments, one or more enlarged distal portions or ends of the one or more light carriers or emitters or one or more enlarged light carriers or emitters, such as a light ball, may be provided to illuminate the internal body cavity or a particular area or portion of the internal body cavity. In various embodiments, one or more tethers, straps or connectors may be provided to assist in the placement, positioning and/or removal of the one or more light emitters and/or carriers not otherwise attached or integrated with the sheath and/or inner ring. For example, in various embodiments, one or more tethers, straps or connectors may be attached to the one or more light emitters and/or carriers and/or related power sources not otherwise attached or integrated with the sheath and/or inner ring to assist in placement, positioning and/or removal of the one or more light emitters and/or carriers and/or power sources. In various embodiments, one or more light emitters and/or carriers or portions or attachments thereto may be arranged or configured to emit omnidirectional light and/or focused light, e.g., downward and/or circumferentially directed light. In accordance with various embodiments, light is provided by or to the various embodiments by a light emitter system connectable there to and comprising one or more light sources, carriers, emitters or the like, including but not limited to, light boxes, LEDs, POFs and any various equivalents or combinations thereof integrated therein or attached thereto.

The above description is provided to enable any person skilled in the art to make and use the devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A lighted surgical access system to illuminate internally a body cavity comprising:

an outer ring arranged to be placed outside of a body cavity;

an inner ring arranged to be placed inside of the body cavity;

a sheath having a proximal end connected to the outer ring and a distal end connected the inner ring, the sheath delimiting an access channel extending from the outer ring to the inner ring through a central lumen of the sheath, and the sheath having an adjustable length being configured to wrap the outer ring around a proximal portion of the sheath; and a light emitter system comprising a light skirt comprising:

a hoop circumferentially disposed around and in contact with an outer periphery of the sheath and movable longitudinally along the sheath and not past the inner ring, the hoop being rotatable relative to the sheath and having an outer circumference smaller than an inner circumference of the inner ring and positioned outside of the access channel; and a plurality of elongate light strands connected to and extending from the hoop and arranged to emit light away from the hoop and the inner ring, the plurality of elongate light strands hanging over the inner ring and extending past the inner ring.

2. The system of claim 1 further comprising a plurality of light emitting diodes connectable to the hoop.

3. The system of claim 1 wherein at least one of the plurality of elongate light strands comprises at least one plastic optical fiber.

4. The system of claim 1 wherein at least one of the plurality of elongate light strands comprises at least one light emitting diode.

5. The system of claim 4 further comprising a cap rotatable relative to the outer ring and removably connectable to the outer ring, the cap configured to cover an entire opening of the outer ring, to seal the access channel of the sheath, and comprising a penetrable and sealable material configured to seal against an outer surface of instruments inserted therethrough.

6. The system of claim 5 wherein the light emitter system comprises a light emitter extending away from the cap and above the outer ring, the light emitter comprises a plurality of light emitters, each light emitter being adjustable in position relative to the cap and independently adjustable relative to each other.

7. The system of claim 5 wherein the sheath has a reflective portion and a photoluminescent portion.

8. The system of claim 1 wherein the sheath further comprises a pocket arranged to hold one of a power source, a plastic optical fiber, a light cable or an adaptor.

9. The system of claim 1 wherein the inner ring comprises a chemiluminescent material.

10. The system of claim 1 wherein the sheath comprises a chemiluminescent material.

11. The system of claim 1 wherein the plurality of elongate light strands are bendable, positioned outside of the access channel, and aligned with a longitudinal axis of the sheath and extending inside of the body cavity and wherein each of the plurality of elongate light strands has a width smaller than a width of the outer ring and a length greater than a width of the inner ring.

12. The system of claim 1 wherein the hoop has a diameter smaller than a diameter of the inner ring.

13. A lighted surgical access system to illuminate internally a body cavity comprising:

an outer ring arranged to be placed outside of a body cavity;

an inner ring arranged to be placed inside of the body cavity;

a sheath having a proximal end connected to the outer ring and a distal end connected the inner ring, the sheath delimiting an access channel extending from the outer ring to the inner ring through a central lumen of the sheath, and the sheath having an adjustable length being configured to wrap the outer ring around a proximal portion of the sheath; and a light emitter system comprising:

a light skirt comprising:

a hoop circumferentially disposed around and in contact with an outer periphery of the sheath and movable longitudinally along the sheath and not past the inner ring, the hoop being rotatable relative to the sheath; and at least one elongate light strand connected to and extending from the hoop and arranged to emit light away from the hoop and the inner ring, the at least one elongate light strand extending past the inner ring; and a net lighting extending across the access channel and attached to the inner ring, the net lighting being arranged in a grid pattern having spaces between light emitting diodes, the spaces sized to provide instrument or hand access there through.

14. The system of claim 13 wherein portions of the net lighting are movable relative to other portions of the net lighting to provide instrument or hand access there through, the portions of the net lighting remaining in a position where it has been moved.

15. The system of claim 13 further comprising one or more controllers arranged to selectively activate or deactivate selected portions of the light emitter system and arranged to selectively adjust an illumination and focus of selected portions of the light emitter system.

16. The system of claim 13 wherein the inner ring comprises a reflective material.

17. The system of claim 13 wherein portions of the net lighting are movable relative to other portions of the net lighting to provide instrument or hand access there through, the movable portions of the net lighting being biased, returning back to their initial position after moved to a different position.

18. A lighted surgical access system to illuminate internally a body cavity comprising:

an outer ring arranged to be placed outside of a body cavity;

an inner ring arranged to be placed inside of the body cavity;

a sheath having a proximal end connected to the outer ring and a distal end connected the inner ring, the sheath delimiting an access channel extending from the outer ring to the inner ring through a central lumen of the sheath, and the sheath having an adjustable length being configured to wrap the outer ring around a proximal portion of the sheath; and a light emitter system comprising:

a light skirt comprising:

a hoop circumferentially disposed around and in contact with an outer periphery of the sheath and movable longitudinally along the sheath and not past the inner ring, the hoop being rotatable relative to the sheath; and at least one elongate light strand connected to and extending from the hoop and arranged to emit light away from the hoop and the inner ring, the at least one elongate light strand extending past the inner ring and comprising at least one light emitting diode; and an inflatable balloon attached to the sheath and wherein the light emitter system is attached to the balloon, the balloon being expandable away from the inner ring.

19. The system of claim 18 wherein portions of the balloon are selectively expandable.

20. The system of claim 18 wherein the at least one elongate light strand is tubular and more flexible than the outer ring and wherein the at least one elongate light strand comprises a first elongate light strand having a first size and a second elongate light strand having a second size, the first size being different from the second size.

* * * * *